(12) United States Patent
Gorman et al.

(10) Patent No.: US 11,116,783 B2
(45) Date of Patent: *Sep. 14, 2021

(54) COMBINATION FORMULATION OF TWO ANTIVIRAL COMPOUNDS

(71) Applicant: Gilead Pharmasset LLC, Foster City, CA (US)

(72) Inventors: Eric Gorman, Hayward, CA (US); Erik Mogalian, San Francisco, CA (US); Reza Oliyai, Burlingame, CA (US); Dimitrios Stefanidis, Saratoga, CA (US); Lauren Wiser, San Francisco, CA (US); Vahid Zia, Palo Alto, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,178

(22) Filed: Jun. 16, 2020

(65) Prior Publication Data

US 2021/0000854 A1    Jan. 7, 2021

Related U.S. Application Data

(60) Continuation of application No. 16/669,063, filed on Oct. 30, 2019, now abandoned, which is a continuation of application No. 16/124,111, filed on Sep. 6, 2018, now abandoned, which is a continuation of application No. 15/670,283, filed on Aug. 7, 2017, now Pat. No. 10,086,011, which is a division of application No. 15/282,128, filed on Sep. 30, 2016, now Pat. No. 9,757,406, which is a continuation of application No. 14/168,340, filed on Jan. 30, 2014, now abandoned.

(60) Provisional application No. 61/907,308, filed on Nov. 21, 2013, provisional application No. 61/898,690, filed on Nov. 1, 2013, provisional application No. 61/870,712, filed on Aug. 27, 2013.

(51) Int. Cl.
| | |
|---|---|
| *A61K 31/7072* | (2006.01) |
| *A61K 9/28* | (2006.01) |
| *A61K 31/7056* | (2006.01) |
| *A61K 31/4188* | (2006.01) |
| *A61K 9/16* | (2006.01) |
| *A61K 9/20* | (2006.01) |

(52) U.S. Cl.
CPC ........ *A61K 31/7072* (2013.01); *A61K 9/1623* (2013.01); *A61K 9/1635* (2013.01); *A61K 9/2054* (2013.01); *A61K 9/284* (2013.01); *A61K 31/4188* (2013.01); *A61K 31/7056* (2013.01)

(58) Field of Classification Search
CPC .. A61K 31/4188; A61K 9/2054; A61K 9/284; A61K 31/7056; A61K 9/1635; A61K 31/7072; A61K 9/1623; A61K 2300/00; A61P 31/14; A61P 1/16; A61P 43/00; A61P 31/12
See application file for complete search history.

(56) References Cited

U.S. PATENT DOCUMENTS

| | | |
|---|---|---|
| 3,798,209 A | 3/1974 | Witkowski et al. |
| 3,852,267 A | 12/1974 | Meyer, Jr. et al. |
| RE29,835 E | 11/1978 | Witkowski et al. |
| 4,814,477 A | 3/1989 | Wijnberg et al. |
| 4,957,924 A | 9/1990 | Beauchamp |
| 5,026,687 A | 6/1991 | Yarchoan et al. |
| 5,118,820 A | 6/1992 | Hertel et al. |
| 5,149,794 A | 9/1992 | Yatvin et al. |
| 5,157,027 A | 10/1992 | Biller et al. |
| 5,192,549 A | 3/1993 | Barenolz et al. |
| 5,194,654 A | 3/1993 | Hostetler et al. |
| 5,223,263 A | 6/1993 | Hostetler et al. |
| 5,256,641 A | 10/1993 | Yatvin et al. |
| 5,256,798 A | 10/1993 | Chou et al. |
| 5,372,808 A | 12/1994 | Blatt et al. |
| 5,376,380 A | 12/1994 | Kikuchi et al. |
| 5,405,598 A | 4/1995 | Schinazi et al. |

(Continued)

FOREIGN PATENT DOCUMENTS

| | | |
|---|---|---|
| CA | 2815082 | 5/2013 |
| CN | 1761677 | 4/2006 |

(Continued)

OTHER PUBLICATIONS

U.S. Appl. No. 60/392,350, filed Jun. 28, 2002, Storer et al.

(Continued)

*Primary Examiner* — Jianfeng Song
(74) *Attorney, Agent, or Firm* — Sheppard Mullin Richter & Hampton LLP

(57) ABSTRACT

Disclosed are pharmaceutical compositions comprising Compound I, having the formula:

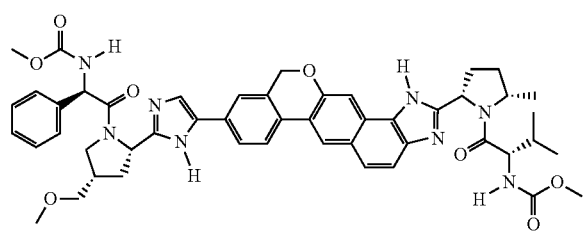

and an effective amount of sofosbuvir wherein the sofosbuvir is substantially crystalline. Also disclosed are methods of use for the pharmaceutical composition.

58 Claims, No Drawings

(56) References Cited

U.S. PATENT DOCUMENTS

| | | |
|---|---|---|
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou et al. |
| 5,462,724 A | 10/1995 | Schinazi et al. |
| 5,463,092 A | 10/1995 | Hostetler et al. |
| 5,496,546 A | 3/1996 | Wang et al. |
| 5,538,865 A | 7/1996 | Reyes et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,610,054 A | 3/1997 | Draper |
| 5,633,358 A | 5/1997 | Gruetzke et al. |
| 5,633,388 A | 5/1997 | Diana et al. |
| 5,676,942 A | 10/1997 | Testa et al. |
| 5,703,058 A | 12/1997 | Schinazi et al. |
| 5,711,944 A | 1/1998 | Gilbert et al. |
| 5,725,859 A | 3/1998 | Omer |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,858,389 A | 1/1999 | Elsherbini |
| 5,869,253 A | 2/1999 | Draper |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,156,501 A | 12/2000 | McGall et al. |
| 6,180,134 B1 | 1/2001 | Zalipsky et al. |
| 6,232,300 B1 | 5/2001 | Schinazi et al. |
| 6,239,159 B1 | 5/2001 | Brown et al. |
| 6,348,587 B1 | 2/2002 | Schinazi et al. |
| 6,372,883 B1 | 4/2002 | Attwood et al. |
| 6,391,859 B1 | 5/2002 | Schinazi et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan et al. |
| 6,455,690 B1 | 9/2002 | Tam et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,555,677 B2 | 4/2003 | Petrillo et al. |
| 6,573,248 B2 | 6/2003 | Ramasamy et al. |
| 6,589,941 B1 | 7/2003 | Fahrig et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,763,607 B2 | 7/2004 | Beyerinck et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,841,566 B2 | 1/2005 | Beaulieu et al. |
| 6,846,810 B2 | 1/2005 | Martin et al. |
| 6,897,201 B2 | 5/2005 | Boyer et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,962,991 B2 | 11/2005 | Dempcy et al. |
| 7,018,985 B1 | 3/2006 | Boyer et al. |
| 7,018,989 B2 | 3/2006 | McGuigan et al. |
| 7,081,449 B2 | 7/2006 | Pietrzkowski et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,217,523 B2 | 5/2007 | Wagner |
| 7,259,186 B2 | 8/2007 | Cink et al. |
| 7,268,119 B2 | 9/2007 | Cook et al. |
| 7,273,624 B2 | 9/2007 | Rosenberg et al. |
| 7,307,065 B2 | 12/2007 | Schinazi et al. |
| 7,323,453 B2 | 1/2008 | Olsen et al. |
| 7,365,057 B2 | 4/2008 | LaColla et al. |
| 7,386,398 B2 | 6/2008 | Coulombe et al. |
| 7,390,791 B2 | 6/2008 | Becker et al. |
| 7,429,572 B2 | 9/2008 | Clark |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | LaColla et al. |
| 7,704,992 B2 | 4/2010 | Bachand et al. |
| 7,741,347 B2 | 6/2010 | Bachand et al. |
| 7,754,699 B2 | 7/2010 | Chun et al. |
| 7,780,988 B2 | 8/2010 | Beyerinck et al. |
| 7,879,815 B2 | 2/2011 | MacCoss et al. |
| 7,964,580 B2 | 6/2011 | Sofia et al. |
| 8,088,368 B2 | 1/2012 | Guo et al. |
| 8,147,818 B2 | 4/2012 | Bachand et al. |
| 8,148,349 B2 | 4/2012 | Meppen et al. |
| 8,173,621 B2 | 5/2012 | Du et al. |
| 8,221,737 B2 | 7/2012 | Or et al. |
| 8,273,341 B2 | 9/2012 | Guo et al. |
| 8,303,944 B2 | 11/2012 | Bachand et al. |
| 8,334,270 B2 | 12/2012 | Sofia et al. |
| 8,362,068 B2 | 1/2013 | Dousson et al. |
| 8,377,980 B2 | 2/2013 | Belema et al. |
| 8,383,094 B2 | 2/2013 | Belema et al. |
| 8,415,322 B2 | 4/2013 | Clark |
| 8,466,159 B2 | 6/2013 | Bernstein et al. |
| 8,492,386 B2 | 7/2013 | Bernstein et al. |
| 8,546,402 B2 | 10/2013 | Sokoloff et al. |
| 8,551,973 B2 | 10/2013 | Bao et al. |
| 8,575,118 B2 | 11/2013 | Guo et al. |
| 8,575,135 B2 | 11/2013 | Bacon et al. |
| 8,580,765 B2 | 11/2013 | Sofia et al. |
| 8,618,076 B2 | 12/2013 | Ross et al. |
| 8,653,070 B2 | 2/2014 | Qiu et al. |
| 8,669,234 B2 | 3/2014 | Guo et al. |
| 8,680,106 B2 | 3/2014 | Bernstein et al. |
| 8,685,984 B2 | 4/2014 | Bernstein et al. |
| 8,691,938 B2 | 4/2014 | DeGoey et al. |
| 8,735,372 B2 | 5/2014 | Du et al. |
| 8,796,466 B2 | 8/2014 | Bender et al. |
| 8,809,265 B2 | 8/2014 | Bernstein et al. |
| 8,815,858 B2 | 8/2014 | Bjornson et al. |
| 8,822,430 B2 | 9/2014 | Bacon et al. |
| 8,841,278 B2 | 9/2014 | Bacon et al. |
| 8,841,340 B2 | 9/2014 | Hashash et al. |
| 8,891,379 B2 | 11/2014 | Ninan et al. |
| 8,906,880 B2 | 12/2014 | Du et al. |

(56) References Cited

U.S. PATENT DOCUMENTS

| | | |
|---|---|---|
| 8,921,341 B2 | 12/2014 | Bacon et al. |
| 8,937,150 B2 | 1/2015 | DeGoey et al. |
| 8,940,718 B2 | 1/2015 | Bacon et al. |
| 8,957,046 B2 | 2/2015 | Du et al. |
| 8,969,357 B2 | 3/2015 | Bernstein et al. |
| 8,969,588 B2 | 3/2015 | Scott et al. |
| 8,993,578 B2 | 3/2015 | Bernstein et al. |
| 9,034,832 B2 | 5/2015 | Gao et al. |
| 9,051,340 B2 | 6/2015 | Bacon et al. |
| 9,056,860 B2 | 6/2015 | Scott et al. |
| 9,079,887 B2 | 7/2015 | Bacon et al. |
| 9,084,730 B2 | 7/2015 | Bedos et al. |
| 9,085,573 B2 | 7/2015 | Du et al. |
| 9,109,001 B2 | 8/2015 | Parsy et al. |
| 9,125,904 B1 | 9/2015 | Wiles et al. |
| 9,156,818 B2 | 10/2015 | Or et al. |
| 9,156,823 B2 | 10/2015 | Bacon et al. |
| 9,221,833 B2 | 12/2015 | Bacon et al. |
| 9,233,974 B2 | 1/2016 | Link et al. |
| 9,393,256 B2 | 7/2016 | Ray et al. |
| 9,409,891 B2 | 8/2016 | Hashash et al. |
| 9,452,154 B2 | 9/2016 | Delaney, IV et al. |
| 9,511,056 B2 | 12/2016 | Bacon et al. |
| 9,585,906 B2 | 3/2017 | Du et al. |
| 9,757,406 B2 | 9/2017 | Gorman et al. |
| 9,868,745 B2 | 1/2018 | Bacon et al. |
| 10,086,011 B2 | 10/2018 | Gorman et al. |
| 10,183,037 B2 | 1/2019 | Du et al. |
| 2001/0034440 A1 | 10/2001 | Shepard et al. |
| 2002/0058635 A1 | 5/2002 | Averett |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0109697 A1 | 6/2003 | Shepard et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0187018 A1 | 10/2003 | Llinas-Brunet et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0026853 A1 | 2/2005 | Mekouar et al. |
| 2005/0031588 A1 | 2/2005 | Sommadossi et al. |
| 2005/0059632 A1 | 3/2005 | Storer et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2005/0267018 A1 | 12/2005 | Blatt et al. |
| 2006/0003951 A1 | 1/2006 | Mekouar et al. |
| 2006/0014943 A1 | 1/2006 | Dempcy et al. |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0166964 A1 | 7/2006 | Hudyma et al. |
| 2006/0194749 A1 | 8/2006 | Keicher et al. |
| 2006/0199783 A1 | 9/2006 | Wang et al. |
| 2006/0241064 A1 | 10/2006 | Roberts et al. |
| 2006/0276511 A1 | 12/2006 | Serrano-Wu et al. |
| 2006/0293306 A1 | 12/2006 | Beaulieu et al. |
| 2007/0015905 A1 | 1/2007 | LaColla et al. |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0197463 A1 | 8/2007 | Chun et al. |
| 2007/0218138 A1 | 9/2007 | Bittorf et al. |
| 2007/0225249 A1 | 9/2007 | Shi |
| 2007/0265222 A1 | 11/2007 | MacCoss et al. |
| 2007/0275912 A1 | 11/2007 | Bhat et al. |
| 2007/0275947 A1 | 11/2007 | Bergstrom |
| 2008/0070861 A1 | 3/2008 | Clark |
| 2008/0253995 A1 | 10/2008 | Clark |
| 2009/0004135 A1 | 1/2009 | Clark |
| 2009/0036666 A1 | 2/2009 | Clark |
| 2009/0068140 A1 | 3/2009 | Bachand et al. |
| 2009/0137521 A1 | 5/2009 | Hamilton et al. |
| 2009/0176732 A1 | 7/2009 | Beigelman et al. |
| 2009/0202478 A1 | 8/2009 | Bachand et al. |
| 2009/0202483 A1 | 8/2009 | Bachand et al. |
| 2009/0233879 A1 | 9/2009 | Reddy et al. |
| 2009/0280084 A1 | 11/2009 | Schinazi et al. |
| 2009/0291138 A1* | 11/2009 | Watanabe ............ A61K 9/2866 424/480 |
| 2009/0306007 A1 | 12/2009 | Wagner |
| 2009/0311414 A1 | 12/2009 | Kessler et al. |
| 2010/0022468 A1 | 1/2010 | Meppen et al. |
| 2010/0029008 A1 | 2/2010 | Rojas Stutz et al. |
| 2010/0035835 A1 | 2/2010 | Narjes et al. |
| 2010/0048917 A1 | 2/2010 | Wang et al. |
| 2010/0080772 A1 | 4/2010 | Belema et al. |
| 2010/0081628 A1 | 4/2010 | Du et al. |
| 2010/0137576 A1 | 6/2010 | Stec et al. |
| 2010/0152128 A1 | 6/2010 | Attenni et al. |
| 2010/0160335 A1 | 6/2010 | Kohno et al. |
| 2010/0173863 A1 | 7/2010 | Schinazi et al. |
| 2010/0227801 A1 | 9/2010 | Hopkins |
| 2010/0249068 A1 | 9/2010 | Beigelman et al. |
| 2010/0249190 A1 | 9/2010 | Lopez et al. |
| 2010/0256184 A1* | 10/2010 | Rowe .................. A61K 9/2054 514/312 |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0310512 A1 | 12/2010 | Guo et al. |
| 2010/0316594 A1 | 12/2010 | Sommadossi et al. |
| 2010/0316607 A1 | 12/2010 | Or et al. |
| 2011/0015146 A1 | 1/2011 | Sofia et al. |
| 2011/0064698 A1 | 3/2011 | Or et al. |
| 2011/0077280 A1 | 3/2011 | Bender et al. |
| 2011/0092415 A1 | 4/2011 | DeGoey et al. |
| 2011/0124592 A1 | 5/2011 | McGuigan et al. |
| 2011/0135604 A1 | 6/2011 | Casarez et al. |

(56) References Cited

U.S. PATENT DOCUMENTS

| | | |
|---|---|---|
| 2011/0137633 A1 | 6/2011 | Hutchins et al. |
| 2011/0142798 A1 | 6/2011 | Qiu et al. |
| 2011/0150827 A1 | 6/2011 | Dousson et al. |
| 2011/0245484 A1 | 10/2011 | Ross et al. |
| 2011/0251152 A1* | 10/2011 | Ross .................... C07F 9/2479 514/51 |
| 2011/0257122 A1 | 10/2011 | Sofia et al. |
| 2011/0286961 A1 | 11/2011 | Belema et al. |
| 2011/0306541 A1 | 12/2011 | Delaney, IV et al. |
| 2012/0107278 A1 | 5/2012 | Berrey et al. |
| 2012/0157404 A1 | 6/2012 | Guo et al. |
| 2012/0157463 A1 | 6/2012 | Sokoloff et al. |
| 2012/0245335 A1 | 9/2012 | Clark |
| 2012/0264711 A1 | 10/2012 | Guo et al. |
| 2013/0029929 A1 | 1/2013 | Sofia et al. |
| 2013/0109647 A1 | 5/2013 | Berrey et al. |
| 2013/0136776 A1 | 5/2013 | Cleary et al. |
| 2013/0137654 A1 | 5/2013 | Ross et al. |
| 2013/0137877 A1 | 5/2013 | Guo et al. |
| 2013/0156732 A1 | 6/2013 | Bacon et al. |
| 2013/0164260 A1 | 6/2013 | Bacon et al. |
| 2013/0165401 A1 | 6/2013 | Ross et al. |
| 2013/0165644 A1 | 6/2013 | Ross et al. |
| 2013/0171102 A1 | 7/2013 | Bjornson et al. |
| 2013/0172239 A1 | 7/2013 | Gao et al. |
| 2013/0177530 A1 | 7/2013 | Bacon et al. |
| 2013/0243726 A1 | 9/2013 | Ray et al. |
| 2013/0273005 A1 | 10/2013 | Delaney et al. |
| 2013/0288997 A1 | 10/2013 | Ross et al. |
| 2013/0309196 A1 | 11/2013 | Bacon et al. |
| 2013/0310551 A1 | 11/2013 | Ross et al. |
| 2013/0315866 A1 | 11/2013 | Parsy et al. |
| 2013/0324496 A1 | 12/2013 | Scott et al. |
| 2013/0324740 A1 | 12/2013 | Scott et al. |
| 2014/0018313 A1 | 1/2014 | Bacon et al. |
| 2014/0039021 A1 | 2/2014 | Bacon et al. |
| 2014/0045783 A1 | 2/2014 | Du et al. |
| 2014/0051656 A1 | 2/2014 | Guo et al. |
| 2014/0051749 A1 | 2/2014 | Hashash et al. |
| 2014/0112885 A1 | 4/2014 | Bacon et al. |
| 2014/0178336 A1 | 6/2014 | Link et al. |
| 2014/0187511 A1 | 7/2014 | Du et al. |
| 2014/0212491 A1 | 7/2014 | Chal et al. |
| 2014/0213751 A1 | 7/2014 | Fukuzaki et al. |
| 2014/0249074 A1 | 9/2014 | Bacon et al. |
| 2014/0309187 A1 | 10/2014 | Hashash et al. |
| 2014/0309432 A1 | 10/2014 | Bacon et al. |
| 2014/0316144 A1 | 10/2014 | Bacon et al. |
| 2014/0323395 A1 | 10/2014 | Bernstein et al. |
| 2015/0064252 A1 | 3/2015 | Gorman et al. |
| 2015/0064253 A1 | 3/2015 | Gorman et al. |
| 2015/0141326 A1 | 5/2015 | Bacon et al. |
| 2015/0141353 A1 | 5/2015 | Delaney, IV et al. |
| 2015/0232453 A1 | 8/2015 | Scott et al. |
| 2015/0299213 A1 | 10/2015 | Bacon et al. |
| 2015/0353529 A1 | 12/2015 | Bacon et al. |
| 2016/0083394 A1 | 3/2016 | Bacon et al. |
| 2016/0083395 A1 | 3/2016 | Link et al. |
| 2016/0115175 A1 | 4/2016 | Bacon et al. |
| 2016/0362416 A1 | 12/2016 | Link et al. |
| 2017/0095499 A1 | 4/2017 | Gorman et al. |
| 2018/0000855 A1 | 1/2018 | Du et al. |
| 2018/0186806 A1 | 7/2018 | Bacon et al. |
| 2019/0240246 A1 | 8/2019 | Gorman et al. |
| 2020/0071337 A1 | 3/2020 | Bacon et al. |

FOREIGN PATENT DOCUMENTS

| | | |
|---|---|---|
| CN | 101108870 | 1/2008 |
| CN | 100457776 | 2/2009 |
| CN | 101754966 | 6/2010 |
| DE | 19914474 | 10/1999 |
| EP | 0180276 | 5/1986 |
| EP | 0350287 | 1/1990 |
| EP | 0901786 | 3/1999 |
| EP | 1027886 | 8/2000 |
| EP | 1828217 | 9/2007 |
| EP | 1881001 | 1/2008 |
| EP | 2097430 | 9/2009 |
| EP | 2124555 | 12/2009 |
| EP | 2207786 | 3/2012 |
| EP | 2583677 | 4/2013 |
| JP | 5-238939 | 9/1993 |
| JP | 2007-505742 | 3/2007 |
| JP | 2011-511837 | 4/2011 |
| JP | 2011-511840 | 4/2011 |
| JP | 2016-051146 | 4/2016 |
| WO | WO-89/02733 | 4/1989 |
| WO | WO-90/00555 | 1/1990 |
| WO | WO-91/16920 | 11/1991 |
| WO | WO-91/18914 | 12/1991 |
| WO | WO-91/019721 | 12/1991 |
| WO | WO-93/00910 | 1/1993 |
| WO | WO-94/26273 | 11/1994 |
| WO | WO-95/13090 | 5/1995 |
| WO | WO-95/24185 | 9/1995 |
| WO | WO-96/15132 | 5/1996 |
| WO | WO-96/29336 | 9/1996 |
| WO | WO-96/32403 | 10/1996 |
| WO | WO-97/12033 | 4/1997 |
| WO | WO-97/36554 | 10/1997 |
| WO | WO-98/16184 | 4/1998 |
| WO | WO-98/17679 | 4/1998 |
| WO | WO-98/22496 | 5/1998 |
| WO | WO-99/07734 | 2/1999 |
| WO | WO-99/15194 | 4/1999 |
| WO | WO-99/32139 | 7/1999 |
| WO | WO-99/32140 | 7/1999 |
| WO | WO-99/37753 | 7/1999 |
| WO | WO-99/43691 | 9/1999 |
| WO | WO-99/59621 | 11/1999 |
| WO | WO-99/64016 | 12/1999 |
| WO | WO-00/06529 | 2/2000 |
| WO | WO-00/09531 | 2/2000 |
| WO | WO-00/37110 | 6/2000 |
| WO | WO-01/07454 | 2/2001 |
| WO | WO-01/32153 | 5/2001 |
| WO | WO-01/60315 | 8/2001 |
| WO | WO-01/79246 | 10/2001 |
| WO | WO-01/81359 | 11/2001 |
| WO | WO-01/90121 | 11/2001 |
| WO | WO-01/91737 | 12/2001 |
| WO | WO-01/92282 | 12/2001 |
| WO | WO-01/96353 | 12/2001 |
| WO | WO-02/08187 | 1/2002 |
| WO | WO-02/08198 | 1/2002 |
| WO | WO-02/08241 | 1/2002 |
| WO | WO-02/08251 | 1/2002 |
| WO | WO-02/08256 | 1/2002 |
| WO | WO-02/18404 | 3/2002 |
| WO | WO-02/32414 | 4/2002 |
| WO | WO-02/32920 | 4/2002 |
| WO | WO-02/48116 | 6/2002 |
| WO | WO-02/48157 | 6/2002 |
| WO | WO-02/48165 | 6/2002 |
| WO | WO-02/48172 | 6/2002 |
| WO | WO-02/057287 | 7/2002 |
| WO | WO-02/057425 | 7/2002 |
| WO | WO-02/060926 | 8/2002 |
| WO | WO-02/100415 | 12/2002 |
| WO | WO-03/000713 | 1/2003 |
| WO | WO-03/006490 | 1/2003 |
| WO | WO-03/007945 | 1/2003 |
| WO | WO-03/010141 | 2/2003 |
| WO | WO-03/024461 | 3/2003 |
| WO | WO-03/026589 | 4/2003 |
| WO | WO-03/037895 | 5/2003 |
| WO | WO-03/051899 | 6/2003 |
| WO | WO-03/053989 | 7/2003 |
| WO | WO-03/061576 | 7/2003 |
| WO | WO-03/062256 | 7/2003 |
| WO | WO-03/064456 | 8/2003 |
| WO | WO-03/068244 | 8/2003 |

(56) References Cited

FOREIGN PATENT DOCUMENTS

| | | |
|---|---|---|
| WO | WO-03/101993 | 12/2003 |
| WO | WO-03/104250 | 12/2003 |
| WO | WO-03/105770 | 12/2003 |
| WO | WO-03/106477 | 12/2003 |
| WO | WO-2004/000858 | 12/2003 |
| WO | WO-2004/002422 | 1/2004 |
| WO | WO-2004/002940 | 1/2004 |
| WO | WO-2004/002944 | 1/2004 |
| WO | WO-2004/002977 | 1/2004 |
| WO | WO-2004/002999 | 1/2004 |
| WO | WO-2004/003000 | 1/2004 |
| WO | WO-2004/003138 | 1/2004 |
| WO | WO-2004/007512 | 1/2004 |
| WO | WO-2004/009020 | 1/2004 |
| WO | WO-2004/009610 | 1/2004 |
| WO | WO-2004/011478 | 2/2004 |
| WO | WO-2004/014313 | 2/2004 |
| WO | WO-2004/014852 | 2/2004 |
| WO | WO-2004/035571 | 4/2004 |
| WO | WO-2004/041201 | 5/2004 |
| WO | WO-2004/046331 | 6/2004 |
| WO | WO-2004/065367 | 8/2004 |
| WO | WO-2004/080466 | 9/2004 |
| WO | WO-2004/094452 | 11/2004 |
| WO | WO-2004/096210 | 11/2004 |
| WO | WO-2004/096234 | 11/2004 |
| WO | WO-2004/096235 | 11/2004 |
| WO | WO-2004/096286 | 11/2004 |
| WO | WO-2004/099241 | 11/2004 |
| WO | WO-2004/106356 | 12/2004 |
| WO | WO-2005/002626 | 1/2005 |
| WO | WO-2005/003147 | 1/2005 |
| WO | WO-2005/007810 | 1/2005 |
| WO | WO-2005/009418 | 2/2005 |
| WO | WO-2005/012327 | 2/2005 |
| WO | WO-2005/020884 | 3/2005 |
| WO | WO-2005/021568 | 3/2005 |
| WO | WO-2005/028502 | 3/2005 |
| WO | WO-2005/030891 | 4/2005 |
| WO | WO-2005/037214 | 4/2005 |
| WO | WO-2005/067900 | 7/2005 |
| WO | WO-2005/072361 | 8/2005 |
| WO | WO-2005/082144 | 9/2005 |
| WO | WO-2005/082880 | 9/2005 |
| WO | WO-2005/087788 | 9/2005 |
| WO | WO-2005/095403 | 10/2005 |
| WO | WO-2005/103045 | 11/2005 |
| WO | WO-2005/123076 | 12/2005 |
| WO | WO-2005/123087 | 12/2005 |
| WO | WO-2006/000922 | 1/2006 |
| WO | WO-2006/012078 | 2/2006 |
| WO | WO-2006/012440 | 2/2006 |
| WO | WO-2006/020082 | 2/2006 |
| WO | WO-2006/029081 | 3/2006 |
| WO | WO-2006/031725 | 3/2006 |
| WO | WO-2006/035061 | 4/2006 |
| WO | WO-2006/037028 | 4/2006 |
| WO | WO-2006/050161 | 5/2006 |
| WO | WO-2006/063149 | 6/2006 |
| WO | WO-2006/063717 | 6/2006 |
| WO | WO-2006/065335 | 6/2006 |
| WO | WO-2006/065590 | 6/2006 |
| WO | WO-2006/067606 | 6/2006 |
| WO | WO-2006/093801 | 9/2006 |
| WO | WO-2006/100310 | 9/2006 |
| WO | WO-2006/116557 | 11/2006 |
| WO | WO-2006/120251 | 11/2006 |
| WO | WO-2006/120252 | 11/2006 |
| WO | WO-2006/121820 | 11/2006 |
| WO | WO-2006/133326 | 12/2006 |
| WO | WO-2007/002602 | 1/2007 |
| WO | WO-2007/014920 | 2/2007 |
| WO | WO-2007/014921 | 2/2007 |
| WO | WO-2007/014922 | 2/2007 |
| WO | WO-2007/014925 | 2/2007 |
| WO | WO-2007/014926 | 2/2007 |
| WO | WO-2007/015824 | 2/2007 |
| WO | WO-2007/020193 | 2/2007 |
| WO | WO-2007/027248 | 3/2007 |
| WO | WO-2007/039142 | 4/2007 |
| WO | WO-2007/039145 | 4/2007 |
| WO | WO-2007/065829 | 6/2007 |
| WO | WO-2007/070556 | 6/2007 |
| WO | WO-2007/076034 | 7/2007 |
| WO | WO-2007/088148 | 8/2007 |
| WO | WO-2007/092000 | 8/2007 |
| WO | WO-2007/093901 | 8/2007 |
| WO | WO-2007/095269 | 8/2007 |
| WO | WO-2007/109604 | 9/2007 |
| WO | WO-2008/010921 | 1/2008 |
| WO | WO-2008/021927 | 2/2008 |
| WO | WO-2008/021928 | 2/2008 |
| WO | WO-2008/021936 | 2/2008 |
| WO | WO-2008/045419 | 4/2008 |
| WO | WO-2008/048128 | 4/2008 |
| WO | WO-2008/062206 | 5/2008 |
| WO | WO-2008/079206 | 7/2008 |
| WO | WO-2008/082601 | 7/2008 |
| WO | WO-2008/085508 | 7/2008 |
| WO | WO-2008/121634 | 10/2008 |
| WO | WO-2008/142055 | 11/2008 |
| WO | WO-2008/144380 | 11/2008 |
| WO | WO-2009/020825 | 2/2009 |
| WO | WO-2009/020828 | 2/2009 |
| WO | WO-2009/050289 | 4/2009 |
| WO | WO-2009/052287 | 4/2009 |
| WO | WO-2009/102318 | 8/2009 |
| WO | WO-2009/102325 | 8/2009 |
| WO | WO-2009/102568 | 8/2009 |
| WO | WO-2009/102633 | 8/2009 |
| WO | WO-2009/115893 | 9/2009 |
| WO | WO-2009/120878 | 10/2009 |
| WO | WO-2009/129120 | 10/2009 |
| WO | WO-2009/152095 | 12/2009 |
| WO | WO-2010/004343 | 1/2010 |
| WO | WO-2010/009121 | 1/2010 |
| WO | WO-2010/017401 | 2/2010 |
| WO | WO-2010/017432 | 2/2010 |
| WO | WO-2010/042834 | 4/2010 |
| WO | WO-2010/062821 | 6/2010 |
| WO | WO-2010/065668 | 6/2010 |
| WO | WO-2010/065674 | 6/2010 |
| WO | WO-2010/065681 | 6/2010 |
| WO | WO-2010/075554 | 7/2010 |
| WO | WO-2010/080878 | 7/2010 |
| WO | WO-2010/091413 | 8/2010 |
| WO | WO-2010/094977 | 8/2010 |
| WO | WO-2010/096302 | 8/2010 |
| WO | WO-2010/096462 | 8/2010 |
| WO | WO-2010/096777 | 8/2010 |
| WO | WO-2010/097229 | 9/2010 |
| WO | WO-2010/099527 | 9/2010 |
| WO | WO-2010/111483 | 9/2010 |
| WO | WO-2010/111534 | 9/2010 |
| WO | WO-2010/111673 | 9/2010 |
| WO | WO-2010/117635 | 10/2010 |
| WO | WO-2010/117977 | 10/2010 |
| WO | WO-2010/120621 | 10/2010 |
| WO | WO-2010/120935 | 10/2010 |
| WO | WO-2010/122162 | 10/2010 |
| WO | WO-2010/132538 | 11/2010 |
| WO | WO-2010/132601 | 11/2010 |
| WO | WO-2010/135569 | 11/2010 |
| WO | WO-2010/138368 | 12/2010 |
| WO | WO-2010/138488 | 12/2010 |
| WO | WO-2010/138790 | 12/2010 |
| WO | WO-2010/138791 | 12/2010 |
| WO | WO-2010/144646 | 12/2010 |
| WO | WO-2010/148006 | 12/2010 |
| WO | WO-2011/004276 | 1/2011 |
| WO | WO-2011/009084 | 1/2011 |
| WO | WO-2011/015657 | 2/2011 |
| WO | WO-2011/015658 | 2/2011 |
| WO | WO-2011/026920 | 3/2011 |

(56) References Cited

FOREIGN PATENT DOCUMENTS

| WO | WO-2011/028596 | 3/2011 |
|---|---|---|
| WO | WO-2011/031904 | 3/2011 |
| WO | WO-2011/031934 | 3/2011 |
| WO | WO-2011/046811 | 4/2011 |
| WO | WO-2011/050146 | 4/2011 |
| WO | WO-2011/054834 | 5/2011 |
| WO | WO-2011/059850 | 5/2011 |
| WO | WO-2011/059887 | 5/2011 |
| WO | WO-2011/060000 | 5/2011 |
| WO | WO-2011/066241 | 6/2011 |
| WO | WO-2011/075439 | 6/2011 |
| WO | WO-2011/075607 | 6/2011 |
| WO | WO-2011/075615 | 6/2011 |
| WO | WO-2011/079327 | 6/2011 |
| WO | WO-2011/082077 | 7/2011 |
| WO | WO-2011/087740 | 7/2011 |
| WO | WO-2011/091446 | 7/2011 |
| WO | WO-2011/112429 | 9/2011 |
| WO | WO-2011/123645 | 10/2011 |
| WO | WO-2011/146401 | 11/2011 |
| WO | WO-2011/156578 | 12/2011 |
| WO | WO-2012/027712 | 3/2012 |
| WO | WO-2012/041014 | 4/2012 |
| WO | WO-2012/048421 | 4/2012 |
| WO | WO-2012/068234 | 5/2012 |
| WO | WO-2012/087976 | 6/2012 |
| WO | WO-2013/030135 | 3/2013 |
| WO | WO-2013/040492 | 3/2013 |
| WO | WO-2013/075029 | 5/2013 |
| WO | WO-2013/101550 | 7/2013 |
| WO | WO-2013/173488 | 11/2013 |
| WO | WO-2013/173492 | 11/2013 |
| WO | WO-2013/184698 | 12/2013 |
| WO | WO-2014/100500 | 6/2014 |
| WO | WO-2014/185995 | 11/2014 |
| WO | WO-2015/030853 | 3/2015 |
| WO | WO-2015/030854 | 3/2015 |
| WO | WO-2015/084741 | 6/2015 |
| WO | WO-2015/191431 | 12/2015 |
| WO | WO-2015/191437 | 12/2015 |

OTHER PUBLICATIONS

U.S. Appl. No. 60/392,351, filed Jun. 28, 2002, Gosselin et al.
U.S. Appl. No. 60/909,315, filed Mar. 30, 2007, Sofia et al.
U.S. Appl. No. 60/982,309, filed Oct. 24, 2007, Sofia et al.
U.S. Appl. No. 61/119,723, filed Dec. 3, 2008, Li et al.
U.S. Appl. No. 61/214,884, filed Sep. 30, 2010, Li et al.
U.S. Appl. No. 61/504,924, filed Jul. 6, 2011, Kato et al.
Abraham et al., Synthesis and Biological Activity of Aromatic Amino Acid Phosphoramidates of 5-Fluoro-2'-deoxyuridine and 1-β-Arabinofuranosylcytosine: Evidence of Phosphoramidase Activity, J. Med. Chem. 1996, vol. 39, No. 23, pp. 4569-4575.
Abraham et al., Synthesis, Biological Activity and Decomposition Studies of Amino Acid Phosphomonoester Amidates of Acyclovir, Nucleosides and Nucleotides (1997), 16:10-11, pp. 2079-2092.
Abstract 100 Perrone, presented at the Nineteenth International Conference on Antiviral Research, May 7-11, 2006.
Adam, et al., "On the temperature dependence of cooperative relaxation properties in glass-forming liquids," The Journal of Chemical Physics (1965), 43(1):139-146.
Adiwijaya, et al., "A Viral Dynamic Model for Treatment Regimens with Direct-acting Antivirals for Chronic Hepatitis C Infection," PLoS Computational Biology, (2012), 8(1), e1002339, pp. 1-11.
Angell, "Formation of Glasses from Liquids and Biopolymers," Science, Mar. 31, 1995; 267(5206):1924-1935.
Angell, "The old problems of glass and the glass transition, and the many new twists" Proc Natl Acad Sci USA., Jul. 18, 1995; 92(15):6675-6682.
Appel et al., "Mutational Analysis of Hepatitis C Virus Nonstructural Protein 5A: Potential Role of Differential Phosphorylation in RNA Replication and Identification of a Genetically Flexible Domain", Journal of Virology, 2005, pp. 3187-3194.
Aquaro et al., Activities of Masked 2',3'-Dideoxynucleoside Monophosphate Derivatives against Human Immunodeficiency Virus in Resting Macrophages, Antimicrobial Agents and Chemotherapy 2000; vol. 44, No. 1, pp. 173-177.
Arnold et al., Sensitivity of Mitochondrial Transcription and Resistance of RNA Polymerase II Dependent Nuclear Transcription to Antiviral Ribonucleosides, PLOS Pathogens (2012), 8(11): e1003030. doi.org/10.1371/journal.ppat.1003030, Epub Nov. 15, 2012.
Artursson, et al., "Caco-2 monolayers in experimental and theoretical predictions of drug transport," Advanced Drug Delivery Reviews (1996), 22:67-84.
Asif et al., Pharmacokinetics of the Antiviral Agent β-d-2'-Deoxy-2'-Fluoro-2'-C-Methylcytidine in Rhesus Monkeys, Antimicrobial Agents and Chemotherapy 2007, vol. 51, No. 8, pp. 2877-2882.
Asselah, "Daclatasvir plus sofosbuvir for HCV infection: An oral combination therapy with high antiviral efficacy," Journal of Hepatology, (2014), 61(2); 435-438.
Avdeef, A., "Physicochemical Profiling (Solubility, Permeability and Charge State)", Current Topics in Medicinal Chemistry 2001, pp. 277-351.
Bailey, et al., "The use of intestinal epithelial cell culture model, Caco-2, in pharmaceutical development," Advanced Drug Delivery Reviews (1996), 22:85-103.
Baird, et al., "A classification system to assess the crystallization tendency of organic molecules from undercooled melts," Journal of Pharmaceutical Sciences Sep. 2010; 99(9):3787-3806.
Balzarini et al., Mechanism of anti-HIV action of masked alaninyl d4T-MP derivatives, Proceedings of the National Academy of Sciences 1996, vol. 93, pp. 7295-7299.
Banker et al., Prodrugs, Modern Pharmaceuticals. 1996, Third Edition, Revised and Expanded, pp. 451 and 596.
Bartenschlager et al., Kinetic and structural analyses of hepatitis C virus polyprotein processing. Journal of Virology 1994, vol. 68, No. 8, pp. 5045-5055.
Bartenschlager et al., Nonstructural protein 3 of the hepatitis C virus encodes a serine-type proteinase required for cleavage at the NS3/4 and NS4/5 junctions. J Virol. 1993, vol. 67, No. 7, pp. 3835-3844.
Baschang et al., Neue derivate von thymidin-3',5'-cyclophosphat, Angew. Chem. 1973, vol. 85, No. 1, pp. 44-45, XP002599755.
BASF Pamphlet entitled "The right path to greater solubility and bioavailability. BASF excipients for solubilization," (2011) located at pharma-ingredients.basf.com/Documents/ENP/Brochure/EN/Brochure_Solubilizer.pdf.
Battaglia et al., Combination Therapy with Interferon and Ribavirin in the Treatment of Chronic Hepatitis C Infection, Annals of Pharmacotherapy 2000, vol. 34, No. 4, pp. 487-494.
Bazan et al., Detection of a trypsin-like serine protease domain in flaviviruses and pestiviruses. Virology 1989, vol. 171, pp. 637-639.
Beaulieu et al., Inhibitors of the HCV NS5B polymerase: new hope for the treatment of hepatitis C infections. Current Opinion in Investigational Drugs 2004, vol. 5, No. 8, pp. 838-850.
Behrens et al., Identification and properties of the RNA-dependent RNA polymerase of hepatitis C virus. The EMBO Journal 1996, vol. 15, No. 1, pp. 12-22.
Belema et al., CAPLUS 2010:175961, (2012).
Berenguer et al., Hepatitis C virus in the transplant setting. Antiviral Therapy 1998, vol. 3, Supplement 3:125-136.
Beten, et al., "Controlled-release coevaporates of dipyridamole prepared with acrylic polymers," Intl J Pharmaceutics, (1994), 103(3): 243-251.
Bhat et al., Synthesis and Pharmacokinetic Properties of Nucleoside Analogues as Possible Inhibitors of HCV RNA Replication, (Oral Session V: Hepatitis C Virus, Flaviviruses), 16th International Conference on Antiviral Research, Abstract 120, p. A75. (Apr. 27-May 1, 2003).
BMS Press Release, "Bristol-Myers Squibb to Present New Data Demonstrating Company's Continuing Commitment to Research and Development in Liver Disease at the American Association for the Study of Liver Diseases (AASLD) Annual Meeting," Oct. 16, 2012.

(56) References Cited

OTHER PUBLICATIONS

BMS Press Release, "European Commission Approves Bristol-Myers Squibb's Daklinza (daclatasvir) Across Multiple Genotypes for the Treatment of Chronic Hepatitis C Infection," Aug. 27, 2014.
BMS Press Release, "Investigational Triple DAA Regimen of Daclatasvir, Asunaprevir and BMS-791325 Achieved SVR12 of 94% in Treatment-Naïve Patients with Genotype 1 Chronic Hepatitis C Infection in Phase II Trial," Nov. 12, 2012.
BMS Press Release, "New 12 Week, Interferon-Free Treatment Arms Added to All-Oral Combination Study of PSI-7977 and Daclatasvir (BMS-790052) for HCV Genotype 1," Nov. 4, 2011.
Borawski et al., "Class III Phosphatidylinositol 4-Kinase Alpha and Beta Are Novel Host Factor Regulators of Hepatitis C Virus Replication", Journal of Virology, 2009, pp. 10058-10074.
Breitenbach, "Melt extrusion can bring new benefits to HIV therapy," American Journal of Drug Delivery, (2006), 4(2): 61-64.
Broeders et al., a 400- and 600-MHz 1H NMR conformational study on nucleoside cyclic 3',5' Pv-TBP systems. Conformational transmission induces diequatorial orientation of the 3',5'-dioxaphosphorinane ring in a nonchair conformation, J. Am. Chem. Soc. 1990, vol. 112, No. 21, pp. 7475-7482, XP002599754.
Brunton et al., Goodman & Gilman's the Pharmacological Basis of Therapeutics, 11th edition, McGraw-Hill 2006, 4103-4105, lines 1-7.
Butler, et al., "The developability classification system: application of biopharmaceutics concepts to formulation development," Journal of Pharmaceutical Sciences Dec. 2010; 99(12):4940-4954.
Cahard et al., Aryloxy phosphoramidate triesters as pro-tides. Mini-Reviews in Medicinal Chemistry 2004, vol. 4, No. 4, pp. 371-381.
Caira, M.R., Crystalline Polymorphism of Organic Compounds, Topics in Current Chemistry, vol. 198, pp. 163-208, Springer Verlag Berlin Heidelberg 1998.
Calisher et al., Antigenic relationships between flaviviruses as determined by cross-neutralization tests with polyclonal antisera. J Gen Virol. 1989, vol. 70, pp. 37-43.
Carroll et al., Nucleoside Analog Inhibitors of Hepatitis C Virus Replication. Infectious Disorders, Drug Targets. 2006, vol. 6, No. 1, pp. 17-29.
Chang et al., Amino Acid Phosphoramidate Monoesters of 3'-Azido-3'-deoxythymidine: Relationship between Antiviral Potency and Intracellular Metabolism, J. Med. Chem. 2001, vol. 44, No. 2, pp. 223-231.
Chang et al., Deoxycytidine deaminase-resistant stereoisomer is the active form of (+/−)-2',3'-dideoxy-3'-thiacytidine in the inhibition of hepatitis B virus replication. The Journal of Biological Chemistry 1992, vol. 267, No. 20, pp. 13938-13942.
Chapman et al., Practical Synthesis, Separation, and Stereochemical Assignment of the PMPA Pro-Drug GS-7340, Nucleosides, Nucleotides & Nucleic Acids 2001, vol. 20, No. 4-7, pp. 621-628.
Chapman et al., Purification of PMPA Amidate Prodrugs by SMB Chromatography and X-Ray Crystallography of the Diastereomerically Pure GS-7340, Nucleosides, Nucleotides & Nucleic Acids 2001, vol. 20, No. 4-7, pp. 1085-1090.
Chatel-Chaix et al., Hepatitis C Virus NS3/4A Protease Inhibitors: A Light at the End of the Tunnel, Viruses 2010, 2, pp. 1752-1765; doi:10.3390/v2081752.
Chemical Abstracts Registry No. 1256391-55-5, indexed in the Registry file on STN ACS Online, Dec. 13, 2010.
Chen et al., In Vivo Pharmacokinetics and Metabolism of Anti-Human Immunodeficiency Virus Agent d4T-5'-[p-Bromophenyl Methoxyalaninyl Phosphate] (SAMPIDINE) in Mice, Drug Metabolism and Disposition 2001, vol. 29, No. 7, pp. 1035-1041.
Chen et al., Metabolism of Stavudine-5'-[p-Bromophenyl Methoxyalaninyl Phosphate], Stampidine, in Mice, Dogs, and Cats, Drug Metabolism and Disposition 2002, vol. 30, No. 12, pp. 1523-1531.
Cheng, et al., "Antiviral Activity and Resistance Profile of the Novel HCV NS5A Inhibitor GS-5885", presentation at EASL Barcelona, Spain, Apr. 18-22, 2012.

Chiou, et al., "Pharmaceutical Applications of Solid Dispersion Systems," J Pharm Sci, (1971), 60(9):1281-1302.
Chiou et al., "Crystallization of Amorphous Components in Spray-Dried Powders", Drying Technology, 25, pp. 1427-1435, 2007, Taylor & Francis.
Chou et al., Evidence that Human Histidine Triad Nucleotide Binding Protein 3 (Hint3) is a Distinct Branch of the Histidine Triad (HIT) Superfamily, J. Mol. Biol. 2007, vol. 373, pp. 978-989.
Chou et al., Phosphoramidate Pronucleotides: A Comparison of the Phosphoramidase Substrate Specificity of Human and *Escherichia coli* Histidine Triad Nucleotide Binding Proteins, Molecular Pharmaceutics 2007, vol. 4, No. 2, pp. 208-217.
Chu et al., Isolation and structure of SCH 351633: a novel hepatitis C virus (HCV) NS3 protease inhibitor from the fungus *Penicillium griseofulvum*, Bioorganic & Medicinal Chemistry Letters 1999, vol. 9, pp. 1949-1952.
Chu et al., Structure of Sch 68631: A new hepatitis C virus proteinase inhibitor from *Streptomyces* sp. Tetrahedron Letters 1996, vol. 37, No. 40, pp. 7229-7232.
Chung, et al., "Highlights of AASLD 2011, CCO Official Conference Coverage of the 2011 Annual Meeting of the American Association for the Study of Liver Diseases," Nov. 4-8, 2011, San Francisco, California.
Cihlar et al., Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131, Antimicrobial Agents and Chemotherapy 2008, vol. 52, No. 2, pp. 655-665.
Clark et al., Design, Synthesis, and Antiviral Activity of 2'-Deoxy-2'-fluoro-2'-C-methylcytidine, a Potent Inhibitor of Hepatitis C Virus Replication, J. Med. Chem. 2005, vol. 48, No. 17, pp. 5504-5508.
Clark et al., Synthesis and antiviral activity of 2'-deoxy-2'-fluoro-2'-C-methyl purine nucleosides as inhibitors of hepatitis C virus RNA replication, Bioorganic & Medicinal Chemistry Letters 2006 vol. 16, No. 6, pp. 1712-1715.
Clayden, et al., Organic Chemistry—Oxford University Press 2005, cover page and pp. 48-49.
Clinical Trial NCT02133131, MK-5172+MK-8742+sofosbuvir for 4-8 weeks, HCV Genotype 1 patients, Aug. 26, 2014.
Clinical Trial NCT02226549, 5885+7977+vedroprevir +/− ribavirin for 8 weeks, HCV Genotype 1 patients, Aug. 26, 2014.
ClinicalTrials NCT01455090, BMS-650032, BMS-790052, and BMS-791325 for 12 weeks, (2011).
ClinicalTrials NCT01826981, GS-9669, GS-5885/GS-7977 for 12 weeks, HCV genotype 1 patients, (2013).
ClinicalTrials NCT01858766 on Jul. 22, 2013. clinicaltrials.gov/archive/NCT01858766/2013_07_22.
ClinicalTrials NCT02098616, Asunaprevir +Daclatasvir + BMS-791325 ± Ribavirin for 8 weeks, (2014).
Codington et al. Nucleosides. XVIII. Synthesis of 2'-Fluorothymidine, 2'-Fluorodeoxyuridine, and Other 2'-Halogeno-2'-Deoxy Nucleosides1,2. The Division of Nucleoprotein Chemistry, Sloan-Kettering Institute for Cancer Research, Sloan-Kettering Division of Cornell University Medical College, New York, 21, New York, 1964, vol. 29, pp, 558-564.
Cole et al., R-7128: RNA-directed RNA polymerase (NS5B) inhibitor treatment of hepatitis C virus infection, Drugs of the Future 2009, 34(4):282-290.
Congiatu et al., (2007) Molecular Modelling Studies on the Binding of Some Protides to the Putative Human Phosphoramidase Hint1, Nucleosides, Nucleotides & Nucleic Acids, vol. 26, pp. 1121-1124.
Congiatu et al., (2005) Naphthyl Phosphoramidate Derivatives of BVdU as Potential Anticancer Agents: Design, Synthesis and Biological Evaluation, Nucleosides, Nucleotides & Nucleic Acids, vol. 24, No. 5-7, pp. 485-489.
Congiatu et al., Novel Potential Anticancer Naphthyl Phosphoramidates of BVdU: Separation of Diastereoisomers and Assignment of the Absolute Configuration of the Phosphorus Center. J. Med. Chem. 2006, vol. 49, No. 2, pp. 452-455.

(56) References Cited

OTHER PUBLICATIONS

Curley et al., Synthesis and anti-HIV evaluation of some phosphoramidate derivatives of AZT: studies on the effect of chain elongation on biological activity. Antiviral Research 1990, vol. 14, pp. 345-356.
Crowley, et al., "The use of thermal methods for predicting glass-former fragility," *Thermochimica Acta*, (2001), 380:79-93.
Curry et al., Sofosbuvir and Ribavirin Prevent Recurrence of HCV Infection After Liver Transplantation: An Open-Label Study, Gastroenterology 2015; vol. 148, No. 1, pp. 100-107.
Custodio, et al., "Predicting drug disposition, absorption/elimination/transporter interplay and the role of food on drug absorption," Advanced Drug Delivery Reviews Mar. 17, 2008; 60(6):717-733.
Dahan, et al., "Prediction of solubility and permeability class membership: provisional BCS classification of the world's top oral drugs," AAPS Journal 2009, 11(4): 740-746.
Dahari, et al., "Triphasic Decline of Hepatitis C Virus RNA During Antiviral Therapy," *Hepatology*, (2007), 46(1): 16-21.
Das, et al., CAPLUS 2011:1236910, (2012).
Davis, G. L., Current Therapy for Chronic Hepatitis C, Gastroenterology 2000, vol. 118, No. 2, pp. S104-S114.
D'Cruz et al., Stampidine: a selective oculo-genital microbicide. Journal of Antimicrobial Chemotherapy 2005, vol. 56, pp. 10-19.
De Francesco et al., Challenges and successes in developing new therapies for hepatitis C. Nature 2005, vol. 436, pp. 953-960.
De Lombaert et al., N-Phosphonomethyl Dipeptides and Their Phosphonate Prodrugs, a New Generation of Neutral Endopeptidase (NEP, EC 3.4.24.11) Inhibitors, J. Med. Chem. 1994, vol. 37 No. 4, pp. 498-511.
Delaney IV, W.E., "HBV & HCV: Parallels, Contrasts and Future Directions for Therapy," slides for presentation in the 25th ICAR (International Conference on Antiviral Research) presented on Apr. 18, 2012.
Detailed information of ABT-450 in Nihon Kagakubusshitsu Jisho located at nikkajiweb.jst.go.jp/nikkaji_web/pages/top.jsp.
Dixit, et al., "Modelling how ribavirin improves interferon response rates in hepatitis C virus infection," *Nature*, (2004) 432: 922-924.
Dressman, et al., "Mixing-tank model for predicting dissolution rate control of oral absorption." Journal of Pharmaceutical Sciences 1986, 75(2), pp. 109-116.
Drontle et al., (2004). Designing a Pronucleotide Stratagem: Lessons from Amino Acid Phosphoramidates of Anticancer and Antiviral Pyrimidines. Mini-Reviews in Medicinal Chemistry, vol. 4, No. 4, pp. 409-419.
Dumez et al., "Large-Scale Synthesis and Formulation of GMP-Grade Stampidine, A New Anti-HIV Agent," Arzneim.-Forsch./Drug Res. (2006) 56(2a), pp. 136-151.
Dykens et al., Strategies to reduce late-stage drug attrition due to mitochondrial toxicity, Expert Rev. Mol. Diagn. 2007, 7(2), pp. 161-175.
Earnings Call Transcript of Gilead Sciences Management Discusses Q1 2012 Results on Apr. 26, 2012.
Eckart et al., The Hepatitis C Virus Encodes a Serine Protease Involved in Processing of the Putative Nonstructural Proteins from the Viral Polyprotein Precursor. Biochemical and Biophysical Research Communications 1993, vol. 192, No. 2, pp. 399-406.
Edmundson et al., "Cyclic Organophosphorus Compounds. Part 23. Configurational Assignments in the 4-Phenyl-1,3,2-dioxaphosphorinane Series. X-Ray Molecular Structure of cis2 Benzylamino-4-phenyl-1,3,2-dioxaphosphorinane 2-oxide," J. Chem. Research (S) 1989, pp. 122-123.
Egan, et al., "Prediction of intestinal permeability," *Adv Drug Deliv Rev.*, Mar. 31, 2002;54(3):273-289.
Egron et al., S-Acyl-2-thioethyl Phosphoramidate Diester Derivatives as Mononucleotide Prodrugs. J. Med. Chem. 2003, vol. 46, No. 21, pp. 4564-4571.
Eisenberg et al., Metabolism of GS-7340, a novel phenyl monophosphoramidate intracellular prodrug of PMPA, in blood. Nucleosides Nucleotides & Nucleic Acids 2001, vol. 20, No. 4-7, pp. 1091-1098.
Elazar et al., "Amphipathic Helix-Dependent Localization of NS5A Mediates Hepatitis C Virus RNA Replication", Journal of Virology, 2003, pp. 6055-6061.
Eldrup et al., Oral Session V, Hepatitis C Virus, Flaviviridae. Program and Abstracts, The Sixteenth International Conference on Antiviral Research, Apr. 27-May 1, 2003, p. A75.
Eldrup et al., Structure—Activity Relationship of Purine Ribonucleosides for Inhibition of Hepatitis C Virus RNA-Dependent RNA Polymerase, J. Med. Chem. 2004, vol. 47, No. 9, pp. 2283-2295.
EMA Press release. European Medicines Agency recommends approval of sofosbuvir for the treatment of chronic hepatitis C, Nov. 22, 2013.
Engels et al., Cyclophosphate, III. Synthese und Eigenschaften von Uridin-3',5'-cyclophosphat-estern. Chemische Berichte 1977, vol. 110, No. 6, pp. 2019-2027. XP-002599753.
Evans et al., "Phosphorylation of hepatitis C virus nonstructural protein 5A modulates its protein interactions and viral RNA replication", PNAS, 2004, 101(35), pp. 13038-13043.
Exam Report for New Zealand Application No. 733275 dated Jun. 18, 2019. (2 pages).
Examination Report for Australian Patent Application No. 2017276223 dated Dec. 3, 2018. (2 pages).
Examination Report for Australian Patent Application No. 2014311827 dated Sep. 6, 2016. (2 pages).
Examination Report for European Application No. 14704501.7 dated Jun. 14, 2017. (5 pages).
Examination Report for European Patent Application No. 14704501.7 dated Sep. 25, 2018. 4 pages.
Examination Report for Gulf Cooperation Council Application No. 2014/26352 dated Apr. 25, 2017. (3 pages).
Examination Report for Gulf Cooperation Council Application No. 2014/26352 dated Aug. 29, 2018 (3 pages).
Examination Report for New Zealand Application No. 716840 dated Jun. 29, 2016. (3 pages).
Extended European Search Report for European Application No. 15156617.1 dated Jun. 19, 2015. (6 pages).
Extended European Search Report for European Application No. 18175400.3 dated Oct. 10, 2018. (8 pages).
Extended European Search Report for European Application No. 14151876.1 dated Sep. 18, 2014.
Extended European Search Report for European Application No. 14169060.2 dated Oct. 10, 2014.
Extended European Search Report for European Application No. 19211345.4 dated Feb. 25, 2020. (6 pages).
Extended European Search Report includes the Supplementary European Search Report issued in European Application No. 05775359.2 dated Sep. 15, 2010. (10 pages).
Failla et al., Both NS3 and NS4A Are Required for Proteolytic Processing of Hepatitis C Virus Nonstructural Proteins. Journal of Virology 1994, vol. 68, No. 6, pp. 3753-3760.
Farquhar et al., Synthesis and biological evaluation of neutral derivatives of 5-fluoro-2'-deoxyuridine 5'-phosphate. J. Med. Chem. 1983, vol. 26, No. 8, pp. 1153-1158.
Farquhar et al., Synthesis and biological evaluation of 9-[5'-(2-oxo-1,3,2-oxazaphosphorinan-2-yl)-β-D-arabinosyl]adenine and 9-[5'-(2-oxo-1,3,2-dioxaphosphorinan-2-yl)-β-D-arabinosyl]adenine: potential neutral precursors of 9-[β-D-arabinofuranosyl]adenine 5'-monophosphate. J. Med. Chem. 1985, vol. 28, No. 9, pp. 1358-1361.
FDA. Consumer Health Information leaflet, "Faster, Easier Cures for Hepatitis C". Jul. 2014.
FDA. Guidance for Industry Antiviral Product Development—Conducting and Submitting Virology Studies to the Agency. Clinical Antimicrobial, Jun. 2006.
Feng et al., Role of Mitochondrial RNA Polymerase in the Toxicity of Nucleotide Inhibitors of Hepatitis C Virus. Antimicrobial Agents and Chemotherapy 2016, vol. 60, No. 2, pp. 806-817.
Food-Effect Bioavailability and Fed Bioequivalence Studies, Guidance for Industry, published in 2002, available at https://www.fda.gov/OHRMS/DOCKETS/98fr/5194fnl.pdf. (12 pages).
FOURward Study (NCT02175966), Daclatasvir, Asunaprevir, BMS-791325 and Sofosbuvir for 4-12 weeks, HCV Genotype 1 treatment naïve patients, Jun. 25, 2014. ClinicalTrials.gov archive.

(56) References Cited

OTHER PUBLICATIONS

Freed et al., Evidence for acyloxymethyl esters of pyrimidine 5'-deoxyribonucleotides as extracellular sources of active 5'-deoxyribonucleotides in cultured cells. Biochemical Pharmacology 1989, vol. 38, pp. 3193-3198.
Freundt et al., "Interfering with interferons: Hepatitis C virus counters innate immunity", PNAS, 2005, 102(49), pp. 17539-17540.
Furman et al., Chapter 21 Discovery and Development of PSI-6130/RG7128. Antiviral Drugs: From Basic Discovery through Clinical Trials. First Edition 2011, pp. 305-315.
Furman et al. PSI-7851: A novel liver-targeting nucleotide prodrug for the treatment of hepatitis C. Poster, Presented at 59th Annual Meeting of the American Association for the Study of Liver Diseases, Oct. 31-Nov. 4, 2008; San Francisco, CA.
Furman et al., The Anti-Hepatitis B Virus Activities, Cytotoxicities, and Anabolic Profiles of the (−) and (+) Enantiomers of cis-5-Fluoro-1-[2-(Hydroxymethyl)-1,3-Oxathiolan-5-yl]Cytosine. Antimicrob Agents Chemother. 1992, vol. 36, No. 12, pp. 2686-2692.
Gane, "Future hepatitis C virus treatment: interferon-sparing combinations," *Liver International*, Jan. 2011; 1:62-67.
Gane, et al., "Mericitabine and ritonavir-boosted danoprevir with or without ribavirin in treatment-naive HCV genotype 1 patients: INFORM-SVR study," *Liver International*, Jan. 2015; 35(1):79-89.
Gane, et al., 34 "Once-daily PSI-7977 plus RBV: Pegylated interferon-alfa not required for Complete Rapid Viral Response in Treatment-Naïve Patients with HCV GT2 or GT3" (2011) *Hepatology* 54(4) 377A.
Gane et al., "Efficacy of Nucleotide Polymerase Inhibitor Sofosbuvir Plus the NS5A Inhibitor Ledipasvir or the NS5B Non-Nucleoside Inhibitor GS-9669 Against HCV Genotype 1 Infection", Gastroenterology, 2014; 146, pp. 736-743.
Gane et al., "Once Daily Sofosbuvir/Ledipasvir Fixed Dose Combination with or without Ribavirin: the ELECTRON trial", Hepatology, 2013, 58(4) (SUPPL), p. 243A.
Gao et al., "Chemical genetics strategy identifies an HCV NS5A inhibitor with a potent clinical effect", Nature, 2010, vol. 465, pp. 96-102.
Gao et al., "New BMS HCV NSSA Inhibitor: From Screen Hit to Clinic", natap.org/2008/HCV/101408, 2010, pp. 1-9.
Gastaminza et al., "Antiviral Stilbene 1,2-Diamines Prevent Initiation of Hepatitis C Virus RNA Replication at the Outset of Infection", Journal of Virology, 2011, vol. 85, pp. 5513-5523.
German et al., "Lack of a Clinically Significant Pharmacokinetic Drug-Drug Interaction between Sofosbuvir (GS-7977) and GS-5885 or GS-9669 in Healthy Volunteers", Hepatology, 56(4) (Suppl), 2012, pp. 1072A-1073A.
Gilead Sciences Press Release "European Medicines Agency Validates Gilead's Marketing Application for Ledipasvir/Sofosbuvir Fixed-Dose Combination Tablet for Genotype 1 Chronic Hepatitis C Infection", Mar. 27, 2014.
Gilead Sciences Press Release, "Gilead Announces U.S. FDA Priority Review Designation for Ledipasvir/Sofosbuvir Fixed-Dose Combination Tablet for Chronic Hepatitis C Genotype 1 Infection", Apr. 7, 2014.
Gilead Announces Interim Results Reported from ELECTRON and QUANTUM Studies, showing that HCV RNA could no longer be detected 4 weeks after treatment completed, Apr. 19, 2012.
Gillespie et al., Stereoselective Inhibition of Cholesterol Esterase by Enantiomeric Phosphonates. Phosphorus, Sulfur, and Silicon 1997, vol. 122, pp. 205-208.
Ghany et al., Diagnosis, management, and treatment of hepatitis C: An update. AASLD Practice Guidelines 2009. vol. 49, No. 4, pp. 1335-1374.
Glossary of Medical Education Terms, Institute for International Medical Education, www.iime.org/glossary.htm#P, Accessed in Mar. 2013. (23 pages).
Goekjian et al., Synthesis of Fluorinated Macrocyclic Bis(indolyl)maleimides as Potential $^{19}$F NMR Probes for Protein Kinase C. J. Org. Chem. 1999, vol. 64, No. 12, pp. 4238-4246.
Gorbalenya et al., A conserved NTP-motif in putative helicases. Nature 1988, vol. 333, p. 22.
Gorbalenya et al., N-terminal domains of putative helicases of flavi- and pestiviruses may be serine proteases. Nucleic Acids Research 1989, vol. 17, No. 10, pp. 3889-3897.
Graeser, et al., "Applying thermodynamic and kinetic parameters to predict the physical stability of two differently prepared amorphous forms of simvastatin," *Curr Drug Deliv.*, Aug. 2009; 6(4):374-382.
Graeser, et al., "Correlating thermodynamic and kinetic parameters with amorphous stability," *Eur J Pharm Sci*, Jun. 28, 2009;37(3-4):492-498.
Graeser, et al., "The role of configurational entropy in amorphous systems," *Pharmaceutics*, (2010), 2:224-244.
Grakoui et al., Characterization of the Hepatitis C Virus-Encoded Serine Proteinase: Determination of Proteinase-Dependent Polyprotein Cleavage Sites. Journal of Virology 1993, vol. 67, No. 5, pp. 2832-2843.
Grakoui et al., A second hepatitis C virus-encoded proteinase. Proc. Natl. Acad. Sci. 1993, vol. 90, pp. 10583-10587.
Griffith et al., HCV anti-viral agents. Annual Reports in Medicinal Chemistry 2004, vol. 39, pp. 223-237.
Gromova et al., Optical rotatory dispersion and circular dichroism of mono- and oligonucleotide-amino acids (amidates). Biochimica et Biophysica Acta 1971, vol. 240, No. 1, pp. 1-11.
Gudmundsson et al., Phosphoramidate Protides of Carbocyclic 2',3'-Dideoxy-2',3'-Didehydro-7-Deazaadenosine with Potent Activity Against HIV and HBV, Nucleosides, Nucleotides & Nucleic Acids 2004, vol. 23, No. 12, pp. 1929-1937.
Gudmundsson et al., Phosphoramidate Protides of 2',3'-Dideoxy-3'-fluoroadenosine and Related Nucleosides with Potent Activity Against HIV and HBV, Nucleosides, Nucleotides & Nucleic Acids 2003, vol. 22, No. 10, pp. 1953-1961.
Guedj, et al., "Second-Phase Hepatitis C Virus RNA Decline During Telaprevir-Based Therapy Increases With Drug Effectiveness: Implications for Treatment Duration," *Hepatology*, (2011) 53(6):1801-1808.
Guedj, et al., "Understanding hepatitis C viral dynamics with direct-acting antiviral agents due to the interplay between intracellular replication and cellular infection dynamics," *J Theor Biol*, (2010) 267:330-340.
Guillory, J.K., "Generation of Polymorphs, Hydrates, Solvates, and Amorphous Solids", Polymorphism in Pharmaceutical Solids, 1999.
Gunic et al., 6-Hydrazinopurine 2'-methyl ribonucleosides and their 5'-monophosphate prodrugs as potent hepatitis C virus inhibitors. Bioorganic & Medicinal Chemistry Letters 17 (2007), pp. 2456-2458.
Gunic et al., Cyclic monophosphate prodrugs of base-modified 2'-C-methyl ribonucleosides as potent inhibitors of hepatitis C virus RNA replication. Bioorganic & Medicinal Chemistry Letters 17, 2007, pp. 2452-2455.
Halstead, S. B., "Selective Primary Health Care: Strategies for Control of Disease in the Developing World. XI. Dengue," Reviews of Infectious Diseases 1984, vol. 6, No. 2, pp. 251-263.
Halstead, S. B., Pathogenesis of Dengue: Challenges to Molecular Biology. Science 1988, vol. 239, pp. 476-481.
Hancock, et al., "Molecular mobility of amorphous pharmaceuticals determined using differential scanning calorimetry," *Thermochimica Acta*, (2001), 380: 95-107.
Harris et al., Synthesis and Antiviral Evaluation of Phosphoramidate Derivatives of (E)-5-(2-Bromovinyl)-2'-Deoxyuridine. Antiviral Chemistry and Chemotherapy 2001, vol. 12, No. 5, pp. 293-300.
Hernández et al., Synthesis of Highly Functionalized Chiral Nitriles by Radical Fragmentation of β-Hydroxy Azides. Convenient Transformation of Aldononitriles into 1,4- and 1,5-Iminoalditols. J. Org. Chem. 2004, vol. 69, No. 24, pp. 8437-8444.
Hertel et al., Synthesis of 2-deoxy-2,2-difluoro-D-ribose and 2-deoxy-2,2'-difluoro-D-ribofuranosyl nucleosides. J. Org. Chem. 1988, vol. 53, No. 11, pp. 2406-2409.
Hézode, "Oral combination therapy: Future hepatitis C virus treatment?" *Journal of Hepatology*, (2011) 55:933-935.

(56) References Cited

OTHER PUBLICATIONS

Hijikata et al., Two Distinct Proteinase Activities Required for the Processing of a Putative Nonstructural Precursor Protein of Hepatitis C Virus. Journal of Virology 1993, vol. 67, No. 8, pp. 4665-4675.
Hilfiker et al., "Relevance of Solid-state Properties for Pharmaceutical Products", Wiley, 2006, pp. 1-19.
Hodge, "Adam-Gibbs formulation of enthalpy relaxation near the glass transition," *J Res Natl Inst Stand Technol.*, (1997), 102(2): 195-205.
Hostetler et al., Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine. Antimicrobial Agents and Chemotherapy 1992, vol. 36, No. 9, pp. 2025-2029.
Hostetler et al., Synthesis and Antiretroviral Activity of Phospholipid Analogs of Azidothymidine and Other Antiviral Nucleosides. The Journal of Biological Chemistry 1990, vol. 265, No. 11, pp. 6112-6117.
Howes et al., The Regiospecific One-Pot Phosphorylation of Either the 5'- or 2'-Hydroxyl in 3'Deoxycytidines Without Protection: Critical Role of the Base. Nucleosides, Nucleotides & Nucleic Acids 2003, vol. 22, Nos. 5-8, pp. 687-689.
Hrebabecky et al., 1-(3,5-O-Alkylidene-2-deoxy-4-C-hydroxymethyl-α-L-threo-pentofuranosyl)uracils. Collect. Czech. Chem. Commun. 1997, vol. 62, pp. 957-970.
Hrebabecky et al., Synthesis of 1-(3-Azido-2,3-dideoxy-β-D-ribo-hexofuranosyl)-, 1-(2,3-Dideoxy-β-D-erythro-hexofuranosyl)- and 1-(2,3-Dideoxy-β-D-erythro-hex-2-enofuranosyl)pyrimidine Nucleosides. Collect. Czech. Chem. Commun. 1994, vol. 59, pp. 412-420.
Hrebabecky et al., Synthesis of 1-(3-Azido-2,3-dideoxy-4-C-hydroxymethyl-α-L-threo-pentofuranosyl)thymine, 1-(2,3-Dideoxy-4-C-hydroxymethyl-α-L-glycero-pentofuranosyl)thymine and 1-(2,3-Dideoxy-4-C-hydroxymethyl-α-L-glycero-pent-2-enofuranosyl)thymine. Collect. Czech. Chem. Commun. 1993, 58, pp. 409-420.
Hrebabecky et al., Synthesis of 1-(3-azido-2,3-dideoxy-β-D-allofuranosyl)thymine, 1-(2,3-dideoxy-β-D-allofuranosyl)thymine, and 1-(2,3-dideoxy-β-D-erythro-hex-2-enofuranosyl)thymine. Carbohydrate Research 1991, vol. 216, pp. 179-186.
Huang et al., "Phosphorylation of hepatitis C virus NS5A nonstructural protein: A new paradigm for phosphorylation-dependent viral RNA replication?" Virology 364 (2007), pp. 1-9.
Hughes et al., "Domain III of NS5A contributes to both RNA replication and assembly of hepatitis C virus particles", Journal of General Virology (2009), 90, pp. 1329-1334.
Huheey et al., Inorganic Chemistry: Principles of Structure and Reactivity. 4th Edition, HarperCollins College Publishers 1993, cover page and pp. 233-234.
Hunston et al., Synthesis and biological properties of some cyclic phosphotriesters derived from 2'-deoxy-5-fluorouridine. J. Med. Chem. 1984, vol. 27, No. 4, pp. 440-444.
International Preliminary Report on Patentability for International Application No. PCT/US2012/065681 dated May 20, 2014. (5 pages).
International Preliminary Report on Patentability for International Application No. PCT/US2015/034655 dated Dec. 15, 2016. (6 pages).
International Preliminary Report on Patentability for International Application No. PCT/US2015/034649 dated Dec. 15, 2016. (6 pages).
International Preliminary Report on Patentability for International Application No. PCT/US2014/013933 dated Mar. 1, 2016. (7 pages).
International Preliminary Report on Patentability for International Application No. PCT/US2014/013930 dated Mar. 1, 2016. (5 pages).
International Preliminary Report on Patentability for International Application No. PCT/US2013/076734 dated Jun. 23, 2015. (6 pages).
International Preliminary Report on Patentability for International Application No. PCT/US2013/041205 dated Nov. 18, 2014. (7 pages).
International Preliminary Report on Patentability for International Application No. PCT/US2013/041201 dated Nov. 18, 2014. (6 pages).
International Preliminary Report on Patentability for International Application No. PCT/US2011/060966 dated May 21, 2013. (27 pages).
International Preliminary Report on Patentability and Written Opinion issued in International Application No. PCT/US2005/032406 dated Mar. 10, 2009. (4 pages).
International Preliminary Report on Patentability issued in International Application No. PCT/EP2006/069060 dated Nov. 5, 2008. (7 pages).
International Preliminary Report on Patentability and Written Opinion issued in International Application No. PCT/US2008/058183 dated Apr. 7, 2010. (17 pages).
International Preliminary Report on Patentability and Written Opinion issued in International Application No. PCT/US2004/012472, dated Dec. 1, 2005. (8 pages).
International Preliminary Report and Written Opinion issued in International Application No. PCT/US2005/025916 dated Jan. 23, 2007. (5 pages).
International Search Report issued in International Application No. PCT/US2005/032406 dated May 8, 2008. (2 pages).
International Search Report issued in International Application No. PCT/EP2006/069060 dated Jan. 30, 2007. (3 pages).
International Search Report issued in International Application No. PCT/US2005/025916 dated Jun. 15, 2006. (1 page).
International Search Report issued in International Application No. PCT/US2004/012472 dated Dec. 30, 2004. (3 pages).
International Search Report and Written Opinion issued in International Application No. PCT/US2008/058183 dated Mar. 31, 2010. (26 pages).
International Search Report issued in International Application No. PCT/US2009/046619 dated Sep. 23, 2010. (4 pages).
International Search Report and Written Opinion issued in International Application No. PCT/US2009/069475 dated May 10, 2010. (21 pages).
International Search Report and Written Opinion for International Application No. PCT/US2011/060966 dated Sep. 19, 2012. (40 pages).
International Search Report and Written Opinion for International Application No. PCT/US2013/041201 dated Jul. 5, 2013. (10 pages).
International Search Report and Written Opinion for International Application No. PCT/US2013/041205 dated Jul. 1, 2013. (11 pages).
International Search Report and Written Opinion for International Application No. PCT/US2013/076734 dated Feb. 19, 2014. (9 pages).
International Search Report and Written Opinion for International Application No. PCT/US2014/013930 dated May 8, 2014. (7 pages).
International Search Report and Written Opinion for International Application No. PCT/US2015/034649 dated Aug. 3, 2015. (8 pages).
International Search Report and Written Opinion for International Application No. PCT/US2015/034655 dated Oct. 2, 2015. (8 pages).
International Search Report and Written Opinion for International Application No. PCT/US2012/065681 dated Jan. 25, 2013. (9 pages).
International Search Report and Written Opinion for International Application No. PCT/US2014/013953 dated Apr. 28, 2014. (9 pages).
International Search Report and Written Opinion for International Application No. PCT/US2014/013954 dated Apr. 28, 2014. (10 pages).
International Search Report and Written Opinion for International Application No. PCT/US2014/013933 dated Apr. 28, 2014. (10 pages).
International Search Report and Written Opinion issued in International Application No. PCT/US2010/035641 dated Sep. 28, 2010. (26 pages).
ION Study (NCT01701401), 7977+5885 +/− ribavirin for 12-24 weeks, HCV genotype 1 patients, Oct. 2012.

(56) References Cited

OTHER PUBLICATIONS

Iyer et al., Synthesis, In Vitro Anti-Breast Cancer Activity, and Intracellular Decomposition of Amino Acid Methyl Ester and Alkyl Amide Phosphoramidate Monoesters of 3'-Azido-3'-deoxythymidine (AZT). J. Med. Chem. 2000, vol. 43, No. 11, pp. 2266-2274.
Janssens, et al., "Evaluation of the formulation of solid dispersions by co-spray drying itraconazole with Inutec SP1, a polymeric surfactant, in combination with PVPVA 64." *Eur J Pharm Biopharm.*, Oct. 2008;70(2): 500-505.
Janssens, et al., "Formulation and characterization of ternary solid dispersions made up of Itraconazole and two excipients, TPGS 1000 and PVPVA 64, that were selected based on a supersaturation screening study," Eur J Pharm Biopharm., May 2008; 69(1): 158-166.
Janssens, et al., "Review: physical chemistry of solid dispersions," *J Pharm Pharmacol.*, Dec. 2009;61(12):1571-1586.
Jin et al., Expression, Isolation, and Characterization of the Hepatitis C Virus ATPase/RNA Helicase. Archives of Biochemistry and Biophysics 1995, vol. 323, No. 1, pp. 47-53.
Jones et al., "In-cell click labelling of small inolecules to determine subcellular localisation", J Chem Biol (2011), 4, pp. 49-53.
Jones et al., Minireview: nucleotide prodrugs. Antiviral Research 1995, vol. 27, pp. 1-17.
Jorgensen, et al., "Prediction of drug solubility from structure." *Adv Drug Deliv Rev.*, Mar. 31, 2002;54(3):355-366.
Juodka et al.,"Oligonucleotides and nucleotide-peptides. XXXIV. Synthesis and some properties of complex nucleotidyl (oligonucleotidyl)-(P—N)-amino acids (peptides) and their ethyl esters", J. Carbohydrates, Nucleosides, Nucleotides 1979, vol. 6, No. 4, pp. 333-357.
Juodka et al., "Oligonucleotides and nucleotide-peptides. XXXV. Some properties of nucleotidyl(5' →N)-amino acids esters differing in amino acid and nucleotide components," J. Carbohydrates, Nucleosides, Nucleotides 1981, vol. 8, No. 1, pp. 19-39.
Juodka et al., "Oligonucleotides and nucleotide-peptides. XXXVII. On the Mechanism of Hydrolysis of Uridylyl-(5' →N)-amino acids. Intramolecular catalysis by the a-carboxyl group of amino acids", J. Carbohydrates Nucleosides Nucleotides 1981, vol. 8, No. 6, pp. 519-535.
Kanda et al., "Inhibition of Intrahepatic Gamma Interferon Production by Hepatitis C Virus Nonstructural Protein 5A in Transgenic Mice", Journal of Virology, 2009, vol. 83, pp. 8463-8469.
Kaplan, D. E., Propagation of hepatitis C virus infection: Elucidating targets for therapeutic intervention. Drug Discovery Today: Disease Mechanisms 2006, vol. 3, pp. 471-477.
Karmwar, et al., "Investigation of properties and recrystallisation behavior of amorphous indomethacin samples prepared by different methods," International Journal of Pharmaceutics Sep. 30, 2011; 417(1-2):94-100.
Katze et al., "Ser2194 Is a Highly Conserved Major Phosphorylation Site of the Hepatitis C Virus Nonstructural Protein NS5A", Virology (2000), 278, pp. 501-513.
Kaul et al., "Essential Role of Cyclophilin A for Hepatitis C Virus Replication and Virus Production and Possible Link to Polyprotein Cleavage Kinetics", PLoS Pathogens, 2009, 5(8), e1000546, pp. 1-18.
Kim et al., C-Terminal Domain of the Hepatitis C Virus NS3 Protein Contains an RNA Helicase Activity. Biochemical and Biophysical Research Communications 1995, vol. 215, No. 1, pp. 160-166.
Kim et al., Monitoring the Intracellular Metabolism of Nucleoside Phosphoramidate Pronucleotides by $^{31}$P NMR. Nucleosides, Nucleotides & Nucleic Acids 2004, vol. 23, Nos. 1-2, pp. 483-493.
Kim et al., Direct Measurement of Nucleoside Monophosphate Delivery from a Phosphoramidate Pronucleotide by Stable Isotope Labeling and LC-ESI—MS/MS. Molecular Pharmaceutics 2004, vol. 1, No. 2, pp. 102-111.
Khamnei et al., Neighboring Group Catalysis in the Design of Nucleotide Prodrugs. J. Med. Chem. 1996, vol. 39, No. 20, pp. 4109-4115.
Klebl et al., Host cell targets in HCV therapy: novel strategy or proven practice? Antiviral Chemistry & Chemotherapy 2005, 16, pp. 69-90.
Koonin et al., Evolution and Taxonomy of Positive-Strand RNA Viruses: Implications of Comparative Analysis of Amino Acid Sequences. Critical Reviews in Biochemistry and Molecular Biology 1993, vol. 28, No. 5, pp. 375-430.
Kotra et al., Structure—Activity Relationships of 2'-Deoxy-2',2'-difluoro-L-erythro-pentofuranosyl Nucleosides. J. Med. Chem. 1997, vol. 40, No. 22, pp. 3635-3644.
Kowdley et al. Sofosbuvir with pegylated interferon alfa-2a and ribavirin for treatment-naive patients with hepatitis C genotype-1 infection (ATOMIC): an open-label, randomised, multicentre phase 2 trial. Lancet. 2013, vol. 381, pp. 2100-2107.
Klumpp et al., The Novel Nucleoside Analog R1479 (4'-Azidocytidine) Is a Potent Inhibitor of NS5B-dependent RNA Synthesis and Hepatitis C Virus Replication in Cell Culture. J Biol Chem. 2006, vol. 281, No. 7, pp. 3793-3799.
Krieger et al., "Enhancement of Hepatitis C Virus RNA Replication by Cell Culture-Adaptive Mutations", Journal of Virology, 2001, vol. 75, pp. 4614-4624.
Kriegs et al., "The Hepatitis C Virus Non-structural NS5A Protein Impairs Both the Innate and Adaptive Hepatic Immune Response in Vivo", Journal of Biological Chemistry, 2009, 284(41), pp. 28343-28351.
Kryuchkov et al., Influence of solvent on the strength of cyclic oxygen-containing phosphorus acids. Bulletin of the Academy of Sciences of the USSR, Division of chemical science 1987, vol. 36, No. 6, Part 1, pp. 1145-1148. Translated from Russian.
Kucera et al., Novel Membrane-Interactive Ether Lipid Analogs That Inhibit Infectious HIV-1 Production and Induce Defective Virus Formation. AIDS Research and Human Retroviruses 1990, vol. 6, No. 4, pp. 491-501.
Lackey et al., Enzyme-catalyzed therapeutic agent (ECTA) design: activation of the antitumor ECTA compound NB1011 by thymidylate synthase. Biochemical Pharmacology 2001, vol. 61, pp. 179-189.
Lalezari et al., 61 Once Daily PSI-7977 Plus PEGIFN/RBV in a Phase 2B Trial: Rapid Virologic Suppression in Treatment-Naive Patients With HCV GT2/GT3. Journal of Hepatology 2011, p. S28.
Lam et al., Sofosbuvir (Sovaldi) for the treatment of hepatitis C. Expert Rev. Clin. Pharmacol, 2014, 7(5), pp. 555-566.
Lam et al., Genotype and Subtype Profiling of PSI-7977 as a Nucleotide Inhibitor of Hepatitis C Virus, Antimicrobial Agents Chemotherapy 2012; vol. 56, No. 6, pp. 3359-3368.
Landowski et al., Targeted delivery to PEPT1-overexpressing cells: Acidic, basic, and secondary floxuridine amino acid ester prodrugs. Mol Cancer Ther 2005; 4(4), pp. 659-667.
Lawitz, et al., "A 12-Week Trial of Interferon-free Regimens Containing ABT-450/r and ABT-267 ± Ribavirin (RBV) in Treatment-naive Patients With HCV Genotypes 1-3," *National Aids Treatment Advocacy Project*, Jun. 9, 2013; located at http://www.natap.org/2013/APASL/APASL_01.htm.
Lawitz, et al., "A phase 1, randomized, placebo-controlled, 3-day, dose-ranging study of GS-5885, an NS5A inhibitor, in patients with genotype 1 hepatitis C," Journal of Hepatology, Feb. 5, 2012; 57(1):24-31, located at http://dx.doi.org/10.1016/j.jhep.2011.12.029.
Lawitz, et al., "Once Daily Dual-Nucleotide Combination of PSI-938 and PSI-7977 provides 94% HCV RNA < LOD at Day 14: First Purine/Pyrimidine Clinical Combination Data (The Nuclear Study)", Journal of Hepatology, (2011), 54: S543.
Lawitz, et al., "Three-Day, Dose-Ranging Study of the HCV NS5A Inhibitor GS-5885," a poster for presentation in 46th EASL annual meeting held in Mar. 30 to Apr. 3, 2011.
Lawitz, et al., "Three-Day, Dose-Ranging Study of the HCV NS5A Inhibitor GS-5885," National Aids Treatment Advocacy Project, Apr. 6, 2011 located at natap.org/2011/EASL/EASL_68.htm.
Lawitz et al., "Sofosbuvir and ledipasvir fixed-dose combination with and without ribavirin in treatment-naive and previously treated patients with genotype 1 hepatitis C virus infection (LONESTAR): an open-label, randomised, phase 2 trial", The Lancet, 2014, vol. 383, pp. 515-523.

(56) References Cited

OTHER PUBLICATIONS

Lawitz et al., Sofosbuvir for Previously Untreated Chronic Hepatitis C Infection. N Engl J Med 2013, 368, pp. 1878-1887.
Lawitz et al., Pharmacokinetics, Pharmacodynamics, and Tolerability of GS-9851, a Nucleotide Analog Polymerase Inhibitor, following Multiple Ascending Doses in Patients with Chronic Hepatitis C Infection. Antimicrobial Agents and Chemotherapy 2013, vol. 57, No. 3, pp. 1209-1217.
Lee et al., "The hepatitis C virus NS5A inhibitor (BMS-790052) alters the subcellular localization of the NS5A non-structural viral protein", Virology, 2011, 414, pp. 10-18.
Lee et al., Selective Intracellular Activation of a Novel Prodrug of the Human Immunodeficiency Virus Reverse Transcriptase Inhibitor Tenofovir Leads to Preferential Distribution and Accumulation in Lymphatic Tissue. Antimicrobial Agents and Chemotherapy 2005, vol. 49, pp. 1898-1906.
Lehsten et al., An Improved Procedure for the Synthesis of Nucleoside Phosphoramidates. Organic Process Research & Development 2002, vol. 6, No. 6, pp. 819-822.
Lemm et al., "Discovery of Potent Hepatitis C Virus NS5A Inhibitors with Dimeric Structures", AAC Accepts, 2011, pp. 1-29.
Lemm et al., "Identification of Hepatitis C Virus NS5A Inhibitors", Journal of Virology, 2010, vol. 84, pp. 482-491.
Leuner, et al., "Improving drug solubility for oral delivery using solid dispersions," European Journal of Pharmaceutics and Biopharmaceutics, (2000) 50: 47-60.
Levin, J., "High Rate of Sustained Virologic Response With the All-Oral Combination of Oaclatasvir (NS5A Inhibitor) Plus Sofosbuvir (Nucleotide NS5B Inhibitor), With or Without Ribavirin, in Treatment-Naive Patients Chronically Infected With HCV GT 1, 2, or 3", 2012, Retrieved from www.natap.org/2012/AASLD/AASLD_06.htm.
Li et al., Synthesis of the phosphoramidite derivative of 2'-deoxy-2'-C-β-methylcytidine. J. Org. Chem. 2003, vol. 68, No. 17, pp. 6799-6802.
Lima et al., Bioisosterism: A Useful Strategy for Molecular Modification and Drug Design, Current Medicinal Chemistry, 2005;12:23-49.
Lin et al., A stereospecific synthesis of 2',3'-dideoxy-β-L-cytidine (β-L-ddC), a potent inhibitor against human hepatitis B virus (HBV) and human immunodeficiency virus (HIV). Tetrahedron Letters 1994, vol. 35, No. 21, pp. 3477-3480.
Liu, R., Water-Insoluble Drug Formulation, 2nd Edition, CRC Press 2008, Ch. 18 Development of Solid Dispersion for Poorly Water Soluble Drugs, pp. 499-523.
Liver cancer 2011, mayoclinic.com/health/liver-cancer/DS00399/DSECTION=causes.
Lohmann et al., "Mutations in Hepatitis C Virus RNAs Conferring Cell Culture Adaptation", Journal of Virology, 2001, vol. 75, pp. 1437-1449.
Lohmann et al., Biochemical Properties of Hepatitis C Virus NS5B RNA-Dependent RNA Polymerase and Identification of Amino Acid Sequence Motifs Essential for Enzymatic Activity. Journal of Virology 1997, vol. 71, No. 11, pp. 8416-8428.
Lok, et al., "Combination Therapy with BMS-790052 and BMS-650032 Alone or with Pegylated Interferon and Ribavirin pegIFN/RBV Results in Undetectable HCV RNA through 12 Weeks of Therapy in HCV Genotype 1 Null Responders," *Hepatology*, (2010), 55(4) 877A.
LONESTAR Study (NCT01726517), 7977+5885 +/− ribavirin for 8-12 weeks, HCV genotype 1 patients, (2012).
Lopez Aparicio et al., Synthesis of saccharinic acid derivatives. Carbohydrate Research 1984, vol. 129, pp. 99-109.
Ma et al., Characterization of the Metabolic Activation of Hepatitis C Virus Nucleoside Inhibitor β-d-2'-Deoxy-2'-fluoro-2'-C-methylcytidine (PSI-6130) and Identification of a Novel Active 5'-Triphosphate Species. The Journal of Biological Chemistry 2007, vol. 282, No. 41, pp. 29812-29820.
Ma et al., Characterization of the Intracellular Metabolism of β-D-2'-Deoxy-2'-Fluoro-2'-C-Methyl-Cytidine and the Inhibition of HCV Polymerase NS5B by its 5'-Triphosphate Species. Program and Abstracts 23, Antiviral Research 74, 2007, p. A36.
MacDonald et al., "Hepatitis C virus NS5A: tales of a promiscuous protein", Journal of General Virology (2004), 85, pp. 2485-2502.
Mao, et al., "Time-dependence of molecular mobility during structural relaxation and its impact on organic amorphous solids: an investigation based on a calorimetric approach," Pharmaceutical Research Aug. 2006; 23(8):1906-1917.
Marsac, et al., "A comparison of the physical stability of amorphous felodipine and nifedipine systems," Pharmaceutical Research Oct. 2006; 23(10):2306-2316.
McCormick et al., "Tagging of NS5A expressed from a functional hepatitis C virus replicon", Journal of General Virology (2006), 87, pp. 635-640.
McGuigan et al., Aryl phosphate derivatives of AZT retain activity against HIV1 in cell lines which are resistant to the action of AZT. Antiviral Research 1992, vol. 17, pp. 311-321.
McGuigan et al., Application of Phosphoramidate ProTide Technology Significantly Improves Antiviral Potency of Carbocyclic Adenosine Derivatives. J. Med. Chem. 2006, vol. 49, No. 24, pp. 7215-7226.
McGuigan et al., Application of Phosphoramidate Pronucleotide Technology to Abacavir Leads to a Significant Enhancement of Antiviral Potency. J. Med. Chem. 2005, vol. 48, No. 10, pp. 3504-3515.
McGuigan et al., Synthesis and evaluation of some novel phosphoramidate derivatives of 3'-azido-3'-deoxythymidine (AZT) as anti-HIV compounds. Antiviral Chemistry & Chemotherapy 1990, vol. 1, No. 2, pp. 107-113.
McGuigan et al., Aryl Phosphoramidate Derivatives of d4T Have Improved Anti-HIV Efficacy in Tissue Culture and May Act by the Generation of a Novel Intracellular Metabolite. J. Med. Chem. 1996, vol. 39, No. 8, pp. 1748-1753.
McGuigan et al., Synthesis and anti-HIV activity of some novel chain-extended phosphoramidate derivatives of d4T (stavudine): esterase hydrolysis as a rapid predictive test for antiviral potency. Antiviral Chemistry & Chemotherapy 1998, vol. 9, pp. 109-115.
McGuigan et al., Synthesis, anti-human immunodeficiency virus activity and esterase lability of some novel carboxylic ester-modified phosphoramidate derivatives of stavudine (d4T). Antiviral Chemistry & Chemotherapy 1998, vol. 9, pp. 473-479.
McGuigan et al., Phosphoramidate derivatives of stavudine as inhibitors of HIV: unnatural amino acids may substitute for alanine. Antiviral Chemistry & Chemotherapy, 2000, 11, pp. 111-116.
McGuigan et al., Certain phosphoramidate derivatives of dideoxy uridine (ddU) are active against HIV and successfully by-pass thymidine kinase. FEBS Letters 351, 1994, pp. 11-14.
McGuigan et al., Sub Micromolar Inhibitors of HCV Generated from Inactive Nucleosides by Application of ProTide Technology. Program and Abstracts 24, Antiviral Research 74, 2007, pp. A36-A37.
McIntee et al., Amino acid phosphoramidate nucleosides: potential ADEPT/GDEPT substrates. Bioorganic & medicinal chemistry letters 2001, vol. 11, pp. 2803-2805.
McIntee et al., Probing the Mechanism of Action and Decomposition of Amino Acid Phosphomonoester Amidates of Antiviral Nucleoside Prodrugs. J. Med. Chem. 1997, vol. 40, No. 21, pp. 3323-3331.
Meier et al., Cyclic saligenyl phosphotriesters of 2',3'-dideoxy-2',3'-didehydrothymidine (d4T)—a new pro-nucleotide approach, Bioorganic & Medicinal Chemistry Letters 1997, vol. 7, No. 2, 21, pp. 99-104.
Metatla, et al., "The Vogel-Fulcher-Tamman equation investigated by atomistic simulation with regard to the Adam-Gibbs model" Macromolecules 2007, 40(26): 9680-9685.
Meyers et al., Molecular Characterization of Pestiviruses. Advances in Virus Research 1996, vol. 47, pp. 53-118.
Mitchell et al., Bioreversible protection for the phospho group: bioactivation of the di(4-acyloxybenzyl) and mono(4-acyloxybenzyl) phosphoesters of methylphosphonate and phosphonoacetate. J. Chem. Soc., Perkin Trans. 1, 1992, pp. 2345-2353.

(56) References Cited

OTHER PUBLICATIONS

Miyanari et al., "Hepatitis C Virus Non-structural Proteins in the Probable Membranous Compartment Function in Viral Genome Replication", The Journal of Biological Chemistry, 278(50), 2003, pp. 50301-50308.

Moennig et al., The Pestiviruses. Advances in Virus Research 1992, vol. 41, pp. 53-98.

Mogalian et al., (2016), "Effect of Food and Acid-Reducing Agents on the Relative Bioavailability and Pharmacokinetics of Sofosbuvir/Velpatasvir Fixed-Dose Combination Tablet," ASCPT 2016 Annual Meeting, 1 page.

Monath, T. P., Japanese Encephalitis—A Plague of the Orient. The New England Journal of Medicine 1988, vol. 319, No. 10, pp. 641-643.

Moradpour et al., "Replication of hepatitis C virus", Nature Reviews, Microbiology, vol. 5, 2007, pp. 453-463.

Mourier et al., Enantioselective synthesis and biological evaluation of 5-o-carboranyl pyrimidine nucleosides. Bioorganic & Medicinal Chemistry 1999, vol. 7, pp. 2759-2766.

Mühlberger et al., "HCV-related burden of disease in Europe: a systematic assessment of incidence, prevalence, morbidity, and mortality", BMC Public Health, 2009, 9:34. bmcpublichealth.biomedcentral.com/track/pdf/10.1186/1471-2458-9-34.

Mukaizawa, et al., "Novel oral absorption system containing polyamines and bile salts enhances drug transport via both transcellular and paracellular pathways across Caco-2 cell monolayers." International Journal of Pharmaceutics Feb. 9, 2009; 367(1-2):103-108.

Murakami et al., "Mechanism of Activation of PSI-7851 and Its Diastereoisomer PSI-7977", Journal of Biological Chemistry, 2010, 285(45), pp. 34337-34347.

Murakami et al., The Mechanism of Action of β-D-2'-Deoxy-2'-Fluoro-2'-C-Methylcytidine Involves a Second Metabolic Pathway Leading to β-D-2'-Deoxy-2'-Fluoro-2'-C-Methyluridine 5'-Triphosphate, a Potent Inhibitor of the Hepatitis C Virus RNA-Dependent RNA Polymerase. Antimicrobial Agents and Chemotherapy 2008, vol. 52, No. 2, pp. 458-464.

Murakami et al., Mechanism of Activation of β-D-2'-Deoxy-2'-Fluoro-2'-C-Methylcytidine and Inhibition of Hepatitis C Virus NS5B RNA Polymerase. Antimicrobial Agents and Chemotherapy 2007, vol. 51, No. 2, pp. 503-509.

Murakami et al., The Mechanism of Action of β-D-2'-Deoxy-2'-fluoro-2'-C-methylcytidine Involves a Second Metabolic Pathway Leading to β-D-2'-Deoxy-2'-fluoro-2'-C-methyluridine 5'-Triphosphate, a Potent Inhibitor of the HCV RNA-Dependent RNA Polymerase. 14th International Symposium on Hepatitis C Virus and Related Viruses, Glasgow, Scotland Sep. 2007.

Nakayama et al., A Highly Enantioselective Synthesis of Phosphate Triesters. J. Am. Chem. Soc. 1990, vol. 112, No. 19, pp. 6936-6942.

NATAP Report of Cheng, "Antiviral Activity and Resistance Profile of the Novel HCV NS5A Inhibitor GS-5885", presentation at EASL Barcelona, Spain, Apr. 18-22, 2012.

NATAP Report of Everson GT, "An Interferon-Free, Ribavirin-Free 12-Week Regimen of Daclatasvir (DCV), Asunaprevir (ASV) and BMS-791325 Yielded SVR4 of 94% in Treatment-Naïve Patients with Genotype (GT) 1 Chronic Hepatitis C Virus (HCV) Infection", presentation at AASLD, Boston, Nov. 9-12, 2012.

NATAP Report of EJ Gane, "PSI-7977: ELECTRON Interferon is not required for Sustained Virologic Response in Treatment-Naïve Patients with HCV GT2 or GT3", AASLD, Nov. 6-9, 2011.

NATAP Report of Lawitz et al, "Once daily dual-nucleotide combination of PSI-938 and PSI-7977 provides 94% HCV RNA <LOD at day 14: First purine/pyrimidine clinical combination data (The Nuclear Study)" EASL Mar. 30-Apr. 3, 2011.

NATAP Report of M Sulkowski, "Potent Viral Suppression With the All-Oral Combination of Daclatasvir (NS5A Inhibitor) and GS-7977 (Nucleotide NS5B Inhibitor), +/− Ribavirin, in Treatment-Naive Patients With Chronic HCV GT1, 2, or 3", EASL Barcelona, Spain, Apr. 18-22, 2012.

Neidlein et al., Mild Preparation of 1-Benzyloxyiminoalkylphosphonic Dichlorides: Application to the Synthesis of Cyclic Phosphonic Diesters and Cyclic Monoester Amides. Heterocycles 1993. vol. 35, No. 2, pp. 1185-1203.

Nelson et al., The question of chair-twist equilibria for the phosphate rings of nucleoside cyclic 3',5'-monophosphates. $^1$H NMR and x-ray crystallographic study of the diastereomers of thymidine phenyl cyclic 3',5'-monophosphate. J. Am. Chem. Soc. 1987, vol. 109, No. 13, pp. 4058-4064.

Nelson et al., 1372 Once Daily PSI-7977 Plus PEG-IFN/RBV IN HCV GT1: 98% Rapid Virologic Response, Complete Early Virologic Response: The Proton Study. Journal of Hepatology 2011 vol. 54, S544.

Neumann, et al., "Hepatitis C Viral Dynamics in Vivo and the Antiviral Efficacy of Interferon-α Therapy," Science , (1998) 282:103-107.

Newman, et al., "Assessing the Performance of Amorphous Solid Dispersions", Journal of Pharmaceutical Sciences (2012), 101(4): 1355-1377.

Ni et al., Progress and development of small molecule HCV antivirals. Current Opinion in Drug Discovery & Development 2004, vol. 7, No. 4, pp. 446-459.

Nifantyev et al., Synthesis and Structure of Some Stable Phospholane-Phospholanes. Phosphorus, Sulfur, and Silicon 1996, vo. 113, pp. 1-13.

Non-Final Office Action for Brazil Application No. BR1120160036441 dated Aug. 21, 2019. (13 pages).

Non-Final Office Action for Brazil Application No. BR1120160036441 dated Sep. 13, 2019. (15 pages).

North et al., Hepatitis C treatment and SVR: the gap between clinical trials and real-world treatment aspirations. General Hospital Psychiatry 2013, 35, pp. 122-128.

Notice of Preliminary Rejection for Korean Application No. 10-2016-7007662 dated Jun. 22, 2020.

Novak, J. J. K., "Chiroptical Properties of 2-Methyl-1,4-Lactones; Revised Absolute Configuration of 2-Deoxy-2-C-Methyl-erythro-D-Pentono-1,4-Lactones," Collection Czechoslov. Chem. Commun. 1974, vol. 39, pp. 869-882.

Novak, J. J. K., "Nucleic Acid Components and Their Analogues CXLIII. Nucleosides Derived from 2-Deoxy-2(R)-C-Methyl-erythro-D-Pentose," Collection Czechoslov. Chem. Commun. 1971, vol. 36, pp. 3670-3677.

Ochoa, et al., "Determination of cell membrane permeability in concentrated cell ensembles." Biophys J., Nov. 1987; 52(5):763-774.

Office Action dated May 22, 2015 for U.S. Appl. No. 14/168,340.
Office Action dated Jun. 30, 2016 for U.S. Appl. No. 14/168,340.
Office Action dated Aug. 17, 2015 for U.S. Appl. No. 14/168,340.
Office Action for Chinese Patent Application No. 201480047195.3 dated Sep. 17, 2018. (5 pages).
Office Action for Canada Application No. 2,921,160 dated Feb. 18, 2020. (3 pages).
Office Action for Mexico Application No. MX/a/2016/002185 dated Mar. 19, 2019. (3 pages).
Office Action and Search Report for Chinese Application No. 201480047195.3 dated Jan. 17, 2018. (18 pages).
Office Action and Search Report for Taiwan Application No. 103103761 dated Aug. 28, 2017. (7 pages).
Office Action for Israeli Patent Application No. 243988 dated Feb. 10, 2019. (1 page).
Office Action for Pakistan Application No. 0055/2014 dated Feb. 2, 2016. (2 pages).
Official Action for Bolivian Patent Application No. SP-00026-2014 dated May 22, 2018. (8 pages).
Official Action for Eurasian Application No. 201690473/26 dated Oct. 20, 2017. (2 pages).
Official Action for Eurasian Patent Application No. 201690473/26 dated Jul. 10, 2018. (1 page).
Official Action for Eurasian Patent Application No. 201690473/26 dated May 20, 2016. (1 page).
Official Action for Mexican Patent Application No. MX/a/2016/002185 dated Oct. 19, 2018. (3 pages).

(56) References Cited

OTHER PUBLICATIONS

Official Notification for Israeli Patent Application No. 243988 dated Oct. 15, 2018. (2 pages).
Oishi et al., Asymmetric dihydroxylation of chiral olefins. High control of diastereofacial selection. Tetrahedron Letters 1993, vol. 34, No. 22, pp. 3573-3576.
Olsen et al., "2'-Modified Nucleoside Analogs as Inhibitors of Hepatitis C RNA Replication," Program and Abstracts, 16th International Conference on Antiviral Research, Abstract No. 121, p. A76 (Apr. 27-May 1, 2003).
Opposition by the Delhi Network of Positive People (DNP+) for India Application No. 201627008488 filed on Jul. 9, 2018.
Otto, "Evaluation of nucleoside analogs in the hepatitis C virus replicon system," Framing the Knowledge of Therapeutics for Viral Hepatitis Ed. by RF Schinazi and ER Schiff. 2006, pp. 247-261.
Partial International Search Report & Invitation to Pay Additional Fees issued in International Application No. PCT/US2009/069475 dated Mar. 5, 2010. (7 pages).
Patterson, et al., "Melt extrusion and spray drying of carbamazepine and dipyridamole with polyvinylpyrrolidone/vinyl acetate copolymers," Drug Dev Ind Pharm., Jan. 2008;34(1): 95-106.
Perrone et al., First Example of Phosphoramidate Approach Applied to a 4'-Substituted Purine Nucleoside (4'-Azidoadenosine): Conversion of an Inactive Nucleoside to a Submicromolar Compound versus Hepatitis C Virus. Journal of Medicinal Chemistry 2007, vol. 50, No. 22, pp. 5463-5470.
Perrone et al., Application of the Phosphoramidate ProTide Approach to 4'-Azidouridine Confers Sub-micromolar Potency versus Hepatitis C Virus on an Inactive Nucleoside. Journal of Medicinal Chemistry 2007, vol. 50, No. 8, pp. 1840-1849.
Perrone, P., Design, synthesis and biological evaluation of novel nucleotide prodrugs as potential anti hepatitis C virus agents. Philosophiae Doctor Thesis, Cardiff University, (2007).
Piantadosi et al., Synthesis and evaluation of novel ether lipid nucleoside conjugates for anti-HIV-1 activity. J. Med. Chem. 1991, vol. 34, No. 4, pp. 1408-1414.
Pierra et al., Synthesis and Pharmacokinetics of Valopicitabine (NM283), an Efficient Prodrug of the Potent Anti-HCV Agent 2'-C-Methylcytidine. J. Med. Chem. 2006, vol. 49, No. 22, pp. 6614-6620.
Pietschmann et al., "Characterization of Cell Lines Carrying Self-Replicating Hepatitis C Virus RNAs", Journal of Virology, 2001, 75(3), pp. 1252-1264.
Piper Jaffray Report on Gilead Sciences Inc., Nov. 21, 2011.
Pharmasset, Inc., Pharmasset Announces 91 % SVR12 From the PROTON Trial in Subjects With Hepatitis C Genotype 1. Sep. 6, 2011 PRNewswire.
Pharmasset, Inc. Press Release dated Jul. 31, 2009.
Pockros et al., JUMP-C: A Randomized Trial of Mericitabine Plus Pegylated Interferon Alpha-2a/Ribavirin for 24 Weeks in Treatment-Naive HCV Genotype 1/4 Patients. Hepatology 2013, vol. 58, No. 2, pp. 514-523.
Pogam, S. L., No Evidence of R7128 Drug Resistance After Up to 4 Weeks Treatment of GT 1, 2 and 3 Hepatitis C Virus Infected Individuals. 44th Annual Meeting of European Association for the Study of the Liver (EASL). Copenhagen, Denmark. Apr. 22-26, 2009).
Program and Abstracts of the Twenty-Fifth International Conference on Antiviral Research (ICAR), 2012.
PubChem SID: 85332817, PubChem database from Feb. 2011 disclosing the velpatasvir compound. (5 pages).
Quaroni, et al., "Development of intestinal cell culture models for drug transport and metabolism studies." Advanced Drug Delivery Reviews (1996), 22:3-52.
Ray et al., Intracellular Metabolism of the Nucleotide Prodrug GS-9131, a Potent Anti-Human Immunodeficiency Virus Agent. Antimicrobial Agents and Chemotherapy 2008, vol. 52, No. 2 pp. 648-654.
Reed et al., "The NS5A/NS5 Proteins of Viruses from Three Genera of the Family Flaviviridae Are Phosphorylated by Associated Serine/Threonine Kinases", Journal of Virology, 1998, 72(7), pp. 6199-6206.
Rejection Decision for Brazil Application No. BR1120160036441 dated Jun. 3, 2020.(9 pages).
Remy et al., Studies on Fluorinated Pyrimidines. XIV. The Synthesis of Derivatives of 5-Fluoro-2'-deoxyuridine 5'-Phosphate and Related Compounds. J. Org. Chem. 1962 vol. 27, pp. 2491-2500.
Revised BMS/Pharmasset trial protocol for NCT01359644, May 24, 2011. ClinicalTrials.gov archive.
Revised BMS/Pharmasset trial protocol for NCT01359644, Jan. 5, 2012. ClinicalTrials.gov archive.
Revised ELECTRON protocol (NCT01260350), arms 21 and 22 added for 7977+5885 +/− ribavirin for 6 weeks in treatment-naïve, HCV genotype 1 patients, Nov. 20, 2012.
Revised ELECTRON trial protocol for NCT01260350, May 7, 2012. ClinicalTrials.gov archive.
Revised Protocol for NCT01260350 dated Jul. 9, 2012. ClinicalTrials.gov archive.
Revised Protocol for NCT01466790, Nov. 7, 2011.
Revised Protocol for NCT01701401, Oct. 2012.
Reynolds et al., "Thermodynamics of Ligand Binding and Efficiency", ACS Med. Chem. Lett., 2011, pp. A-E.
Rice, C. M., Chapter 30, Flaviviridae: The Viruses and Their Replication. Fields Virology 1996, 3rd Edition, vol. 1, pp. 931-959.
Roberts et al., 731 Interim Results of a Multiple Ascending Dose Study of R1626, A Novel Nucleoside Analog Targeting HCV Polymerase in Chronic HCV Patients. J Hepatol 2006, 44, S269.
Robins et al., Nucleic Acid Related Compounds. 91. Biomimetic Reactions Are in Harmony with Loss of 2'-Substituents as Free Radicals (Not Anions) during Mechanism-Based Inactivation of Ribonucleotide Reductases. Differential Interactions of Azide, Halogen, and Alkylthio Groups with Tributylstannane and Triphenylsilane. Journal of the American Chemical Society 1996, vol. 118, No. 46, pp. 11341-11348.
Robinson, M. J. T., Oxford Chemistry Primers: Organic Stereochemistry. OUP 2000, cover page and sections 1.4-1.8.
Romine et al., "Inhibitors of HCV NS5A: From Iminothiazolidinones to Symmetrical Stilbenes", ACS Med. Chem. Lett. 2011, 2, pp. 224-229.
Rong, et al., "Rapid Emergence of Protease Inhibitor Resistance in Hepatitis C Virus," Science Translational Medicine, (2010), vol. 2, Issue 30, 30ra32, pp. 1-9.
Saboulard et al., Characterization of the Activation Pathway of Phosphoramidate Triester Prodrugs of Stavudine and Zidovudine. Molecular Pharmacology 1999, vol. 56, pp. 693-704.
Sakurai, et al., "Polymer Combination Increased Both Physical Stability and Oral Absorption of Solid Dispersions Containing a Low Glass Transition Temperature Drug: Physicochemical Characterization and In Vivo Study," Chem Pharm Bull (Tokyo), (2012), 60(4): 459-64.
Saneyoshi et al., Facile synthesis of 2'-O-cyanoethyluridine by ring-opening reaction of 2,2'anhydrouridine with cyanoethyl trimethylsilyl ether in the presence of $BF_3 \cdot Et_2O$. Tetrahedron Letters 48, 2007, pp. 8554-8557.
Scheel et al., "Recombinant HCV Variants With NS5A From Genotypes 1-7 Have Different Sensitivities to an NS5A Inhibitor but Not Interferon-a", Gastroenterology, 2011, 140, pp. 1032-1042.
Schlutter, "New drugs hit the target" Nature, (2011), vol. 474, pp. S5-S7.
Schmitz et al., "NS5A—From Obscurity to New Target for HCV Therapy", Recent Patents on Anti-Infective Drug Discovery, 2008, 3, pp. 77-92.
Schultz, C., Prodrugs of Biologically Active Phosphate Esters. Bioorganic and Medicinal Chemistry 2003, vol. 11, pp. 885-898.
Shamblin, et al., "Characterization of the time scales of molecular motion in pharmaceutically important glasses" J Phys Chem B, (1999), 103(20): 4113-4121.
Shih et al., Preparation and Structures of 2-Dimethylamino-4-phenyl-1,3,2-dioxaphosphorinane-2-oxides. Bull. Inst. Chem. Academia Sinica 1994, No. 41, pp. 9-16.

(56) References Cited

OTHER PUBLICATIONS

Shimakami et al., "Hepatitis C: recent successes and continuing challenges in the development of improved treatment modalities", Current Opinion in Pharmacology 2009, 9, pp. 537-544.
Siccardi et al., Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers. Journal of Pharmacology and Experimental Therapeutics 2003, vol. 307, No. 3, pp. 1112-1119.
Siccardi et al., Stereospecific chemical and enzymatic stability of phosphoramidate triester prodrugs of d4T in vitro. European Journal of Pharmaceutical Sciences 2004, vol. 22, pp. 25-31.
Siddiqui et al., Enhancing the Aqueous Solubility of d4T-based Phosphoramidate Prodrugs. Bioorganic & Medicinal Chemistry Letters 10 (2000), pp. 381-384.
Siddiqui et al., Design and Synthesis of Lipophilic Phosphoramidate d4T-MP Prodrugs Expressing High Potency Against HIV in Cell Culture: Structural Determinants for in Vitro Activity and QSAR. J. Med. Chem. 1999, vol. 42, No. 20, pp. 4122-4128.
Siddiqui et al., The presence of substituents on the aryl moiety of the aryl phosphoramidate derivative of d4T enhances anti-HIV efficacy in cell culture: a structure-activity relationship. J. Med. Chem. 1999, vol. 42, No. 3, pp. 393-399.
Slide presentation shown during Gilead Sciences Inc's "Q4 2011 Earnings Results, Conference Call and Webcast" on Feb. 2, 2012.
Smirnov et al., A fluorescent study of tryptophan derivatives of oligonucleotide and their helical complexes with polyuridylic acid. FEBS Letters 1975, vol. 51, No. 1, pp. 211-214.
Snoeck, et al., "A Comprehensive Hepatitis C Viral Kinetic Model Explaining Cure", Clinical Pharmacology & Therapeutics, (2010), 87(6): 706-713.
Sofia et al., "$\beta$-D-2'-Deoxy-2'-fluoro-2'-C-methyluridine Phosphoramidates: Potent and Selective Inhibitors of HCV RNA Replication", 2nd International Workshop on HCV, Poster #7 (Oct. 31, 2007).
Sofia et al., $\beta$-D-2'-Deoxy-2'-fluoro-2'-C-methyluridine Phosphoramidates: Potent and Selective Inhibitors of HCV RNA Replication. Poster #P-259, 14th International Symposium on Hepatitis C Virus and Related Viruses, Glasgow, Scotland, Sep. 9-13, 2007.
Sofia, M. J., "$\beta$-D-2'-Deoxy-2'-fluoro-2'-C-methyluridine Phosphoramidates: Potent and Selective Inhibitors of HCV RNA Replication", 2nd International Workshop on HCV-Resistance and New Compounds, Oct. 31, 2007.
Sofia, M.J., "R7128, A Potent and Selective Nucleoside Inhibitor of HGV NS5B Polymerase: An Overview of Clinical Efficacy and Progress Toward Second Generation Inhibitors", CHI:HCV Drug Discovery 2008, Pharmasset, Apr. 28, 2008.
Sofia et al., Discovery of a $\beta$-d-2'-Deoxy-2'-$\alpha$-fluoro-2'-$\beta$-C-methyluridine Nucleotide Prodrug (PSI-7977) for the Treatment of Hepatitis C Virus. J. Med. Chem. 2010, vol. 53, No. 19, pp. 7202-7218.
Song et al., Pharmacokinetics of Amino Acid Phosphoramidate Monoesters of Zidovudine in Rats. Antimicrobial Agents and Chemotherapy 2002, vol. 46, No. 5, pp. 1357-1363.
Soriano et al., Hepatitis C therapy with HCV NS5B polymerase inhibitors. Expert Opinion on Pharmacotherapy 2013, pp. 1-10.
Starrett Jr. et al., Synthesis, oral bioavailability determination, and in vitro evaluation of prodrugs of the antiviral agent 9-[2-(phosphonomethoxy)ethyl]adenine (PMEA). J. Med. Chem. 1994, vol. 37, No. 12, pp. 1857-1864.
Stella, V. J., Prodrugs as therapeutics, Expert Opinion on Therapeutic Patents 2004, vol. 14, No. 3, pp. 277-280.
STN Registry No. 1190307-88-0, "Sofosbuvir," Retrieved from STN Registry File No. 2013-10-25. (1 page).
Strader et al., Diagnosis, Management, and Treatment of Hepatitis C. AASLD Practice Guideline. Hepatology 2004, vol. 39, No. 4, pp. 1147-1171.
Stuyver et al., Inhibition of hepatitis C replicon RNA synthesis by $\beta$-D-2'-deoxy-2'-fluoro-2'-C-methylcytidine: a specific inhibitor of hepatitis C virus replication. Antiviral Chemistry & Chemotherapy 2006, vol. 17, No. 2, pp. 79-87.
Stuyver et al., Dynamics of Subgenomic Hepatitis C Virus Replicon RNA Levels in Huh-7 Cells after Exposure to Nucleoside Antimetabolites. Journal of Virology 2003, vol. 77, No. 19, pp. 10689-10694.
Stuyver et al., Ribonucleoside Analogue That Blocks Replication of Bovine Viral Diarrhea and Hepatitis C Viruses in Culture. Antimicrobial Agents and Chemotherapy 2003, vol. 47, No. 1, pp. 244-254.
Stuyver et al., Inhibition of the Subgenomic Hepatitis C Virus Replicon in Huh-7 Cells by 2'-Deoxy-2'-Fluorocytidine. Antimicrobial Agents and Chemotherapy 2004, vol. 48, No. 2, pp. 651-654.
Sulkowski, et al., 1421 "High Sustained Virologic Response Rate in Treatment-Naïve HCV Genotype 1A and 1B patients treated for 12 Weeks with an Interferon-Free All-Oral Quad Regimen: Interim Results" Journal of Hepatology (2012), vol. 56, s560.
Sulkowski, et al., "Potent Viral Suppression With the All-Oral Combination of Daclatasvir (NS5A Inhibitor) and GS-7977 (Nucleotide NS5B Inhibitor),+/– Ribavirin, in Treatment-Naive Patients With Chronic HCV GT1, 2, or 3 (100% SVR gt1, 91% gt2)", EASL Barcelona, Spain, Apr. 18-22, 2012.
Sulkowski, et al., "Potent Viral Suppression With the All-Oral Combination of Daclatasvir (NS5A Inhibitor) and GS-7977 (Nucleotide NS5B Inhibitor), +/– Ribavirin, in Treatment-Naive Patients With Chronic HCV GT1, 2, or 3," *Journal of Hepatologys*, (2012), 56:560.
Supplementary Examination Report for Singapore Patent Application No. 11201600919U dated Apr. 2, 2018. (2 pages).
Tan et al., Hepatitis C Therapeutics: Current Status and Emerging Strategies. Nature Reviews Drug Discovery 2002, vol. 1, pp. 867-881.
Tellinghuisen et al., "Regulation of Hepatitis C Virion Production via Phosphorylation of the NS5A Protein", PLoS Pathogens, 2008, 4(3), e1000032, pp. 1-17.
Tellinghuisen et al., "Structure of the zinc-binding domain of an essential component of the hepatitis C virus replicase", Nature Publishing Group, 2005, 435(19), pp. 374-379.
Tellinghuisen et al., "The NS5A Protein of Hepatitis C Virus Is a Zinc Metalloprotein", The Journal of Biological Chemistry, 2004, 279(47), pp. 48576-48587.
Third Party Observations for Chinese Application No. 201480047195.3 dated Dec. 13, 2017. (50 pages).
Third-Party Opinion, ANVISA for Brazilian Application No. BR112016003644-1 dated Jul. 12, 2019. (21 pages).
Tomei et al., NS3 Is a Serine Protease Required for Processing of Hepatitis C Virus Polyprotein. Journal of Virology 1993, vol. 67, No. 7, pp. 4017-4026.
Transcript of Biotechnology Industry Organization (BIO) CEO and Investor Conference, Feb. 14, 2012.
Transcript of Gilead Sciences Inc's "Q4 2011 Earnings Call Transcript" on Feb. 2, 2012.
Tripathi, K.D., Essentials of Medical Pharmacology, 5th Edition, Jaypee Brothers Medical Publishers (2004), 4106-4107, lines 10-13.
Trousdale et al., Activity of 1-(2'-fluoro-2'-deoxy-$\beta$-D-arabinofuranosyl)thymine against herpes simplex virus in cell cultures and rabbit eyes. Antimicrobial Agents and Chemotherapy 1983, vol. 23, No. 6, pp. 808-813.
Tung, et al., "Formulation of solid dispersion of rebamipide evaluated in a rat model for improved bioavailability and efficacy." Journal of Pharmacy and Pharmacology Dec. 2011; 63(12):1539-1547.
Uchiyama et al., O-selective phosphorylation of nucleosides without N-protection. J. Org. Chem. 1993, vol. 58, No. 2, pp. 373-379.
Uckun et al., In vivo Pharmacokinetics and Toxicity Profile of the Anti-HIV Agent Stampidine in Dogs and Feline Immunodeficiency Virus-infected Cats. Arzneim.-Forsch./Drug Res. 2006, vol. 56, No. 2a, pp. 176-192.
Valette et al., Decomposition Pathways and in Vitro HIV Inhibitory Effects of IsoddA Pronucleotides: Toward a Rational Approach for Intracellular Delivery of Nucleoside 5'-Monophosphates. J. Med. Chem. 1996, vol. 39, No. 10, pp. 1981-1990.

(56) References Cited

OTHER PUBLICATIONS

Van Rompaey et al., *Mycobacterium tuberculosis* thymidine monophosphate kinase inhibitors: Biological evaluation and conformational analysis of 2 '- and 3 '-modified thymidine analogues. Eur. J. Org. Chem. 2003, pp. 2911-2918.
Vanheusden et al., Synthesis and evaluation of thymidine-5'-O-monophosphate analogues as inhibitors of *Mycobacterium tuberculosis* thymidylate kinase. Bioorganic & Medicinal Chemistry Letters 12, 2002, pp. 2695-2698.
Vanheusden et al., Discovery of Bicyclic Thymidine Analogues as Selective and High-Affinity Inhibitors of *Mycobacterium tuberculosis* Thymidine Monophosphate Kinase. J. Med. Chem. 2004, vol. 47, No. 25, pp. 6187-6194.
Vasconcelos, et al., "Solid dispersions as strategy to improve oral bioavailability of poor water soluble drugs," Drug Discovery Today, (2007), vol. 12, Nos. 23/24, 1068-1075.
Venkatachalam et al., Synthesis and metabolism of naphthyl substituted phosphoramidate derivatives of stavudine. Bioorganic & Medicinal Chemistry 2006, vol. 14, pp. 5161-5177.
Venkatachalam et al., Rational Drug Design of Multifunctional Phosphoramidate Substituted Nucleoside Analogs. Current Pharmaceutical Design 2004, vol. 10, No. 15, pp. 1713-1726.
Vitale et al., "2-Arylbenzimidazoles as Antiviral and Antiproliferative Agents—Part 1", Medicinal Chemistry, 2008, 4, pp. 605-615.
Volpe, "Application of method suitability for drug permeability classification." AAPS J., Dec. 2010; 12(4): 670-678.
Wagner et al., Antiviral Nucleoside Drug Delivery via Amino Acid Phosphoramidates. Nucleosides, Nucleotides and Nucleic Acids 1999, vol. 18, Nos. 4-5, pp. 913-919.
Wagner et al., Pronucleotides: Toward the In Vivo Delivery of Antiviral and Anticancer Nucleotides. Med Res Rev 2000, 20, No. 6, pp. 417-451.
Walker et al. "Promising candidates for the treatment of chronic hepatitis C", Expert Opinion on Investigational Drugs, 2003, vol. 12, No. 8, pp. 1269-1280.
Walter, et al., "Permeability of small nonelectrolytes through lipid bilayer membranes." J. Membrane Biol. (1986), 90(3): 207-217.
Wang, et al., "Solid state characteristics of ternary solid dispersions composed of PVP VA64, Myrj 52 and itraconazole." International Journal of Pharmaceutics Oct. 13, 2005; 303(1-2):54-61.
Warrener et al., Pestivirus NS3 (p80) Protein Possesses RNA Helicase Activity. Journal of Virology 1995, vol. 69, No. 3, pp. 1720-1726.
Wedemeyer et al., PROPEL: A randomized trial of mericitabine plus peginterferon alpha-2a/ribavirin therapy in treatment-naïve HCV genotype 1/4 patients. Hepatology 2013, vol. 58, No. 2, pp. 524-537.
Wiskerchen et al., Pestivirus Gene Expression: Protein p80 of Bovine Viral Diarrhea Virus Is a Proteinase Involved in Polyprotein Processing. Virology 1991, vol. 184, pp. 341-350.
Wolff, M. E., Burger's medicinal chemistry and drug discovery. Fifth Edition. vol. 1: Principles and Practice, 1995, pp. 975-977.
World Health Organization. 19th edition, WHO Model List of Essential Medicines, 2015.
Wozniak et al., The stereospecific synthesis of P-chiral biophosphates and their analogues by the Stec reaction. Chem. Soc. Rev. 2003, 32, pp. 158-169.

Written Opinion of PCT/US2005/032406 dated May 8, 2008.
Written Opinion of PCT/EP2006/069060 dated Jan. 30, 2007.
Wu et al., Targeting NS5B RNA-Dependent RNA Polymerase for Anti-HCV Chemotherapy. Current Drug Targets—Infectious Disorders 2003, vol. 3 , No. 3 , pp. 207-219.
Wu et al., Synthesis and Biological Activity of a Gemcitabine Phosphoramidate Prodrug. J. Med. Chem. 2007, vol. 50, No. 15, pp. 3743-3746.
Xiao-Ling et al., Study on the Chirality of Sulfur in Ethyl (2S, 3R, 4R)-4,5-O-Isopropylidene-2,3-Sulfinyl-2,3,4,5-Tetrahydroxy-Pentanoate. Acta Chimica Sinica 1997, vol. 55, pp. 600-604.
Xiao-Ling et al., "The Synthesis of (2S,3R)-Sphingosine from D-Mannitol", Acta Chimica Sinica, 1996, vol. 54, pp. 826-832.
Xu, et al., "Preparation and evaluation of Ibuprofen solid dispersion systems with kollidon particles using a pulse combustion dryer system," Chem Pharm Bull (Tokyo), Nov. 2007;55(11): 1545-50.
Xu et al., Bovine Viral Diarrhea Virus NS3 Serine Proteinase: Polyprotein Cleavage Sites, Cofactor Requirements, and Molecular Model of an Enzyme Essential for Pestivirus Replication. Journal of Virology 1997, vol. 71, No. 7, pp. 5312-5322.
Yakuji Shinsa Kenkyukai, "Iyakuhin Seizo Shishi 2001," Sep. 30, 2013, Jiho Inc., cover page, pp. 283 to 284, colophon.
Yoshioka et al., "Crystallization of Indomethacin from the Amorphous State below and above Its Glass Transition Temperature", Journal of Pharmaceutical Sciences, 1994, 83(12), pp. 1700-1705.
Yu, L., "Amorphous pharmaceutical solids: preparation, characterization and stabilization", Adv Drug Deliv Rev, 2001, 48(1), pp. 27-42.
Yuan et al., Expression, Purification, and Partial Characterization of HCV RNA Polymerase. Biochemical and Biophysical Research Communications 1997, vol. 232, No. 1, pp. 231-235.
Yuodka et al., "Oligonucleotides and Polynucleotides. XXVI. Synthesis of Esters of Nucleotidyl- and Oligonucleotidyl-(5'-N)-(Amino Acid)S and- Peptides," Soviet Journal of Bioorganic Chemistry 1976, vol. 2, No. 11, pp. 1089-1094, Translated from Russian.
Zemlicka J. Lipophilic phosphoramidates as antiviral pronucleotides. Biochimica et Biophysica Acta 1587, (2002), pp. 276-286.
Zheng et al., Syntheses and initial evaluation of a series of indolo-fused heterocyclic inhibitors of the polymerase enzyme (NS5B) of the hepatitis C virus, Bioorganic & Medicinal Chemistry Letters, 21, (2011), pp. 2925-2929.
Zhong et al., Identification and Characterization of an RNA-Dependent RNA Polymerase Activity within the Nonstructural Protein 5B Region of Bovine Viral Diarrhea Virus. Journal of Virology 1998, vol. 72, No. 11, pp. 9365-9369.
Zhou et al., "Physical Stability of Amorphous Pharmaceuticals: Importance of Configurational Thermodynamic Quantities and Molecular Mobility", Journal of Pharmaceutical Sciences, 2002, 91(8), pp. 1863-1872.
Zon, G., 4 Cyclophosphamide Analogues. Progress in Medicinal Chemistry 1982, vol. 19, pp. 205-246.
BRPTO's Rejection Decision for Brazilian Application No. BR 112016003644-1 dated Jun. 3, 2020. 9 pages.
Byrn et al., Pharmaceutical Solids: A Strategic Approach to Regulatory Considerations, Pharmaceutical Research, vol. 12, No. 7, 1995, pp. 945-954.
Final Rejection for Korean Patent Application No. 10-2016-7007662 dated Dec. 4, 2020. 6 pages.

* cited by examiner

COMBINATION FORMULATION OF TWO ANTIVIRAL COMPOUNDS

CROSS-REFERENCE TO RELATED APPLICATIONS

This application is a continuation of U.S. patent application Ser. No. 16/669,063, filed Oct. 30, 2019, now abandoned, which is a continuation of U.S. patent application Ser. No. 16/124,111, filed Sep. 6, 2018, now abandoned, which is a continuation of U.S. patent application Ser. No. 15/670,283, filed Aug. 7, 2017, now U.S. Pat. No. 10,086,011, which is a divisional of U.S. patent application Ser. No. 15/282,128, filed Sep. 30, 2016, now U.S. Pat. No. 9,757,406, which is a continuation of U.S. patent application Ser. No. 14/168,340, filed Jan. 30, 2014, now abandoned, which claims the benefit under 35 U.S.C. § 119(e) to U.S. Provisional Application No. 61/870,712, filed Aug. 27, 2013, U.S. Provisional Application No. 61/898,690, filed Nov. 1, 2013, and U.S. Provisional Application No. 61/907,308, filed Nov. 21, 2013, each of which is incorporated herein by reference in its entirety.

BACKGROUND

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

The compounds methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate, designated herein as Compound I and (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino) propanoate, designated herein as sofosbuvir, are known to be an effective anti-HCV agents, as described for example in U.S. Pat. Nos. 7,964,580 and 8,575,135. However, the therapeutic benefits of the administration of Compound I and crystalline sofosbuvir were not heretofore known.

SUMMARY

Compound I (see, for example, WO 2013/075029 and U.S. Pat. No. 8,575,135) has the following chemical structure:

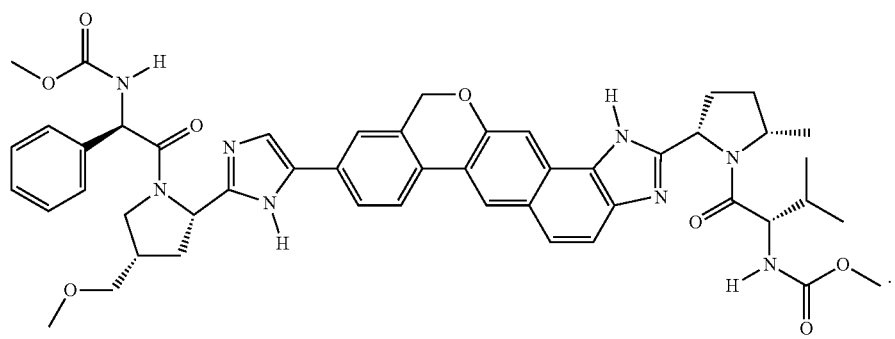

Sofosbuvir is a selective inhibitor of non-structural protein 5B (NS5B) (see, for example, WO 2010/132601 and U.S. Pat. No. 7,964,580). The chemical name of sofosbuvir is (S)-isopropyl 2-(((S)-(((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphoryl)amino)propanoate:

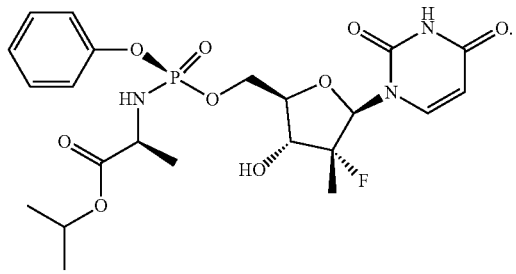 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

Aspects of the disclosure relate to pharmaceutical composition comprising: a) an effective amount of Compound I, wherein the Compound I is substantially amorphous; and b) an effective amount of sofosbuvir, wherein the sofosbuvir is substantially crystalline.

Further aspects of the disclosure relate to pharmaceutical dosage forms and tablets. The disclosure also provides methods for using the combination in the treatment of hepatitis C.

It is contemplated that the solid dispersions disclosed herein would demonstrate one or more of increased bioavailability, elimination of or reduced food-effect, reduced negative drug-drug interaction with acid suppressive therapies, reduced variability across patient populations, and/or improved dose linearity at higher doses when compared with administration of Compound I and/or sofosbuvir alone.

DETAILED DESCRIPTION

1. Definitions

As used in the present specification, the following words and phrases are generally intended to have the meanings as set forth below, except to the extent that the context in which they are used indicates otherwise.

As used herein, the term "about" used in the context of quantitative measurements means the indicated amount ±10%. For example, "about 2:8" would mean 1.8-2.2:7.2-8.8.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

The term "substantially amorphous" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in amorphous form. "Substantially amorphous" can also refer to material which has no more than about 20% crystallinity, or no more than about 10% crystallinity, or no more than about 5% crystallinity, or no more than about 2% crystallinity.

The term "substantially crystalline" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in crystalline form. "Substantially crystalline" can also refer to material which has no more than about 20%, or no more than about 10%, or no more than about 5%, or no more than about 2% in the amorphous form.

The term "polymer matrix" as used herein is defined to mean compositions comprising one or more polymers in which the active agent is dispersed or included within the matrix.

The term "solid dispersion" refers to the dispersion of one or more active agents in a polymer matrix at solid state prepared by a variety of methods, including spray drying, the melting (fusion), solvent, or the melting-solvent method.

The term "amorphous solid dispersion" as used herein, refers to stable solid dispersions comprising an amorphous active agent and a polymer. By "amorphous active agent," it is meant that the amorphous solid dispersion contains active agent in a substantially amorphous solid state form.

The term "pharmaceutically acceptable" indicates that the material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "carrier" refers to a glidant, diluent, adjuvant, excipient, or vehicle with which the compound is administered. Examples of carriers are described herein and also in "Remington's Pharmaceutical Sciences" by E. W. Martin.

The term "polymer" refers to a chemical compound or mixture of compounds consisting of repeating structural units created through a process of polymerization. Suitable polymers useful in this invention are described throughout.

The term "pharmaceutically acceptable polymer" refers to a polymer that does not have properties that would cause a reasonably prudent medical practitioner to avoid administration of the material to a patient, taking into consideration the disease or conditions to be treated and the respective route of administration.

The term "diluent" refers to chemical compounds that are used to dilute the compound of interest prior to delivery. Diluents can also serve to stabilize compounds. Non-limiting examples of diluents include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "binder" when used herein relates to any pharmaceutically acceptable film which can be used to bind together the active and inert components of the carrier together to maintain cohesive and discrete portions. Non-limiting examples of binders include hydroxypropylcellulose, hydroxypropylmethylcellulose, povidone, copovidone, and ethyl cellulose.

The term "disintegrant" refers to a substance which, upon addition to a solid preparation, facilitates its break-up or disintegration after administration and permits the release of an active ingredient as efficiently as possible to allow for its rapid dissolution. Non-limiting examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

The term "lubricant" refers to an excipient which is added to a powder blend to prevent the compacted powder mass from sticking to the equipment during the tabletting or encapsulation process. It aids the ejection of the tablet form the dies, and can improve powder flow. Non-limiting examples of lubricants include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

The term "film coating" refers to a thin, uniform, film on the surface of a substrate (e.g. tablet). Film coatings are particularly useful for protecting the active ingredient from photolytic degradation. Non-limiting examples of film coatings include polyvinylalcohol based, hydroxyethylcellulose, hydroxypropylmethylcellulose, sodium carboxymethylcellulose, polyethylene glycol 4000 and cellulose acetate phthalate film coatings.

The term "glidant" as used herein is intended to mean agents used in tablet and capsule formulations to improve flow-properties during tablet compression and to produce an anti-caking effect. Non-limiting examples of glidants include colloidal silicon dioxide, talc, fumed silica, starch, starch derivatives, and bentonite.

The term "effective amount" refers to an amount that is sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "sustained virologic response" refers to the absence of detectable RNA (or wherein the RNA is below the limit of detection) of a virus (i.e. HCV) in a patient sample (i.e. blood sample) for a specific period of time after discontinuation of a treatment. For example, a SVR at 4 weeks indicates that RNA was not detected or was below the limit of detection in the patient at 4 weeks after discontinuing HCV therapy.

The term "% w/w" as used herein refers to the weight of a component based on the total weight of a composition comprising the component. For example, if component A is present in an amount of 50% w/w in a 100 mg composition, component A is present in an amount of 50 mg.

2. Pharmaceutical Compositions

The pharmaceutical compositions of the disclosure provide for a combination of an effective amount of Compound I and an effective amount of sofosbuvir wherein the sofosbuvir is substantially crystalline.

A. Compound I

Compound I has previously been described (see, for example, WO 2013/075029) and can be prepared by methods described therein. In one embodiment, the pharmaceutical composition comprises Compound I formulated as a solid dispersion dispersed within a polymer matrix formed by a pharmaceutically acceptable polymer. The starting material of the solid dispersion can be a variety of forms of Compound I including crystalline forms, amorphous form, salts thereof, solvates and free base. In one embodiment, the Compound I is substantially amorphous. In certain embodiments, the Compound I is the free base.

Various techniques are well known in the art for preparing solid dispersions including, but not limited to melt-extrusion, spray-drying, lyophilization, and solution-evaporation.

Melt-extrusion is the process of embedding a compound in a thermoplastic carrier. The mixture is processed at elevated temperatures and pressures, which disperses the compound in the matrix at a molecular level to form a solid solution. Extruded material can be further processed into a variety of dosage forms, including capsules, tablets and transmucosal systems.

For the solution-evaporation method, the solid dispersion can be prepared by dissolving the compound in a suitable liquid solvent and then incorporating the solution directly into the melt of a polymer, which is then evaporated until a clear, solvent free film is left. The film is further dried to constant weight.

For the lyophilization technique, the compound and carrier can be co-dissolved in a common solvent, frozen and sublimed to obtain a lyophilized molecular dispersion.

For spray dried solid dispersions, the solid dispersion can be made by a) mixing the compound and polymer in a solvent to provide a feed solution; and b) spray drying the feed solution to provide the solid dispersion.

Spray dried solid dispersions of Compound I provide improved in vivo and in vitro performance and manufacturability/scalability relative to the other formulation approaches, such as wet and dry granulation formulations. In one embodiment, the Compound I is substantially amorphous. In certain embodiments, the Compound I is the free base. In other embodiments, the Compound I is the amorphous free base.

The selection of the polymer for the solid dispersion is based on the stability and physical characteristics of Compound I in the solution. Polyvinyl caprolactam-polyvinyl acetate-polyethylene glycol (Soluplus®) and copovidone solid dispersions both showed adequate stability and physical characteristics. In one embodiment, the polymer used in the solid dispersion is polyvinyl caprolactam-polyvinyl acetate-polyethylene glycol (Soluplus®) or copovidone. Accordingly, in a certain embodiment, the polymer used in the solid dispersion is polyvinyl caprolactam-polyvinyl acetate-polyethylene glycol (Soluplus®). In another embodiment, the polymer used in the solid dispersion is copovidone.

In one embodiment, the polymer used in the solid dispersion of Compound I is hydrophilic. Non-limiting examples of hydrophilic polymers include polysaccharides, polypeptides, cellulose derivatives such as methyl cellulose, sodium carboxymethylcellulose, hydroxyethylcellulose, ethylcellulose, hydroxypropyl methylcellulose acetate-succinate, hydroxypropyl methylcellulose phthalate, cellulose acetate phthalate, and hydroxypropylcellulose, povidone, copovidone, hypromellose, pyroxylin, polyethylene oxide, polyvinyl alcohol, and methacrylic acid copolymers.

In a further embodiment, the polymer is non-ionic. Non-ionic polymers showed benefits in screening solubility experiments. Non-limiting examples of non-ionic polymers include hypromellose, copovidone, povidone, methyl cellulose, hydroxyethyl cellulose, hydroxypropyl cellulose, ethylcellulose, pyroxylin, polyethylene oxide, polyvinyl alcohol, polyethylene glycol, and polyvinyl caprolactam-polyvinyl acetate-polyethylene glycol (Soluplus®).

In another embodiment, the polymer is ionic. Examples of ionic polymers include hydroxypropyl methylcellulose acetate-succinate, hydroxypropyl methylcellulose phthalate, cellulose acetate phthalate, and methacrylic acid copolymers.

In a further embodiment, the polymer is selected from the group consisting of hypromellose, hydroxypropyl cellulose, Soluplus®, copovidone, and povidone. In a specific embodiment, the polymer is copovidone. In another specific embodiment, the polymer is polyvinyl caprolactam-polyvinyl acetate-polyethylene glycol (Soluplus®).

In certain embodiments, the weight ratio of Compound I to polymer is from about 5:1 to about 1:5. In further embodiments, the weight ratio of Compound I to polymer is about 5:1 to about 1:4, or from about 5:1 to about 1:3, or from about 5:1 to about 1:2, or from about 2:1 to about 1:2, or from about 2:1 to about 1:1. In a specific embodiment, the weight ratio of Compound I to polymer is about 1:1. In another embodiment, the weight ratio of Compound I to polymer is about 1:2. In further embodiments, the weight ratio of Compound I to polymer is about 5:1, 4:1, 3:1, 2:1, 1:1, 1:5, 1:4, 1:3, or 1:2.

The solid dispersion of Compound I may be present in the pharmaceutical composition in a therapeutically effective amount. In some embodiments, the pharmaceutical composition comprises from about 1% to about 40% w/w of the solid dispersion of Compound I. In further embodiments, the composition comprises from about 1% to about 35% w/w, or from about 1% to about 30% w/w, or from about 1% to about 25% w/w, or from about 1% to about 20% w/w of the solid dispersion of Compound I. In a specific embodiment, the pharmaceutical composition comprises about 8.3% w/w of the solid dispersion of Compound I. In a further specific embodiment, the pharmaceutical composition comprises about 20% of the solid dispersion of Compound I. In further embodiments, the pharmaceutical composition comprises about 1% w/w, about 5% w/w, about 8% w/w, about 10% w/w, about 20% w/w, about 25% w/w, about 30% w/w, about 35% w/w, about 40% w/w, or about 45% w/w of the solid dispersion of Compound I.

Compound I may be present in the pharmaceutical composition in a therapeutically effective amount. In some embodiments, the pharmaceutical composition comprises from about 0.1% to about 50% w/w of Compound I. In further embodiments, the composition comprises from about 0.1% to about 40% w/w, or from about 0.1% to about 35% w/w, or from about 0.5% to about 25% w/w, or from about 0.5% to about 20% w/w, or from about 0.5% to about 15% w/w, or from about 0.5% to about 10% w/w of Compound I. In further embodiments, the pharmaceutical composition comprises about 0.1% w/w, 0.5% w/w, 1% w/w, 2% w/w, 4% w/w, 5% w/w, about 7% w/w, about 10% w/w, about 12% w/w, about 15% w/w, about 17% w/w, about 20% w/w, about 25% w/w, about 30% w/w, about 35% w/w, about 40% w/w, or about 45% w/w of Compound I. In a specific embodiment, the pharmaceutical composition comprises about 4.2% w/w of Compound I. In another specific embodiment, the pharmaceutical composition comprises about 10% w/w of Compound I.

As noted above, after the Compound I is mixed with the polymer, the mixture can then be solubilized in a solvent. It is within the skill of those in the art to select an appropriate solvent based on the drug and/or polymer properties such as solubility, glass transition temperature, viscosity, and molecular weight. Acceptable solvents include but are not limited to, water, acetone, methyl acetate, ethyl acetate, chlorinated solvents, ethanol, dichloromethane, and methanol. In one embodiment, the solvent is selected from the group consisting of ethanol, dichloromethane, and methanol. In a further embodiment, the solvent is ethanol or methanol. In a specific embodiment, the solvent is ethanol.

Upon solubilization of the compound and polymer mixture with the solvent, the mixture may then be spray dried. Spray drying is a well known process wherein a liquid feedstock is dispersed into droplets into a drying chamber along with a heated process gas stream to aid in solvent removal and to produce a powder product. Suitable spray drying parameters are known in the art, and it is within the knowledge of a skilled artisan in the field to select appropriate parameters for spray drying. The target feed concentration is generally about 10 to about 50% with a target of about 20% and a viscosity of about 1 to about 300 cP, or about 1 to about 80 cP, or about 4 to 60 cP. The inlet temperature of the spray dry apparatus is typically about 50-190° C., while the outlet temperature is about 30-90° C. The two fluid nozzle and hydrolic pressure nozzle can be used to spray dry Compound I. The two fluid nozzle gas flow can be about 1-100 kg/hr, the hydrolic pressure nozzle flow can be about 15-300 kg/hr, and the chamber gas flow may be about 25-2500 kg/hr. The spray-dried material typically has particle size ($D_{90}$) less than about 200 µm, or less than about 120 µm, or about 70 to about 80 µm, or in some instances, less than about 25 µm. In some instances, a milling step may be used, if desired to further reduce the particle size. Further descriptions of spray drying methods and other techniques for forming amorphous dispersions are provided in U.S. Pat. No. 6,763,607 and U.S. Pat. Pub. No. 2006-0189633, the entirety of each of which is incorporated herein by reference.

Spray drying out of ethanol resulted in high yields across a wide range of spray-drying outlet temperatures with no material accumulation on the spray dry chamber. Furthermore, Compound I demonstrated good chemical stability in the ethanolic feed solution.

B. Sofosbuvir

Sofosbuvir has previously been described in U.S. Pat. No. 7,964,580 and U.S. Pat. Pub. Nos: 2010/0016251, 2010/0298257, 2011/0251152 and 2012/0107278. The sofosbuvir is provided as substantially crystalline in the pharmaceutical compositions described herein. Examples of preparing crystalline forms of sofosbuvir are disclosed in U.S. Pat. Pub. Nos: 2010/0298257 and 2011/0251152, both of which are incorporated by reference. Crystalline forms, Forms 1-6, of sofosbuvir are described in U.S. Pat. Pub. Nos.: 2010/0298257 and 2011/0251152, both of which are incorporated by reference. Forms 1-6 of sofosbuvir have the following characteristic X-ray powder diffraction (XRPD) pattern 2θ-values measured according to the XRPD methods disclosed therein:

(1) 2θ-reflections at about: 7.5, 9.6, and 18.3 °2θ±0.2 (Form 1);
(2) 2θ-reflections at about: 5.0, 7.3, and 18.1 °2θ±0.2 (Form 1);
(3) 2θ-reflections at about: 6.9, 24.7, and 25.1 °2θ±0.2 (Form 2);
(4) 2θ-reflections at about: 19.7, 20.6, and 24.6 °2θ±0.2 (Form 3);
(5) 2θ-reflections at about: 5.0, 6.8, and 24.9 °2θ±0.2 (Form 4);
(6) 2θ-reflections at about: 5.2, 6.6, and 19.1 °2θ±0.2 (Form 5); and
(7) 2θ-reflections at about: 6.1, 20.1, and 20.8 °2θ±0.2 (Form 6).

Form 6, as described in the patent publications above, may be referred to as Form 2, such as for example, by the Food and Drug Administration. Forms 1 and 6 are alternatively characterized by the following characteristic XRPD pattern 2θ-values as measured according to the methods disclosed in U.S. Pat. Pub. Nos.: 2010/0298257 and 2011/0251152:

(1) 2θ-reflections at about: 5.0 and 7.3 °2θ±0.2 (Form 1); and
(2) 2θ-reflections at about: 6.1 and 12.7 °2θ±0.2 (Form 6).

In one embodiment, the crystalline sofosbuvir has XRPD 2θ-reflections (°2θ±0.2) at about:

(1) 7.5, 9.6, and 18.3 °2θ±0.2; (Form 1A)
(2) 5.0, 7.3, and 18.1 °2θ±0.2; (Form 1B)
(3) 6.9, 24.7, and 25.1 °2θ±0.2; (Form 2)
(4) 19.7, 20.6, and 24.6 °2θ±0.2; (Form 3)
(5) 5.0, 6.8, and 24.9 °2θ±0.2; (Form 4)
(6) 5.2, 6.6, and 19.1 °2θ±0.2; (Form 5) or
(7) 6.1, 20.1, and 20.8 °2θ±0.2; (Form 6).

In certain embodiments, the crystalline sofosbuvir has XRPD 2θ-reflections at about:

(1) 5.2, 7.5, 9.6, 16.7, 18.3, and 22.2 °2θ±0.2 (Form 1);
(2) 5.0, 7.3, 9.4, and 18.102θ±0.2 (Form 1);
(3) 4.9, 6.9, 9.8, 19.8, 20.6, 24.7, 25.1, and 26.1 °2θ±0.2 (Form 2);
(4) 6.9, 9.8, 19.7, 20.6, and 24.6 °2θ±0.2 (Form 3);
(5) 5.0, 6.8, 19.9, 20.6, 20.9, and 24.9 °2θ±0.2 (Form 4);
(6) 5.2, 6.6, 7.1, 15.7, 19.1, and 25.0 °2θ±0.2 (Form 5); or
(7) 6.1, 8.2, 10.4, 12.7, 17.2, 17.7, 18.0, 18.8, 19.4, 19.8, 20.1, 20.8, 21.8, and 23.3 °2θ±0.2 (Form 6).

In a further embodiment, crystalline sofosbuvir has XRPD 2θ-reflections at about: 6.1, 8.2, 10.4, 12.7, 17.2, 17.7, 18.0, 18.8, 19.4, 19.8, 20.1, 20.8, 21.8, and 23.3 °2θ±0.2. In yet a further embodiment, crystalline sofosbuvir has XRPD 2θ-reflections at about: 6.1 and 12.7 °2θ±0.2.

Sofosbuvir may be present in the pharmaceutical composition in a therapeutically effective amount. In some embodiments, the pharmaceutical compositions comprises from about 10% to about 70% w/w of sofosbuvir. In further embodiments, the composition comprises from about 15% to about 65% w/w, or from about 20% to about 60% w/w, or from about 25% to about 55% w/w, or from about 30% to about 50% w/w, or from about 35% to about 45% w/w of sofosbuvir. In further embodiments, the pharmaceutical composition comprises about 10% w/w, about 15% w/w, about 20% w/w, about 25% w/w, about 30% w/w, about 35% w/w, about 40%, about 45% w/w, about 50% w/w, about 55% w/w, about 60% w/w, about 65% w/w, or about 70% w/w, or about 75% w/w. In a specific embodiment, the pharmaceutical composition comprises about 40% w/w of sofosbuvir. In another specific embodiment, the pharmaceutical composition comprises about 67% w/w of sofosbuvir.

C. Excipients

The pharmaceutical compositions provided in accordance with the present disclosure are usually administered orally. This disclosure therefore provides pharmaceutical compositions that comprise a solid dispersion comprising Compound I and sofosbuvir as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses by oral administration. Administration may be via capsule, tablet, or the like. In one embodiment, the Compound I is in the form of a tablet. In a further embodiment, the tablet is a compressed tablet. In making the pharmaceutical compositions that include the solid described herein, the active ingredient is usually diluted by an excipient and/or enclosed within such a carrier that can be in the form of a capsule, tablet, sachet, paper or other container. When the excipient serves as a diluent, it can be in the form of a solid, semi-solid or liquid material (as above), which acts as a vehicle, carrier or medium for the active ingredient.

The pharmaceutical composition may be formulated for immediate release or sustained release. A "sustained release formulation" is a formulation which is designed to slowly release a therapeutic agent in the body over an extended period of time, whereas an "immediate release formulation" is a formulation which is designed to quickly release a therapeutic agent in the body over a shortened period of time. In some cases the immediate release formulation may be coated such that the therapeutic agent is only released once it reached the desired target in the body (e.g. the stomach). In a specific embodiment, the pharmaceutical composition is formulated for immediate release.

The pharmaceutical composition may further comprise pharmaceutical excipients such as diluents, binders, fillers, glidants, disintegrants, lubricants, solubilizers, and combinations thereof. Some examples of suitable excipients are described herein. When the pharmaceutical composition is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In one embodiment, the pharmaceutical composition comprises a diluent selected from the group consisting of dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof.

In further embodiments, the pharmaceutical composition comprises lactose monohydrate in an amount from about 0 to about 60% w/w, or from about 0 to about 45% w/w, or from about 5 to about 40% w/w, or from about 5 to about 35% w/w, or from about 5 to about 25% w/w, or from about 10 to about 20% w/w. In specific embodiments, the lactose monohydrate is present at about 0% w/w, about 5% w/w, at about 10% w/w, at about 15% w/w, at about 20% w/w, at about 25% w/w, at about 30% w/w, at about 35% w/w, at about 40% w/w, at about 45% w/w, or at about 50% w/w.

In yet further embodiments, the pharmaceutical composition comprises microcrystalline cellulose in an amount from about 1 to about 40% w/w, or from about 1 to about 35% w/w, or from about 5% to about 35% w/w, or from about 15 to about 35% w/w, or from about 20 to about 35% w/w. In specific embodiments, the microcrystalline cellulose is present in an amount of about 5%, or about 10%, or about 15%, or about 20%, or about 25%, or about 30%, or about 35%, or about 40% w/w.

In other embodiments, the pharmaceutical composition comprises a disintegrant selected from the group consisting of croscarmellose sodium, crospovidone, microcrystalline cellulose, modified corn starch, povidone, pregelatinized starch, sodium starch glycolate, and combinations thereof.

In certain embodiments, the pharmaceutical composition comprises croscarmellose sodium in an amount from about 1 to about 20% w/w, or from about 1 to about 15% w/w, or from about 1 to about 10% w/w, or from about 1 to about 8% w/w, or from about 2 to about 8% w/w. In specific embodiments, the croscarmellose sodium is present in an amount of about 1%, or about 3%, or about 6%, or about 8%, or about 10%, or about 13%, or about 15% w/w. In a further specific embodiment, the croscarmellose sodium is in an amount of about 5% w/w. In another specific embodiment, the croscarmellose sodium is in an amount of about 3% w/w.

In other embodiments, the pharmaceutical composition comprises a glidant selected from the group consisting of colloidal silicon dioxide, talc, starch, starch derivatives, and combinations thereof.

In further embodiments, the pharmaceutical composition comprises colloidal silicon dioxide in an amount from about 0 to about 5% w/w, or from about 0 to about 4.5% w/w, or from about 0 to about 4% w/w, or from about 0.5 to about 5.0% w/w, or from about 0.5 to about 3% w/w, or from about 0.5 to about 2% w/w, or from about 0.5 to about 1.5% w/w. In specific embodiments, the colloidal silicon dioxide is present in an amount of about 0% w/w, 0.1% w/w, 0.5% w/w, 0.75% w/w, 1.25% w/w, 1.5% w/w, or 2% w/w. In a further specific embodiment, the colloidal silicon dioxide is present in an amount of about 1% w/w. In another specific embodiment, the colloidal silicon dioxide is present in an amount of about 0% w/w.

In other embodiments, the pharmaceutical composition comprises a lubricant selected from the group consisting of calcium stearate, magnesium stearate, polyethylene glycol, sodium stearyl fumarate, stearic acid, talc, and combinations thereof.

In further embodiments, the pharmaceutical composition comprises magnesium stearate in an amount from about 0.1 to about 3% w/w, or from about 0.1 to about 2.5% w/w, or from about 0.5 to about 3% w/w, or from about 0.5 to about 2.5% w/w, or from about 0.5 to about 2% w/w, or from about 1 to about 3% w/w, or from about 1 to about 2% w/w. In specific embodiments, the magnesium stearate is present in an amount of about 0.1%, or about 0.5, or about 1%, or about 1.5%, or about 2%, or about 2.5%, or about 3% w/w. In a further specific embodiment, the magnesium stearate is in an amount of about 1.5% w/w.

In one embodiment, the pharmaceutical composition comprises a) about 30 to about 50% w/w of sofosbuvir and b) about 1 to about 45% w/w of the solid dispersion comprising Compound I. In a related embodiment, the composition comprises a) about 40% w/w of sofosbuvir and b) about 20% w/w of the solid dispersion comprising Compound I. In yet a further related embodiment, the composition further comprises a) about 5 to about 40% w/w microcrystalline cellulose, b) about 1 to about 10% w/w croscarmellose sodium, and c) about 0.1 to about 3% w/w magnesium stearate. In a another embodiment, the composition comprises a) about 67% w/w of sofosbuvir and b) about 8% w/w of the solid dispersion comprising Compound I. In yet another embodiment, the composition further comprises a) about 5 to about 25% w/w microcrystalline cellulose, b) about 1 to about 10% w/w croscarmellose sodium, and c) about 0.1 to about 3% w/w magnesium stearate.

3. Pharmaceutical Dosage Forms

The disclosure provides for tablets, pills, and the like, comprising the pharmaceutical compositions or dosage forms described herein. The tablets or pills of the present disclosure may be coated to provide a dosage form affording the advantage of prolonged action or to protect from the acid conditions of the stomach. The tablets may also be formulated for immediate release as previously described. In certain embodiments, the tablet comprises a film coating. A film coating is useful for limiting photolytic degradation. Suitable film coatings are selected by routine screening of commercially available preparations. In one embodiment, the film coating is a polyvinylalcohol-based coating.

The tablets may be formulated into a monolayer or bilayer tablet. Typically, monolayer tablet comprise the active ingredients (i.e., Compound I and sofosbuvir) co-mixed in a single uniform layer. For making monolayer tablets, exemplary methods include, but are not limited to coblend (or bi-granulation) and codry granulation. Coblend granulation is a multi-step process consisting of separate dry granulations for each active ingredient with excipients followed by the blending of the two granulations together. Codry granulation comprises dry granulating both active ingredients and excipients together.

Bilayer tablets comprise the active ingredients (i.e., Compound I and sofosbuvir) in separate layers and can be made by making a blend comprising excipients and one active ingredient (i.e., Compound I), and making a separate blend comprising the second active ingredient (i.e., sofosbuvir) and excipients. One blend may then be precompressed, and the second blend may then be added on top of the first precompressed blends. The resulting tablet comprises two separate layers, each layer comprising a different active ingredient.

In one embodiment, the tablet comprises a) about 30 to about 70% w/w of sofosbuvir and b) about 1 to about 45% w/w of the solid dispersion comprising Compound I. In a related embodiment, the tablet comprises a) about 40% w/w of sofosbuvir and b) about 20% w/w of the solid dispersion comprising Compound I. In a related embodiment, the tablet comprises a) about 67% w/w of sofosbuvir and b) about 8% w/w of the solid dispersion comprising Compound I. In a further embodiment, the tablet comprises a) about 300 to about 500 mg of sofosbuvir and b) about 5 to about 150 mg of Compound I. In a yet further embodiment, the tablet comprises a) about 400 mg of sofosbuvir and b) about 100 mg of Compound I. In a yet further embodiment, the tablet comprises a) about 400 mg of sofosbuvir and b) about 25 mg of Compound I. In related embodiment, the tablet further comprises a) about 5 to about 40% w/w microcrystalline cellulose, b) about 1 to about 10% w/w croscarmellose sodium, and c) about 0.1 to about 3% w/w magnesium stearate. In another related embodiment, the tablet further comprises a) about 15 to about 40% w/w microcrystalline cellulose, b) about 1 to about 10% w/w croscarmellose sodium, and c) about 0.1 to about 3% w/w magnesium stearate.

In some embodiments, the pharmaceutical compositions as described herein are formulated in a unit dosage or pharmaceutical dosage form. The term "unit dosage forms" or "pharmaceutical dosage forms" refers to physically discrete units suitable as unitary dosages for human patients and other mammals, each unit containing a predetermined quantity of active material calculated to produce the desired therapeutic effect, in association with a suitable pharmaceutical excipient (e.g., a tablet or capsule). The compounds are generally administered in a pharmaceutically effective amount. In some embodiments, each dosage unit contains from 1 mg to 2 g of Compound I. In other embodiments, the pharmaceutical dosage form comprises from about 1 to about 450 mg, or about 5 to about 300 mg, or about 5 to about 150 mg, or about 5 to about 100 mg, or about 5 to about 50 mg, or about 5 to about 25 mg, or about 50 to about 150 mg, or about 5 to about 10 mg, or about 70 to about 120 mg, or about 90 to about 110 mg. In specific embodiments, the pharmaceutical dosage form comprises about 5, or about 10, or about 15, or about 25, or about 50, or about 100, or about 150, or about 200, or about 250, or about 300, or about 450, or about 600 mg of Compound I. In a further specific embodiment, the pharmaceutical dosage form comprises about 25 mg of Compound I. In yet a further specific embodiment, the pharmaceutical dosage form comprises about 100 mg of Compound I.

In other embodiments, the pharmaceutical dosage form comprises from about 1 mg to about 3 g of sofosbuvir. In other embodiments, the pharmaceutical dosage form comprises from about 1 to about 800 mg, or about 100 to about 700 mg, or about 200 to about 600 mg, or about 300 to about 500 mg, or about 350 to about 450 mg, of sofosbuvir. In specific embodiments, the pharmaceutical dosage form comprises about 50, or about 100, or about 150, or about 200, or about 250, or about 300, or about 350, or about 450, or about 500, or about 550, or about 600, or about 650, or about 700, or about 750, or about 800 mg of sofosbuvir. In a further specific embodiment, the pharmaceutical dosage form comprises about 400 mg of sofosbuvir. It will be understood, however, that the amount of Compound I and/or sofosbuvir actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

In a specific embodiment, the pharmaceutical dosage form comprises about 400 mg of sofosbuvir and about 100 mg of Compound I. In another specific embodiment, the pharmaceutical dosage form comprises about 400 mg of sofosbuvir and about 25 mg of Compound I.

In one embodiment, the pharmaceutical composition, or alternatively, the pharmaceutical dosage form or tablet comprises about 100 mg of Compound I formulated in a solid dispersion comprising a polymer:Compound I ratio of 1:1, about 400 mg crystalline sofosbuvir, microcrystalline cellulose in an amount from about 5 to about 40% w/w, croscarmellose sodium in an amount from about 1 to about 10% w/w, and magnesium stearate in an amount from about 0.1 to about 3% w/w. In one embodiment, the polymer is copovidone.

In another embodiment, the pharmaceutical composition, or alternatively, the pharmaceutical dosage form or tablet comprises about 25 mg of Compound I formulated in a solid dispersion comprising a polymer:Compound I ratio of 1:1, about 400 mg crystalline sofosbuvir, microcrystalline cellulose in an amount from about 5 to about 25% w/w, croscarmellose sodium in an amount from about 1 to about 10% w/w, and magnesium stearate in an amount from about 0.1 to about 3% w/w. In one embodiment, the polymer is copovidone.

In further embodiments, the pharmaceutical composition, pharmaceutical dosage form, or tablet as described herein is free of negative drug-drug interactions.

4. Methods of Use

The solid dispersions, pharmaceutical compositions, pharmaceutical dosage forms, and tablets of Compound I and sofosbuvir as described herein are administered to a patient suffering from hepatitis C virus (HCV) in a daily dose by oral administration. In one embodiment, the patient is human.

In one embodiment, the solid dispersions, pharmaceutical compositions, pharmaceutical dosage forms, and tablets of Compound I and sofosbuvir as described herein are effective in treating one or more of genotype 1 HCV infected patients, genotype 2 HCV infected patients, genotype 3 HCV infected patients, genotype 4 HCV infected patients, genotype 5 HCV infected patients, and/or genotype 6 HCV infected patients. In one embodiment, the solid dispersions, pharmaceutical compositions, pharmaceutical dosage forms, and tablets of Compound I and sofosbuvir as described herein are effective in treating genotype 1 HCV infected patients, including genotype 1a and/or genotype 1b. In another embodiment, the solid dispersions, pharmaceutical compositions, pharmaceutical dosage forms, and tablets of Compound I and sofosbuvir as described herein are effective in treating genotype 2 HCV infected patients, including genotype 2a, genotype 2b, genotype 2c and/or genotype 2d. In another embodiment, the solid dispersions, pharmaceutical compositions, pharmaceutical dosage forms, and tablets of Compound I and sofosbuvir as described herein are effective in treating genotype 3 HCV infected patients, including genotype 3a, genotype 3b, genotype 3c, genotype 3d, genotype 3e and/or genotype 3f. In another embodiment, the solid dispersions, pharmaceutical compositions, pharmaceutical dosage forms, and tablets of Compound I and sofosbuvir as described herein are effective in treating genotype 4 HCV infected patients, including genotype 4a, genotype 4b, genotype 4c, genotype 4d, genotype 4e, genotype 4f, genotype 4g, genotype 4h, genotype 4i and/or genotype 4j. In another embodiment, the solid dispersions, pharmaceutical compositions, pharmaceutical dosage forms, and tablets of Compound I and sofosbuvir as described herein are effective in treating genotype 5 HCV infected patients, including genotype 5a. In another embodiment, the solid dispersions, pharmaceutical compositions, pharmaceutical dosage forms, and tablets of Compound I and sofosbuvir as described herein are effective in treating genotype 6 HCV infected patients, including genotype 6a. In one embodiment, the solid dispersions, pharmaceutical compositions, pharmaceutical dosage forms, and tablets of Compound I and sofosbuvir as described herein are pangenotypic, meaning they are useful across all genotypes and drug resistant mutants thereof.

In some embodiments, the pharmaceutical composition, pharmaceutical dosage form, or tablet of Compound I and sofosbuvir as described herein is administered, either alone or in combination with one or more therapeutic agent(s) for treating HCV (such as a HCV NS3 protease inhibitor or an inhibitor of HCV NS5B polymerase), for about 24 weeks, for about 16 weeks, or for about 12 weeks or less. In further embodiments, the pharmaceutical composition, pharmaceutical dosage form, or tablet of Compound I and sofosbuvir is administered, either alone or in combination with one or more therapeutic agent(s) for treating HCV (such as a HCV NS3 protease inhibitor or an inhibitor of HCV NS5B polymerase), for about 24 weeks or less, about 22 weeks or less, about 20 weeks or less, about 18 weeks or less, about 16 weeks or less, about 12 weeks or less, about 10 weeks or less, about 8 weeks or less, about 6 weeks or less, or about 4 weeks or less. The pharmaceutical composition, pharmaceutical dosage form, or tablet may be administered once daily, twice daily, once every other day, two times a week, three times a week, four times a week, or five times a week.

In further embodiments, a sustained virologic response is achieved at about 24 weeks, at about 20 weeks, at about 16 weeks, at about 12 weeks, at about 10 weeks, at about 8 weeks, at about 6 weeks, or at about 4 weeks, or at about 4 months, or at about 5 months, or at about 6 months, or at about 1 year, or at about 2 years.

In one embodiment, the daily dose is 25 mg of Compound I and 400 mg of sofosbuvir administered in the form of a tablet. In a further embodiment, the daily dose is a tablet comprising a) about 50 to about 70% w/w of sofosbuvir, b) about 1 to about 45% w/w of the solid dispersion comprising Compound I, c) about 5 to about 25% w/w microcrystalline cellulose, d) about 1 to about 10% w/w croscarmellose sodium, and e) about 0.1 to about 3% w/w magnesium stearate.

In one embodiment, the daily dose is 100 mg of Compound I and 400 mg of sofosbuvir administered in the form of a tablet. In a further embodiment, the daily dose is a tablet comprising a) about 30 to about 50% w/w of sofosbuvir, b) about 1 to about 45% w/w of the solid dispersion comprising Compound I, c) about 5 to about 40% w/w microcrystalline cellulose, d) about 1 to about 10% w/w croscarmellose sodium, and e) about 0.1 to about 3% w/w magnesium stearate.

In further embodiments, the patient is also suffering from cirrhosis. In yet a further embodiment, the patient is not suffering from cirrhosis.

5. Combination Therapy

In the methods described herein, the method can further comprise the administration of another therapeutic agent for treating HCV and other conditions such as HIV infections. In one embodiment, non-limiting examples of suitable additional therapeutic agents include one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, the additional therapeutic agent may be selected from the group consisting of:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon;

2) ribavirin and its analogs, e.g., ribavirin (Rebetol, Copegus), and taribavirin (Viramidine);

3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, MK5172, MK6325, and MK2748;

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, BCX-4678, valopicitabine (NM-283), MK-0608, and INX-189 (now BMS986094);

7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669, PSI-7792, and GS-9190;

8) HCV NS5A inhibitors, e.g., GS-5885, AZD-2836 (A-831), BMS-790052, ACH-3102, ACH-2928, MK8325, MK4882, MK8742, PSI-461, IDX719, ABT-267 and A-689;

9) TLR-7 agonists, e.g., imiquimod, 852A, GS-9524, ANA-773, ANA-975, AZD-8848 (DSP-3025), and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin; and 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In another embodiment, the additional therapeutic agent used in combination with the pharmaceutical compositions as described herein can be any agent having a therapeutic effect when used in combination with the pharmaceutical compositions as described herein. For example, the therapeutic agent used in combination with the pharmaceutical compositions as described herein can be interferons, ribavirin analogs, NS3 protease inhibitors, NS5B polymerase inhibitors, alpha-glucosidase 1 inhibitors, hepatoprotectants, non-nucleoside inhibitors of HCV, and other drugs for treating HCV.

In certain embodiments, the additional therapeutic agent is selected from the group consisting of non-nucleoside inhibitors of HCV NS5B polymerase (ABT-072 and ABT-333), HCV NS5A inhibitors (ABT-267, ACH-3102 and ACH-2928) and HCV NS3 protease inhibitors (ABT-450 and ACH-1625).

In one embodiment, the additional therapeutic agent used in combination with the pharmaceutical compositions as described herein is a HCV NS3 protease inhibitor. Non-limiting examples include one or more compounds selected from the group consisting of:

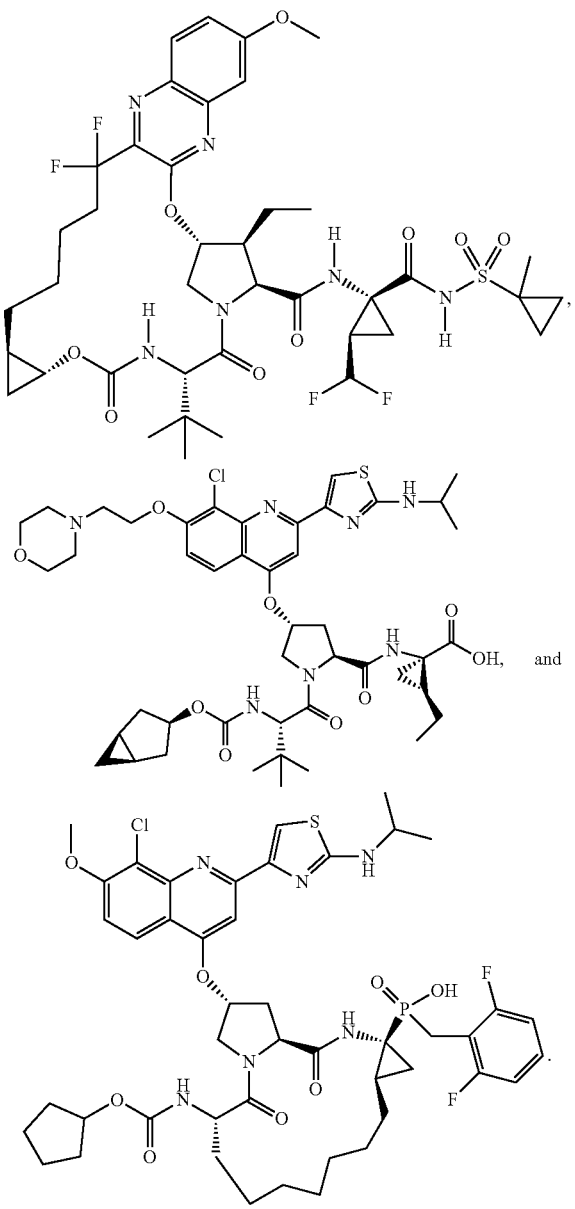

In another embodiment, the additional therapeutic agent used in combination with the pharmaceutical compositions as described herein is a cyclophillin inhibitor, including for example, a cyclophilin inhibitor disclosed in WO 2013/

185093. Non-limiting examples include one or more compounds selected from the group consisting of:

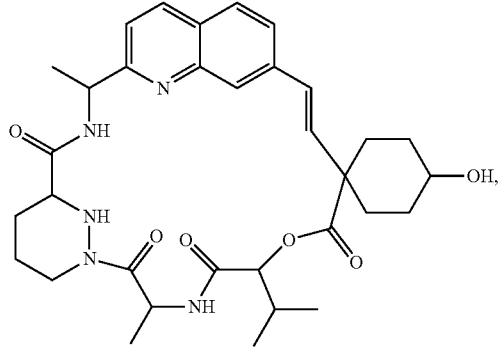

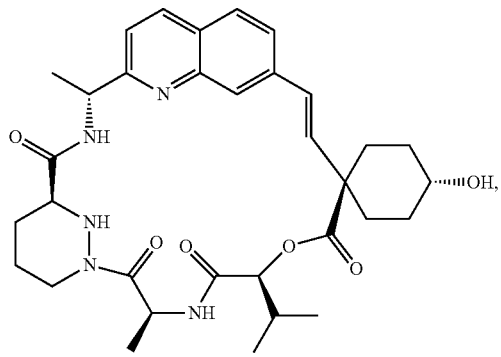

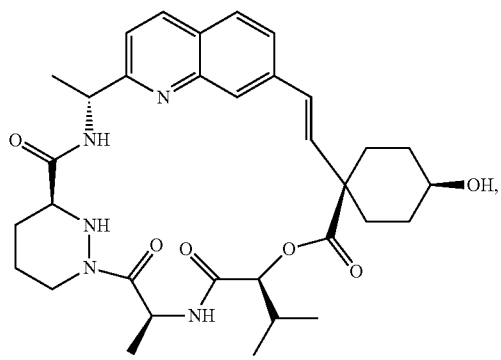

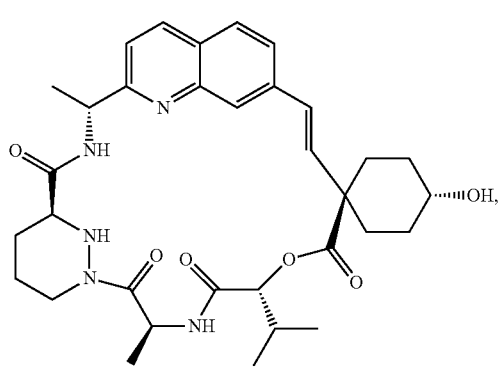

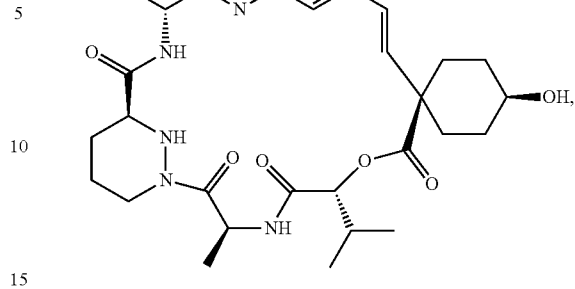

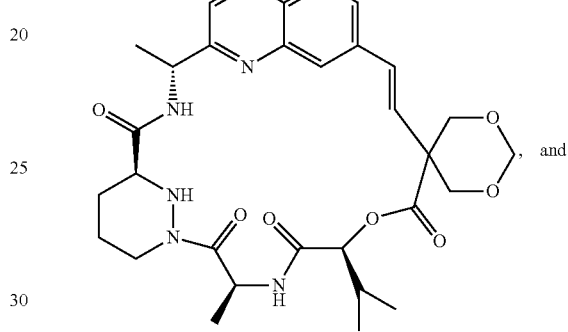

, and

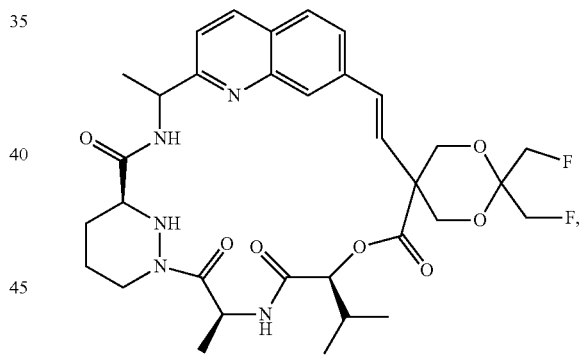

and stereoisomers and mixtures of stereoisomers thereof.

In another embodiment, the additional therapeutic agent used in combination with the pharmaceutical compositions as described herein is a non-nucleoside inhibitor of HCV NS5B polymerase. A non-limiting example includes GS-9669.

Examples of additional anti-HCV agents which can be combined with the compositions provided herein include, without limitation, the following:

A. interferons, for example, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);

B. NS5A inhibitors, for example, Compound X-1 (described below), Compound X-2 (described below), ABT-267, Compound X-3 (described below), JNJ-47910382, daclatasvir (BMS-790052), ABT-267, MK-8742, EDP-239, IDX-719, PPI-668, GSK-2336805, ACH-3102, A-831, A-689, AZD-2836 (A-831), AZD-7295 (A-689), and BMS-790052;

C. NS5B polymerase inhibitors, for example, Compound X-4 (described below), Compound X-5 (described below), ABT-333, Compound X-6 (described below), ABT-072, Compound X-7 (described below), tegobuvir (GS-9190), GS-9669, TMC647055, setrobuvir (ANA-598), filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, and BILB-1941;

D. NS3 protease inhibitors, for example, Compound X-8, Compound X-9, Compound X-10, ABT-450, Compound X-11 (described below), simeprevir (TMC-435), boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061;

E. alpha-glucosidase 1 inhibitors, for example, celgosivir (MX-3253), Miglitol, and UT-231B;

F. hepatoprotectants, e.g., IDN-6556, ME 3738, MitoQ, and LB-84451;

G. non-nucleoside inhibitors of HCV, e.g., benzimidazole derivatives, benzo-1,2,4-thiadiazine derivatives, and phenylalanine derivatives; and H. other anti-HCV agents, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811.

Compound X-1 is an inhibitor of the HCV NS5A protein and is represented by the following chemical structure:

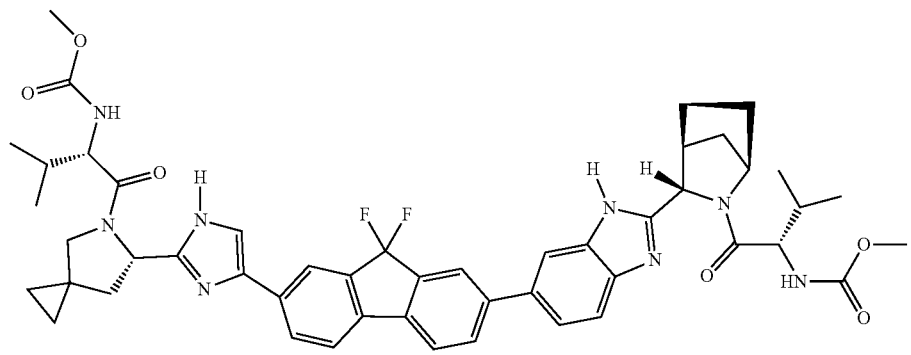

(see, e.g., U.S. Patent Application Pub. No. 2010/0310512 A1.).

Compound X-2 is an NS5A inhibitor and is represented by the following chemical structure:

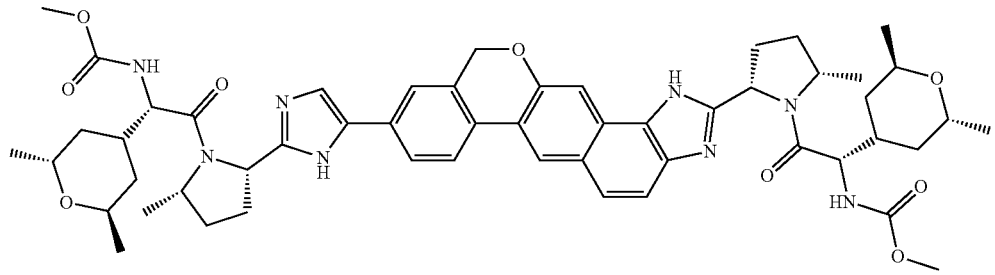

Compound X-3 is an NS5A inhibitor and is represented by the following chemical structure:

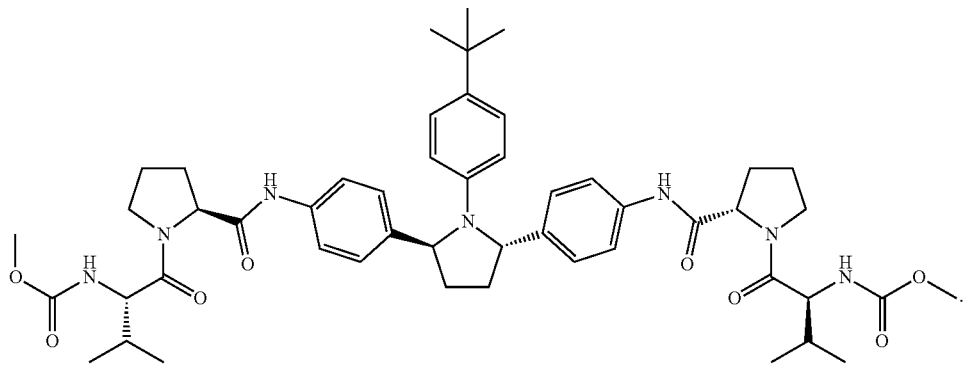 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

See U.S. Publication No. 2013/0102525 and references therein.

Compound X-4 is an NS5B Thumb II polymerase inhibitor and is represented by the following chemical structure:

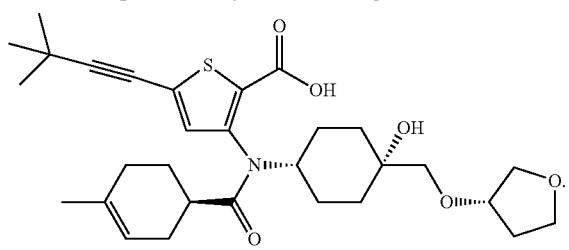 [SMILES: CC1=CC[C@H](C(=O)N(c2cc(C#CC(C)(C)C)sc2C(=O)O)[C@H]2CC[C@](O)(CO[C@H]3CCOC3)CC2)CC1]

Compound X-5 is a nucleotide inhibitor prodrug designed to inhibit replication of viral RNA by the HCV NS5B polymerase, and is represented by the following chemical structure:

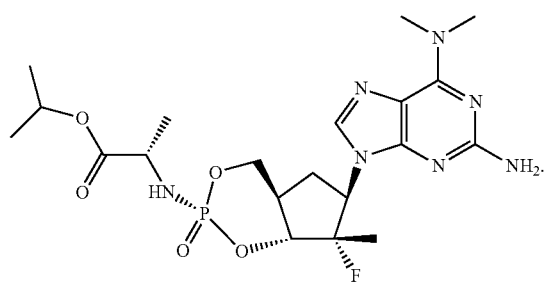 [SMILES: CC(C)OC(=O)[C@H](C)N[P@]1(=O)OC[C@H]2C[C@@H](n3cnc4c(N(C)C)nc(N)nc43)[C@](C)(F)[C@@H]2O1]

Compound X-6 is an HCV polymerase inhibitor and is represented by the following structure:

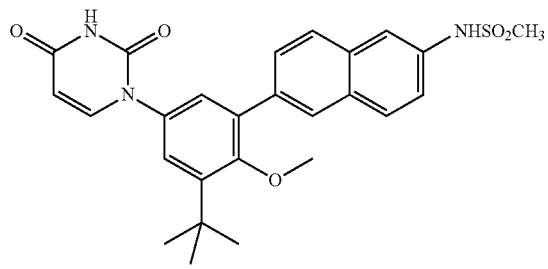

Compound X-7 is an HCV polymerase inhibitor and is represented by the following structure:

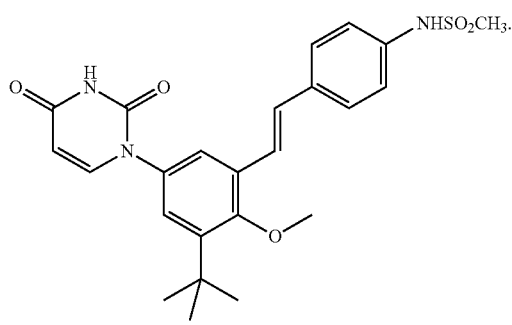

See U.S. Publication No. 2013/0102525 and references therein.

Compound X-8 is an HCV protease inhibitor and is represented by the following chemical structure:

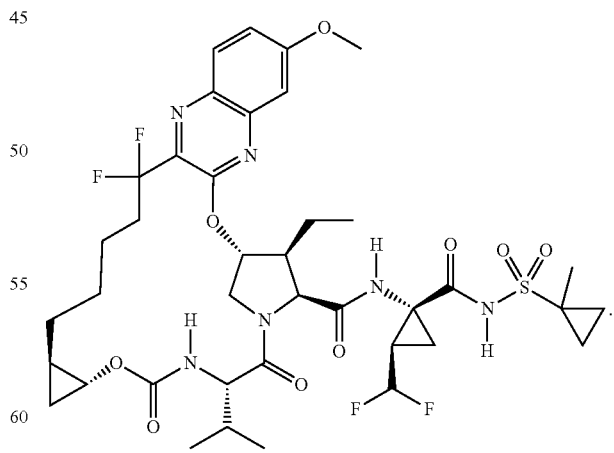

See U.S. Publication No. 2014/0017198 and references therein.

Compound X-9 is an HCV protease inhibitor and is represented by the following chemical structure:

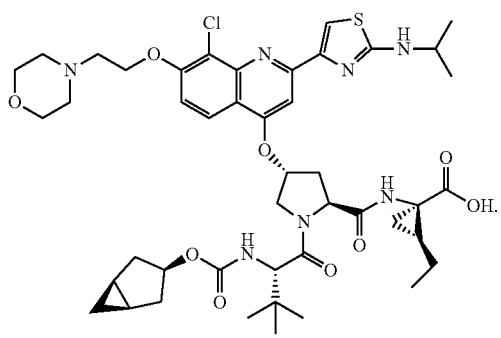

See U.S. Pat. No. 8,178,491 and references therein.

Compound X-10 is an HCV protease inhibitor and is represented by the following chemical structure:

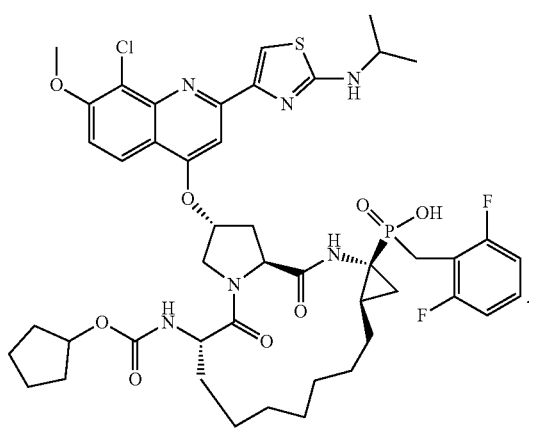 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]

Compound X-11 is an HCV protease inhibitor and is represented by the following chemical structure:

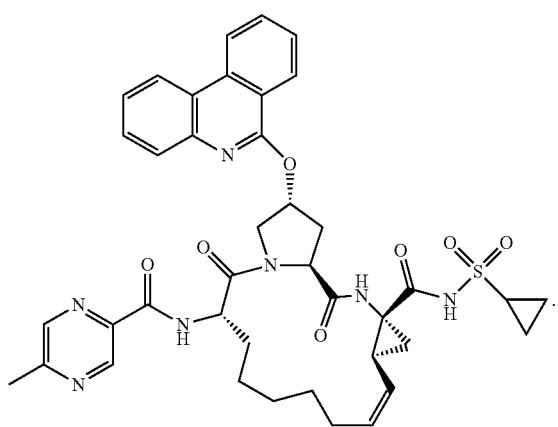 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

See U.S. Publication No. 2013/0102525 and references therein.

In another embodiment, the present application provides for a method of treating hepatitis C in a human patient in need thereof comprising administering to the patient a therapeutically effective amount of a pharmaceutical composition as described herein and an additional therapeutic selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising an effective amount of Compound I; and an effective amount of sofosbuvir wherein the sofosbuvir is substantially crystalline as described herein and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

The additional therapeutic agent may be one that treats other conditions such as HIV infections. Accordingly, the additional therapeutic agent may be a compound useful in treating HIV, for example HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, the additional therapeutic agent may be selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 11) a CCR5 inhibitor, e.g., aplaviroc, vicriviroc, INCB9471, PRO-140, INCB15050, PF-232798, CCR5mAb004, and maraviroc, 12) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 13) ribavirin analogs, e.g., rebetol, copegus, levovirin, VX-497, and viramidine (taribavirin)

14) NS5a inhibitors, e.g., A-831, A-689, and BMS-790052,

15) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 16) NS3 protease inhibitors, e.g., SCH-503034 (SCH-7), VX-950 (Telaprevir), ITMN-191, and BILN-2065, 17) alpha-glucosidase 1 inhibitors, e.g., MX-3253 (celgosivir) and UT-231B, 18) hepatoprotectants, e.g., IDN-6556, ME 3738, MitoQ, and LB-84451, 19) non-nucleoside inhibitors of HCV, e.g., benzimidazole derivatives, benzo-1,2,4-thiadiazine derivatives, and phenylalanine derivatives, 20) other drugs for treating Hepatitis C, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 21) pharmacokinetic enhancers, e.g., BAS-100 and SPI452, 20) RNAse H inhibitors, e.g., ODN-93 and ODN-112, and 22) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In one embodiment, the additional therapeutic agent is ribavirin. Accordingly, methods described herein include a method of treating hepatitis C in a human patient in need thereof comprising administering to the patient a therapeutically effective amount of ribavirin and a therapeutically effective amount of a pharmaceutical composition, pharmaceutical dosage form, or tablet as described herein. In a further embodiment, the ribavirin and pharmaceutical composition, pharmaceutical dosage form, or tablet comprising sofosbuvir and Compound I is administered for about 12 weeks or less. In further embodiments, the ribavirin and pharmaceutical composition, pharmaceutical dosage form, or tablet comprising sofosbuvir and Compound I is administered for about 8 weeks or less, or for about 6 weeks or less, or for about 4 weeks or less.

It is contemplated that the additional therapeutic agent will be administered in a manner that is known in the art and the dosage may be selected by someone of skill in the art. For example, the additional agent may be administered in a dose from about 0.01 milligrams to about 2 grams per day.

EXAMPLES

In the following examples and throughout this disclosure, abbreviations as used herein have respective meanings as follows:

EXAMPLE 1

| Tablet Preparation and Formulation | |
|---|---|
| % CV | Percent coefficient of variation |
| AUC | Area Under the Curve |
| $AUC_{inf}$ | Area under the plasma concentration-time curve from time zero extrapolated to the infinite time |
| $AUC_{tau}$ | Area under the plasma concentration-time curve for a dosing interva |
| CL | Drug clearance |
| $C_{last}$ | Last observed plasma concentration |
| $C_{max}$ | Maximum Concentration |
| cP | Centipoise |
| $EC_{50}$ | Concentration of a compound inhibiting birus replication by 50% |
| $E_{max}$ | Maximal effect range |
| F | Bioavailability |
| FDC | Fixed dose combination |
| GLSM | Geometric least-squares means |
| GT | Genotype |
| h or hr | Hour |
| HCV | Hepatitis C virus |
| HFM | High-fat/high-calorie meal |
| ICH | International Conference on Harmonisation; Impurities guidelines |
| kg | Kilogram |
| LLOQ | Lower limit of quantitation |
| m | Meter |
| MFM | Moderate-fat/moderate-calorie meal |
| mg | Milligram |
| mL | Milliliter |
| ng | Nanogram |
| ° C. | Degrees Celsius |
| PD | Pharmacodynamics |
| PK | Pharmacokinetics |
| Q1, Q3 | first quartile, third quartile |
| RNA | Ribonucleic Acid |
| s | Second |
| SAE | Serious adverse event |
| SOF | Sofosbuvir (GS-7977; formerly PSI-7977) |
| SVR | Sustained Virologic Response |
| $t_{1/2}$ | Half-life (h) |
| $t_{last}$ | Time of last observed plasma concentration(h) |
| $t_{max}$ | Time to reach $C_{max}$ (h) |
| w | Weight |

EXAMPLE 1-continued

Tablet Preparation and Formulation

| XRPD | Xray Powder Diffraction |
|---|---|
| μm | Micrometer |

A. Dose Selection of Tablets i. Sofosbuvir

The sofosbuvir dose selected for the tablet formulation is 400 mg once daily. Support for the 400 mg sofosbuvir dose can be derived from $E_{max}$ PK/PD modeling with early virological and human exposure data which also supports the selection of a 400 mg sofosbuvir dose over others tested.

The mean sofosbuvir major metabolite $AUC_{tau}$ for the 400 mg sofosbuvir dose is associated with approximately 77% of the maximal HCV RNA change from baseline achievable as determined by this model, a value which is on the cusp of the plateau of the exposure-response sigmoidal curve. In a sigmoidal $E_{max}$ model, there is a relatively linear exposure-response relationship in the 20 to 80% maximal effect range. Therefore, given that sofosbuvir exposure with 200 mg tablets appears dose-proportional with single doses up to 1200 mg, doses below 400 mg are expected to yield considerable reductions in the magnitude of HCV RNA change from baseline. Similarly, in order to improve upon an efficacy prediction of 77% in the plateau of the exposure-response curve, substantial increases in exposure (and hence dose) would be needed for an appreciable increase in antiviral effect.

The sofosbuvir dose of 400 mg once daily was associated with higher SVR rates in genotype 1 HCV infected patients as compared to the 200 mg once daily dose when given in conjunction with additional HCV therapeutics for 24 weeks. Safety and tolerability appeared similar across both dose levels. In addition, when sofosbuvir 400 mg once daily plus other HCV therapeutics were given to genotype 2 or 3 HCV infected patients, 100% SVR24 was observed.

ii. Compound I

Following single and multiple oral doses of Compound I, maximum plasma concentrations occurred between 1.50 and 3.25 hours (median $T_{max}$). Compound I exhibited nonlinear PK across the dose range of 5 to 450 mg. Increases in exposure, as assessed by AUC and $C_{max}$, were greater than dose-proportional from 5 to 50 mg and were less than dose-proportional from 50 to 450 mg. Consistent with the half-life of Compound I, modest accumulation was observed with time. After multiple once-daily doses of Compound I greater than 5 mg, the mean plasma concentrations of Compound I at 24 hours postdose were above the protein-adjusted concentration of a compound inhibiting virus replication by 50% ($EC_{50}$) for genotype 1 to 6 HCV replicons (Table 1)

TABLE 1

| PK Parameter | 5 mg (N = 12) | 50 mg (N = 12) | 100 mg (N = 24) | 150 mg (N = 12) | 450 mg (N = 12) |
|---|---|---|---|---|---|
| | | Single Dose (Cohorts 1-6[a]) | | | |
| $AUC_{last}$ (ng · h/mL) | 134.2 (69.6) | 2970.7 (40.1) | 4985.6 (44.8) | 4925.9 (48.0) | 9503.8 (34.5) |
| $AUC_{inf}$ (ng · h/mL) | 158.9 (64.0) | 3017.2 (40.1) | 5055.0 (45.3) | 4978.3 (47.8) | 9578.1 (34.3) |
| $C_{max}$ (ng/mL) | 22.4 (55.4) | 371.3 (32.7) | 574.9 (37.2) | 608.4 (46.7) | 1121.6 (31.7) |
| $C_{last}$ (ng/mL) | 1.40 (26.9) | 2.34 (61.4) | 2.85 (80.3) | 2.23 (40.1) | 3.28 (50.5) |
| $T_{max}$ (h) | 1.50 (1.50, 2.00) | 2.50 (2.00, 3.00) | 2.50 (2.50, 3.00) | 2.75 (2.50, 3.50) | 3.25 (2.50, 3.75) |
| $T_{last}$ (h) | 24.00 (14.00, 36.00) | 72.00 (48.00, 96.00) | 95.00 (71.50, 96.00) | 96.00 (84.02, 96.00) | 96.00 (96.00, 96.00) |
| $t_{1/2}$ (h) | 11.20 (5.40, 16.89) | 13.62 (10.62, 16.47) | 15.73 (12.63, 17.11) | 16.16 (14.55, 17.55) | 14.97 (12.91, 16.73) |
| CL/F (mL/h) | 58,398.0 (124.4) | 19,188.4 (39.2) | 24,617.9 (50.8) | 72,185.5 (196.4)[b] | 53,676.4 (42.5) |

| PK Parameter | 5 mg (N = 12) | 50 mg (N = 12) | 150 mg (N = 12) | 450 mg (N = 12) |
|---|---|---|---|---|
| | | Multiple Dose (Cohorts 1-4[a]) | | |
| $AUC_{tau}$ (ng · h/mL) | 172.3 (51.7) | 3032.6 (40.4) | 4890.8 (45.4) | 9511.2 (40.9) |
| $C_{max}$ (ng/mL) | 28.3 (49.3) | 411.4 (40.7) | 669.4 (48.1) | 1195.7 (38.0) |
| $C_{tau}$ (ng/mL) | 2.2 (76.0) | 37.9 (59.5) | 63.4 (42.8) | 127.7 (44.3) |
| $T_{max}$ (h) | 2.00 (1.25, 2.50) | 2.50 (2.25, 3.00) | 2.50 (2.50, 3.50) | 3.00 (2.50, 4.25) |
| $T_{last}$ (h) | 24.00 (24.00, 24.00) | 24.00 (24.00, 24.00) | 24.00 (24.00, 24.00) | 24.00 (24.00, 24.00) |
| $t_{1/2}$ (h) | 13.73 (13.19, 15.88) | 13.02 (11.43, 16.23) | 15.15 (12.03, 15.63) | 11.74 (10.64, 13.12) |
| $CL_{SS}/F$ (mL/h) | 36,095.7 (46.4) | 19,593.0 (50.5) | 45,082.3 (88.3) | 58,804.6 (57.3) |

Note:
All PK parameters are reported as mean (% CV), except for $T_{max}$, $T_{last}$, and $t_{1/2}$, which are reported as median (Q1, Q3).
[a]Compound I dosing by cohort: Cohort 1 = 50 mg, Cohort 2 = 150 mg, Cohort 3 = 5 mg, Cohort 4 = 450 mg, Cohorts 5 and 6 (pooled in the fasted state) = 100 mg.
[b]Mean (% CV) CL/F for the Compound I 150 mg group (excluding one patient) was 31,403.8 (40.5) mL/h.

B. Solid Dispersion Comprising Compound I

To make the tablets comprising the combination of sofosbuvir and Compound I as described herein, a solid dispersion comprising Compound I was co-formulated with crystalline sofosbuvir. The starting material of the solid dispersion can be a variety of forms of Compound I including crystalline forms, amorphous form, salts thereof, solvates and/or free base. In certain embodiments, Compound I is the amorphous free base.

The spray dry feed solution was prepared by solubilizing Compound I and polymer in the feed solvent. In certain cases, aggressive mixing or homogenization can be used to avoid clumping of the composition.

The feed solution was initially evaluated for appropriate solvent with regard to solubility, stability, and viscosity. Ethanol, methanol, acetone, and dichloromethane all demonstrated excellent solubility. Ethanol and methanol-based feed stocks were assessed for preparation ease and spray dried at a range of inlet and outlet temperatures to assess the robustness of the spray dry process. Both solvents gave rapid dissolution of Compound I and copovidone.

Spray drying out of ethanol resulted in high yields across a wide range of spray-drying outlet temperatures with no material accumulation on the spray dry chamber. Overall, the Compound I solid dispersion in a Compound I to copovidone ratio of 1:1 demonstrated good chemical stability in the ethanolic feed solution.

An ethanolic solution of 10% Compound I and 10% copovidone was prepared using homogenization. Viscosity of ethanolic solutions of Compound I:copovidone were low.

Spray drying was conducted using a commercially available spray dryer (e.g., Anhydro, Buchi, or Niro spray dryer).

Organic volatile impurities, including the spray dry solvent ethanol may be rapidly removed during secondary drying in a tray oven 60° C., purged with room air or via a double cone dryer. Loss on drying can be attributable to water, which can be confirmed by Karl Fischer titration. Residual ethanol was reduced below ICH guidelines of 0.5% w/w by 6 hours of drying.

C. Tablet Preparation i. Monolayer Tablet

The solid dispersion comprising Compound I was blended with sofosbuvir and excipients and milled to facilitate mixing and blend uniformity. Either a coblend or codry granulation process can be used. Coblend granulation is a multi-step process consisting of separate dry granulations for each active ingredient with excipients followed by the blending of the two granulations together. Codry granulation consisted of dry granulating both active ingredients and excipients together.

An in-process milling step may be used to deagglomerate relatively small but hard agglomerates present in the drug substance. To limit any loss of drug substance, Compound I may be blended with all intragranular excipients prior to milling through a conical screen mill, e.g., with a 125R screen and a tip speed of 6 m/s. A milling step was tested, but found to be unnecessary. A secondary blend may be conducted prior to lubrication with magnesium stearate, followed by roller compaction and milling through an in-line oscillating mill. This process results in powder blends with satisfactory flow characteristics and compression properties.

The granules were then mixed with a lubricant prior to tablet compression. The total resulting core tablet weight was about 1000 mg for the 100 mg Compound I/400 mg Sofosbuvir tablet. The total resulting core tablet weight was about 600 mg for the 25 mg Compound I/400 mg Sofosbuvir tablet.

Film-coating of the tablets is provided to reduce photolytic degradation. Tablets were coated to a target 3% weight gain. The film-coating material was a polyvinylalcohol-based coating. Exemplary tablet formulations are provided in Tables 2 and 3.

TABLE 2

| Ingredient | % w/w | Component Weight (mg/tablet) |
| --- | --- | --- |
| Sofosbuvir | 66.7 | 400 |
| Compound I Solid Dispersion (Compound I:copovidone 1:1) | 8.3 | 50 |
| Microcrystalline Cellulose | 20.5 | 123 |
| Croscarmellose Sodium | 3 | 18 |
| Magnesium Stearate | 1.5 | 9 |
| Total Tablet Core Weight | 100 | 600 |
| Film coating | 3 | 18 |
| Purified Water | — | — |
| Total Coated Tablet Weight | | 618 |

TABLE 3

| Ingredient | % w/w | Component Weight (mg/tablet) |
| --- | --- | --- |
| Sofosbuvir | 40 | 400 |
| Compound I Solid Dispersion (Compound I:copovidone 1:1) | 20 | 200 |
| Microcrystalline Cellulose | 35.5 | 355 |
| Croscarmellose Sodium | 3 | 30 |
| Magnesium Stearate | 1.5 | 15 |
| Total Tablet Core Weight | 100 | 1000 |
| Film coating | 3 | 30 |
| Purified Water | — | — |
| Total Coated Tablet Weight | | 1030 | ii. Bilayer Tablet

Tablets comprising the co-formulation of a solid dispersion comprising Compound I and crystalline sofosbuvir can also be made as a bilayer tablet wherein each active ingredient is in a separate layer. To make the bilayer tablet, a Compound I:copovidone solid dispersion is made by dissolving Compound I and copovidone into ethanol, and then spray drying the mixture. The spray dried Compound I:copovidone (1:1) solid dispersion is further dried in a secondary dryer. Next, the spray dried Compound I:copovidone solid dispersion is then blended with excipients. The mixture is milled and then blended with lubricant prior to dry granulation. The Compound I granules are blended with extragranular lubricant. Separately, the sofosbuvir drug substance is blended with excipients, and then the mixture is milled and then blended with lubricant prior to dry granulation. The sofosbuvir granules are then blended with extragranular lubricant. Finally, the sofosbuvir powder blend and Compound I powder blend are compressed into bilayer tablet cores. The bilayer tablet cores are then film-coated prior to packaging. Representative example compositions of a bilayer tablets comprising the solid dispersion of Compound I and sofosbuvir are shown in Tables 4 and 5.

TABLE 4

| Ingredient | % w/w | Component Weight (mg/tablet) |
|---|---|---|
| Layer 1 | | |
| Sofosbuvir | 57 | 400 |
| Microcrystalline Cellulose | 13 | 90 |
| Croscarmellose Sodium | 3.5 | 24 |
| Magnesium Stearate | 1 | 8 |
| Layer 2 | | |
| Compound I Solid Dispersion (Compound I:copovidone 1:1) | 7 | 50 |
| Microcrystalline Cellulose | 14.5 | 100 |
| Croscarmellose Sodium | 3.5 | 25 |
| Magnesium Stearate | 0.5 | 3 |
| Total Tablet Core | 100.00 | 700 |

TABLE 5

| Ingredient | % w/w | Component Weight (mg/tablet) |
|---|---|---|
| Layer 1 | | |
| Sofosbuvir | 40 | 400 |
| Microcrystalline Cellulose | 14 | 140 |
| Croscarmellose Sodium | 2.4 | 24 |
| Magnesium Stearate | 0.8 | 8 |
| Layer 2 | | |
| Compound I Solid Dispersion (Compound I:copovidone 1:1) | 20 | 200 |
| Microcrystalline Cellulose | 19 | 190 |
| Croscarmellose Sodium | 3 | 30 |
| Magnesium Stearate | 0.8 | 8 |
| Total Tablet Core | 100 | 1000 |

Example 2: Drug-Drug Interaction Between SOF and Compound I

A PK drug-drug interaction between SOF and Compound I was evaluated. Compound I plasma exposures ($AUC_{tau}$, $C_{max}$, and $C_{tau}$) were not affected by the coadministration of SOF, and thus no dose adjustment is required for Compound I. Sofosbuvir plasma exposures increased approximately 1.8-fold ($C_{max}$) and 2.4-fold (AUC) when coadministered with Compound I. SOF metabolite I $C_{max}$ and AUC increased approximately 1.6- and 1.8-fold, respectively, when SOF was coadministered with Compound I (solid dispersion, Compound I:copovidone 1:1). approximately 1.8-fold ($C_{max}$) and 2.4-fold (AUC) when coadministered with Compound I. SOF metabolite II (the predominant circulating nucleoside metabolite of SOF) $C_{max}$ decreased approximately 36%, but AUC was unaffected by coadministration of SOF and Compound I. See Table 6.

TABLE 6

| | Compound I | | |
|---|---|---|---|
| Compound I PK Parameter | Compound I 150 mg (N = 18) | SOF 400 mg + Compound I 150 mg (N = 18) | % GLSM Ratio (SOF + Compound I/Compound I) (90% CI) |
| $AUC_{tau}$ (ng · h/mL) | 7284.95 | 8138.22 | 111.71 (107.54, 116.04) |
| $C_{max}$ (ng/mL) | 932.27 | 987.69 | 105.94 (101.86, 110.20) |
| $C_{tau}$ (ng/mL) | 101.09 | 118.90 | 117.61 (111.94, 123.57) |
| SOF | | | |
| SOF PK Parameter | SOF 400 mg (N = 18) | SOF 400 mg + Compound I 150 mg (N = 18) | % GLSM Ratio (SOF + Compound I/SOF) (90% CI) |
| $AUC_{last}$ (ng · h/mL) | 1154.59 | 2749.10 | 238.10 (214.62, 264.16) |
| $AUC_{inf}$ (ng · h/mL) | 1159.50 | 2756.96 | 237.77 (214.27, 263.85) |
| $C_{max}$ (ng/mL) | 880.28 | 1593.80 | 181.06 (149.43, 219.38) |
| SOF metabolite I | | | |
| SOF metabolite I PK Parameter | SOF 400 mg (N = 18) | SOF 400 mg + Compound I 150 mg (N = 18) | % GLSM Ratio (SOF + Compound I/SOF) (90% CI) |
| $AUC_{last}$ (ng · h/mL) | 1861.41 | 3394.32 | 182.35 (167.52, 198.50) |
| $AUC_{inf}$ (ng · h/mL) | 1926.09 | 3455.70 | 179.42 (165.03, 195.06) |
| $C_{max}$ (ng/mL) | 455.77 | 736.88 | 161.68 (145.27, 179.94) |
| SOF metabolite II | | | |
| SOF metabolite II PK Parameter | SOF 400 mg (N = 18) | SOF 400 mg + Compound I 150 mg (N = 18) | % GLSM Ratio (SOF + Compound I/SOF) (90% CI) |
| $AUC_{last}$ (ng · h/mL) | 11,173.87 | 12,610.86 | 112.86 (107.90, 118.05) |
| $AUC_{inf}$ (ng · h/mL) | 11,842.52 | 13,774.96 | 116.32 (110.99, 121.90) |
| $C_{max}$ (ng/mL) | 1080.97 | 693.62 | 64.17 (58.45, 70.44) |

Note:
Data are reported as GLSM. Cohort 7 = SOF 400 mg single dose (Day 1); Compound I 150 mg multiple doses (Days 5-13); Compound I 150 mg + SOF 400 mg single dose (Day 14).

The effect of Compound I on SOF (and SOF metabolite I) exposure is likely due to Compound I inhibition of the intestinal efflux drug transporters p-glycoprotein (Pgp) and possibly breast cancer resistance protein (BCRP), as SOF is known to be a substrate of these transporters. The increase in the systemic exposure of SOF (and SOF metabolite I) by Compound I was similar to that seen previously with Pgp and/or BCRP inhibitors and does not warrant any SOF dose modification.

Example 3: Food Effect

The exposure of Compound I solid dispersion (Compound I:copovidone 1:1) administered with a high-fat/high-calorie meal (HFM) as a single agent was modestly reduced (14% decrease in AUC and 25% decrease in Cmax) compared to fasted administration (Table 7). The exposure of Compound I (solid dispersion) when administered with a HFM as part of the sofosbuvir/Compound I (solid dispersion) FDC was comparatively improved, resulting in a modest increase in exposure compared to fasted administration (~20% increase in AUC and 5% increase in Cmax, Table 8). This increase in exposure suggests that the bioavailability of Compound I administered as part of the sofosbuvir/Compound I FDC is improved relative to Compound I as a single agent tablet. Table 8, below shows exposures and GMRs of Compound I from the fixed dose combination under the different fed states.

TABLE 7

| Compound I PK Parameter | Compound I 100 mg Fed (N = 12) | Compound I 100 mg Fasted (N = 12) | % GLSM Ratio (Fed/Fasted) | 90% CI |
|---|---|---|---|---|
| GLSM | | | | |
| Light Breakfast | | | | |
| $AUC_{last}$ (ng · h/mL) | 6728.66 | 5389.63 | 124.84 | (110.02, 141.67) |
| $AUC_{inf}$ (ng · h/mL) | 6820.80 | 5469.11 | 124.72 | (109.94, 141.48) |
| $C_{max}$ (ng/mL) | 784.70 | 581.72 | 134.89 | (116.84, 155.74) |
| HFM | | | | |
| $AUC_{last}$ (ng · h/mL) | 3222.57 | 3746.30 | 86.02 | (73.17, 101.12) |
| $AUC_{inf}$ (ng · h/mL) | 3267.75 | 3786.61 | 86.30 | (73.43, 101.42) |
| $C_{max}$ (ng/mL) | 364.39 | 485.72 | 75.02 | (62.56, 89.97) |

TABLE 8

| Mean (% CV) | SOF/Compound I FDC (Fasted, N = 30) | (MFM, N = 30) | (HFM, N = 30) | MFM/ Fasted GMR (90% CI) | HFM/ Fasted GMR (90% CI) |
|---|---|---|---|---|---|
| $AUC_{inf}$ (ng · hr/mL) | 4520 (47.6) | 5930 (44.3) | 5060 (43.4) | 1.33 (1.10, 1.63) | 1.21 (0.99, 1.48) |
| $AUC_{last}$ (ng · hr/mL) | 4440 (47.7) | 5850 (44.1) | 4990 (43.2) | 1.34 (1.09, 1.64) | 1.22 (0.99, 1.49) |
| $C_{max}$ (ng/mL) | 562 (44.6) | 710 (39.4) | 544 (35.9) | 1.29 (1.07, 1.56) | 1.05 (0.87, 1.26) |

Example 4: Safety and Efficacy of Treatment with Interferon-Free, Ribavirin-Free, Combination of Compound I and Sofosbuvir for 12 Weeks in Treatment Naïve Patients with Genotype 1-6 HCV Infection Compound I is a HCV NS5A inhibitor that has demonstrated potent activity against genotype 1-6 HCV in a 3-day monotherapy study. This example shows the results of the study of the combination of sofosbuvir (SOF) and Compound I solid dispersion (Compound I:copovidone 1:1) in patients with genotype 1-6 HCV infection.

Methods: Treatment naïve genotype 1-6 HCV-infected patients without cirrhosis were randomized 1:1 to receive 400 mg of SOF and 25 mg of Compound I once daily or 400 mg of SOF and 100 mg of Compound I once daily for 12 weeks.

Results: 154 patients (36% GT1, 14% GT2, 35% GT3, 9% GT4, <1% GT5, and 6% GT6) were randomized and treated; 64% were male, 85% white, and 48% had IL28B CC genotype. All patients had HCV RNA<LLOQ by week 4 of treatment except one genotype 3 HCV-infected patient treated with 400 mg of SOF and 25 mg of Compound I (this patient stopped treatment for non-response at Week 8). Results through post-treatment week 4 (SVR4) are presented below. Two patients relapsed, one with genotype 1 HCV infection and one with genotype 3 HCV infection, both received 400 mg of SOF and 25 mg of Compound I. The most frequently reported adverse events (>10%) were fatigue, headache and nausea. There were no discontinuations due to adverse events. Four patients reported 5 SAEs; none were considered related to study drug. There was no evidence of drug related changes in hematologic, chemistry or urinalysis parameters.

The treatment of SOF and Compound I for 12 weeks was well tolerated and resulted in high SVR4 rates in patients with genotype 1-6 HCV infection (Table 9).

TABLE 9

SVR4 in Patients Treated with SOF + Compound I for 12 Weeks

| HCV genotype | SOF (400 mg) + Compound I (25 mg) | SOF (400 mg) + Compound I (100 mg) |
|---|---|---|
| GT1 | 96% (26/27) | 100% (28/28) |
| GT2 | 91% (10/11)[a] | 100% (10/10) |
| GT3 | 89% (24/27)[a] | 100% (27/27) |
| GT4 | 100% (7/7) | 86% (6/7)[a] |
| GT5 | 100% (1/1) | — |
| GT6 | 100% (4/4) | 100% (5/5) |

[a]One patient per group was lost to follow-up prior to posttreatment week 4.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

We claim:
1. A pharmaceutical composition comprising:
a) a solid dispersion comprising an effective amount of Compound I dispersed within a polymer matrix comprising copovidone, Compound I having the formula:

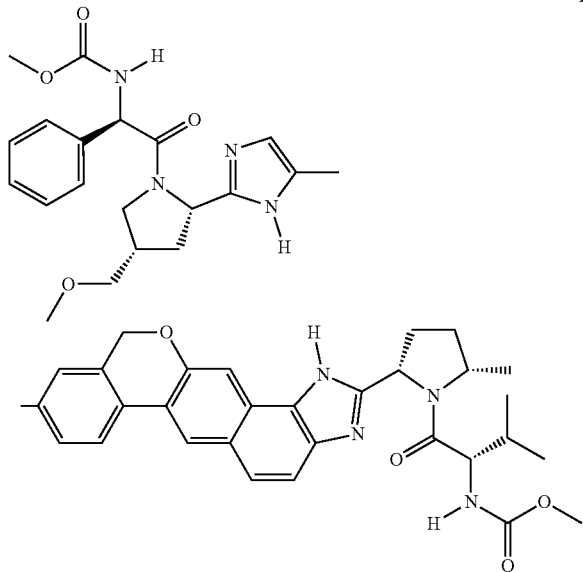

wherein Compound I is substantially amorphous; and
b) an effective amount of sofosbuvir having the formula:

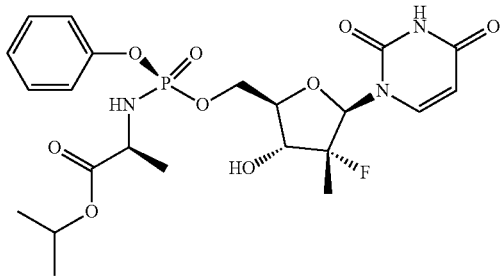 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

wherein the sofosbuvir is substantially crystalline.

2. The pharmaceutical composition of claim 1, wherein the weight ratio of Compound I to copovidone in the solid dispersion is from about 5:1 to about 1:5.

3. The pharmaceutical composition of claim 2, wherein the weight ratio of Compound I to copovidone in the solid dispersion is from about 2:1 to about 1:2.

4. The pharmaceutical composition of claim 3, wherein the weight ratio of Compound I to copovidone in the solid dispersion is about 1:1.

5. The pharmaceutical composition of claim 3, wherein the weight ratio of Compound I to copovidone in the solid dispersion is about 1:2.

6. The pharmaceutical composition of claim 1, comprising from about 30% to about 70% w/w of sofosbuvir.

7. The pharmaceutical composition of claim 1, comprising from about 35% to about 45% w/w of sofosbuvir.

8. The pharmaceutical composition of claim 1, comprising about 40% w/w of sofosbuvir.

9. The pharmaceutical composition of claim 1, comprising from about 60% to about 70% w/w of sofosbuvir.

10. The pharmaceutical composition of claim 1, comprising about 67% w/w of sofosbuvir.

11. The pharmaceutical composition of claim 1, comprising from about 1% to about 45% w/w of the solid dispersion.

12. The pharmaceutical composition of claim 1, comprising from about 1% to about 25% w/w of the solid dispersion.

13. The pharmaceutical composition of claim 1, comprising about 1% w/w, about 8% w/w, or about 20% w/w of the solid dispersion.

14. The pharmaceutical composition of claim 1, wherein the crystalline sofosbuvir has XRPD 2θ-reflections at about:
(1) 7.5, 9.6, and 18.3° 2θ±0.2;
(2) 5.0, 7.3, and 18.1° 2θ±0.2;
(3) 6.9, 24.7, and 25.1° 2θ±0.2;
(4) 19.7, 20.6, and 24.6° 2θ±0.2;
(5) 5.0, 6.8, and 24.9° 2θ±0.2;
(6) 5.2, 6.6, and 19.1° 2θ±0.2; or
(7) 6.1, 20.1, and 20.8° 2θ±0.2.

15. The pharmaceutical composition of claim 1, wherein the crystalline sofosbuvir has XRPD 2θ-reflections at about: 6.1, 8.2, 10.4, 12.7, 17.2, 17.7, 18.0, 18.8, 19.4, 19.8, 20.1, 20.8, 21.8, and 23.3° 2θ±0.2.

16. The pharmaceutical composition of claim 1, wherein the crystalline sofosbuvir has XRPD 2θ-reflections at about: 6.1 and 12.7° 2θ±0.2.

17. The pharmaceutical composition of claim 1, further comprising a diluent, a disintegrant, a lubricant, or any combination thereof.

18. The pharmaceutical composition of claim 17, wherein the diluent is selected from the group consisting of dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof.

19. The pharmaceutical composition of claim 18, wherein the diluent is microcrystalline cellulose and is present in an amount from about 5% to about 40% w/w.

20. The pharmaceutical composition of claim 17, wherein the disintegrant is selected from the group consisting of croscarmellose sodium, crospovidone, microcrystalline cellulose, modified corn starch, povidone, pregelatinized starch, sodium starch glycolate, and combinations thereof.

21. The pharmaceutical composition of claim 20, wherein the disintegrant is croscarmellose sodium and is present in an amount from about 1% to about 10% w/w.

22. The pharmaceutical composition of claim 17, wherein the lubricant is selected from the group consisting of calcium stearate, magnesium stearate, polyethylene glycol, sodium stearyl fumarate, stearic acid, talc, and combinations thereof.

23. The pharmaceutical composition of claim 22, wherein the lubricant is magnesium stearate and is present in an amount from about 0.5% to about 3% w/w.

24. The pharmaceutical composition of claim 1, comprising:
a) about 30% to about 70% w/w of sofosbuvir; and
b) about 1% to about 45% w/w of the solid dispersion.

25. The pharmaceutical composition of claim 1, comprising
a) about 40% w/w of sofosbuvir; and
b) about 20% w/w of the solid dispersion.

26. The pharmaceutical composition of claim 1, further comprising
c) about 5% to about 40% w/w microcrystalline cellulose,
d) about 1% to about 10% w/w croscarmellose sodium, and
e) about 0.1% to about 3% w/w magnesium stearate.

27. The pharmaceutical composition of claim 1, comprising
a) about 67% w/w of sofosbuvir and
b) about 8% w/w of the solid dispersion.

28. The pharmaceutical composition of claim 1, further comprising
c) about 5% to about 25% w/w microcrystalline cellulose,
d) about 1% to about 10% w/w croscarmellose sodium, and
e) about 0.1% to about 3% w/w magnesium stearate.

29. The pharmaceutical composition of claim 1, wherein the composition is formulated for immediate release.

30. A pharmaceutical dosage form comprising the pharmaceutical composition of claim 1, comprising from about 5 mg to about 450 mg of Compound I.

31. The pharmaceutical dosage form of claim 30, comprising from about 5 mg to about 150 mg of Compound I.

32. The pharmaceutical dosage form of claim 31, comprising about 100 mg of Compound I.

33. The pharmaceutical dosage form of claim 31, comprising about 25 mg of Compound I.

34. The pharmaceutical dosage form of claim 30, comprising from about 200 mg to about 600 mg of sofosbuvir.

35. The pharmaceutical dosage form of claim 30, comprising from about 300 mg to about 500 mg of sofosbuvir.

36. The pharmaceutical dosage form of claim 30, comprising about 400 mg of sofosbuvir.

37. A tablet comprising the pharmaceutical dosage form of claim 30.

38. The tablet of claim 37, further comprising a film coating.

39. The tablet of claim 38, wherein the film coating is a polyvinylalcohol-based coating.

40. A method of treating hepatitis C in a human patient in need thereof comprising administering to the patient the pharmaceutical composition of claim 1.

41. The method of claim 40, wherein the pharmaceutical composition is administered for about 12 weeks or less.

42. The method of claim 40, wherein the pharmaceutical composition is administered for about 8 weeks or less.

43. The method of claim 40, wherein the pharmaceutical composition is administered for about 4 weeks or less.

44. The method of claim 40, wherein a sustained virologic response is achieved by about 4 weeks.

45. The method of claim 40, wherein a sustained virologic response is achieved by about 12 weeks.

46. The method of claim 40, wherein a sustained virologic response is achieved by about 6 months.

47. The method of claim 40, further comprising administering an additional therapeutic agent.

48. The method of claim 47, wherein the additional therapeutic agent is ribavirin.

49. A method of treating hepatitis C in a human patient in need thereof comprising administering to the patient a therapeutically effective amount of ribavirin and the pharmaceutical composition of claim 1; wherein the ribavirin and pharmaceutical composition is administered for about 12 weeks or less.

50. The method of claim 49, wherein the ribavirin and the pharmaceutical composition is administered for about 8 weeks or less.

51. The method of claim 49, wherein the ribavirin and the pharmaceutical composition is administered for about 4 weeks or less.

52. The method of claim 40, wherein the pharmaceutical composition is administrable without regard to fed state.

53. The pharmaceutical composition of claim 1, wherein the solid dispersion is a spray dried solid dispersion.

54. The pharmaceutical composition of claim 1, wherein the solid dispersion is made by dissolving Compound I and copovidone in ethanol to form a mixture and spray drying the mixture to form a spray dried solid dispersion.

55. The pharmaceutical composition of claim 54, wherein the spray dried solid dispersion is further dried in a secondary dryer.

56. The pharmaceutical composition of claim 53, comprising:
a) about 40% w/w of sofosbuvir; and
b) about 20% w/w of the solid dispersion, wherein the weight ratio of Compound I to copovidone in the solid dispersion is about 1:1.

57. The pharmaceutical composition of claim 1, wherein the substantially amorphous Compound I is greater than 99% amorphous.

58. The pharmaceutical composition of claim 1, wherein the substantially crystalline sofosbuvir is greater than 99% crystalline.

* * * * *